US011827902B2

(12) United States Patent
Shi et al.

(10) Patent No.: US 11,827,902 B2
(45) Date of Patent: *Nov. 28, 2023

(54) END-TO-END CELL THERAPY AUTOMATION

(71) Applicants: LONZA WALKERSVILLE, INC., Walkersville, MD (US); LONZA COLOGNE GMBH, Cologne (DE); OCTANE BIOTECH INC., Kingston (CA)

(72) Inventors: Yaling Shi, Walkersville, MD (US); Erika McAfee, Walkersville, MD (US); Samatha Bandapalle, Walkersville, MD (US); Ann Siehoff, Cologne (DE); Timo Gleissner, Cologne (DE); Joseph O'Connor, Walkersville, MD (US); Eytan Abraham, Walkersville, MD (US); Kelly Purpura, Kingston (CA); Nuala Trainor, Kingston (CA); Timothy Smith, Kingston (CA)

(73) Assignees: LONZA WALKERSVILLE, INC., Walkersville, MD (US); LONZA COLOGNE GMBH, Cologne (DE); OCTANE BIOTECH INC., Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/751,999

(22) Filed: May 24, 2022

(65) Prior Publication Data
US 2022/0282213 A1 Sep. 8, 2022

Related U.S. Application Data

(63) Continuation of application No. 16/119,618, filed on Aug. 31, 2018, now Pat. No. 11,447,745.

(60) Provisional application No. 62/670,391, filed on May 11, 2018, provisional application No. 62/553,214, filed on Sep. 1, 2017.

(51) Int. Cl.

| | |
|---|---|
| *C12N 5/0783* | (2010.01) |
| *C12M 3/00* | (2006.01) |
| *C12M 1/00* | (2006.01) |
| *C12M 1/34* | (2006.01) |
| *C07K 14/725* | (2006.01) |
| *C07K 14/705* | (2006.01) |
| *C12N 5/00* | (2006.01) |
| *C12N 5/16* | (2006.01) |
| *C12N 15/86* | (2006.01) |

(52) U.S. Cl.
CPC ........ *C12N 5/0636* (2013.01); *C07K 14/7051* (2013.01); *C07K 14/70521* (2013.01); *C12M 23/42* (2013.01); *C12M 29/20* (2013.01); *C12M 41/00* (2013.01); *C12N 5/0018* (2013.01); *C12N 5/163* (2013.01); *C12N 15/86* (2013.01); *C12N 2510/00* (2013.01); *C12N 2740/10041* (2013.01); *C12N 2740/15041* (2013.01)

(58) Field of Classification Search
None
See application file for complete search history.

(56) References Cited

U.S. PATENT DOCUMENTS

| | | |
|---|---|---|
| 4,642,120 A | 2/1987 | Nevo et al. |
| 4,939,151 A | 7/1990 | Bacehowski et al. |
| 5,041,138 A | 8/1991 | Vacanti et al. |
| 5,081,036 A | 1/1992 | Familletti |
| 5,240,854 A | 8/1993 | Berry et al. |
| 5,246,699 A | 9/1993 | Debre et al. |
| 5,424,209 A | 6/1995 | Kearney |
| 5,478,479 A | 12/1995 | Herrig |
| 5,549,134 A | 8/1996 | Browne et al. |
| 5,688,687 A | 11/1997 | Palsson et al. |
| 5,728,581 A | 3/1998 | Schwartz et al. |
| 5,786,207 A | 7/1998 | Katz et al. |
| 5,792,603 A | 8/1998 | Dunkelman et al. |
| 5,827,729 A | 10/1998 | Naughton et al. |
| 5,842,477 A | 12/1998 | Naughton et al. |
| 5,846,828 A | 12/1998 | Peterson et al. |
| 5,882,929 A | 3/1999 | Fofonoff et al. |
| 5,891,455 A | 4/1999 | Sittinger et al. |
| 5,902,741 A | 5/1999 | Purchio et al. |
| 5,906,934 A | 5/1999 | Grande et al. |
| 5,922,604 A | 7/1999 | Stapleton et al. |
| 5,928,936 A | 7/1999 | Ingram |
| 5,985,653 A | 11/1999 | Armstong et al. |
| 5,989,913 A | 11/1999 | Anderson et al. |

(Continued)

FOREIGN PATENT DOCUMENTS

| | | |
|---|---|---|
| AU | 2002/324169 A1 | 3/2003 |
| CA | 2223525 A1 | 12/1996 |

(Continued)

OTHER PUBLICATIONS

Andris et al., "Naïve T Cells are Resistant to Anergy Induction by Anti-CD3 Antibodies," The Journal of Immunology (2004) 173(5):3201-3208.

(Continued)

*Primary Examiner* — Nancy J Leith

(74) *Attorney, Agent, or Firm* — MEDLER FERRO WOODHOUSE & MILLS

(57) ABSTRACT

The present disclosure provides an automated method of producing genetically modified immune cells, including chimeric antigen receptor T (CAR T) cells, utilizing a fully-enclosed cell engineering system.

17 Claims, 40 Drawing Sheets

(56) References Cited

U.S. PATENT DOCUMENTS

| | | | |
|---|---|---|---|
| 5,994,129 A | 11/1999 | Armstrong et al. | |
| 6,048,721 A | 4/2000 | Armstrong et al. | |
| 6,048,722 A | 4/2000 | Farb et al. | |
| 6,060,306 A | 5/2000 | Flatt et al. | |
| 6,096,532 A | 8/2000 | Armstrong et al. | |
| 6,121,042 A | 9/2000 | Peterson et al. | |
| 6,123,655 A | 9/2000 | Fell | |
| 6,197,575 B1 | 3/2001 | Griffith et al. | |
| 6,214,574 B1 | 4/2001 | Kopf | |
| 6,228,635 B1 | 5/2001 | Armstrong et al. | |
| 6,238,908 B1 | 5/2001 | Armstrong et al. | |
| 6,297,046 B1 | 10/2001 | Smith et al. | |
| 6,323,146 B1 | 11/2001 | Pugh et al. | |
| 6,402,941 B1 | 6/2002 | Lucido et al. | |
| 7,348,175 B2 | 3/2008 | Vilendrer et al. | |
| 7,906,323 B2 | 3/2011 | Cannon et al. | |
| 8,492,140 B2 | 7/2013 | Smith et al. | |
| 8,727,132 B2 | 5/2014 | Miltenyi et al. | |
| 9,499,780 B2 | 11/2016 | Smith et al. | |
| 9,534,195 B2 | 1/2017 | Smith et al. | |
| 9,629,877 B2 | 4/2017 | Cooper et al. | |
| 9,701,932 B2 | 7/2017 | Smith et al. | |
| 9,783,768 B2 | 10/2017 | Larcher et al. | |
| 10,131,876 B2* | 11/2018 | Kaiser | C12N 5/0087 |
| 10,253,316 B2 | 4/2019 | Masquelier et al. | |
| 10,273,300 B2 | 4/2019 | Bedoya et al. | |
| 10,428,351 B2* | 10/2019 | Crisman | A61P 31/00 |
| 11,208,626 B2 | 12/2021 | Mason et al. | |
| 11,371,018 B2* | 6/2022 | Shi | C07K 14/7051 |
| 11,447,745 B2* | 9/2022 | Shi | C07K 14/70521 |
| 2001/0002152 A1 | 5/2001 | Ohno et al. | |
| 2001/0021529 A1 | 9/2001 | Takagi | |
| 2001/0043918 A1 | 11/2001 | Masini et al. | |
| 2002/0002554 A1 | 1/2002 | Herdman | |
| 2002/0009797 A1 | 1/2002 | Wolf et al. | |
| 2002/0009803 A1 | 1/2002 | Vajta | |
| 2002/0025547 A1 | 2/2002 | Rao | |
| 2002/0037580 A1 | 3/2002 | Schoeb | |
| 2002/0146816 A1 | 10/2002 | Vellinger et al. | |
| 2002/0155487 A1 | 10/2002 | Greenberger et al. | |
| 2002/0179525 A1 | 12/2002 | Shaffer et al. | |
| 2003/0032071 A1 | 2/2003 | Wang et al. | |
| 2003/0040104 A1 | 2/2003 | Barbera-Guillem | |
| 2003/0054335 A1 | 3/2003 | Taya et al. | |
| 2003/0159946 A1 | 8/2003 | Eden et al. | |
| 2003/0215935 A1 | 11/2003 | Coon | |
| 2004/0048364 A1 | 3/2004 | Trosch | |
| 2005/0064465 A1 | 3/2005 | Dettloff et al. | |
| 2005/0130297 A1 | 6/2005 | Sarem et al. | |
| 2005/0186671 A1 | 8/2005 | Cannon et al. | |
| 2006/0151185 A1 | 7/2006 | Takagi et al. | |
| 2015/0034484 A1 | 2/2015 | Nakasone et al. | |
| 2015/0344844 A1 | 12/2015 | Better et al. | |
| 2016/0012278 A1 | 1/2016 | Banhazi et al. | |
| 2016/0122782 A1 | 5/2016 | Crisman et al. | |
| 2017/0005125 A1 | 1/2017 | Itonaga et al. | |
| 2017/0037369 A1 | 2/2017 | Ramsborg et al. | |
| 2017/0051252 A1 | 2/2017 | Morgan et al. | |
| 2019/0169572 A1 | 6/2019 | Shi et al. | |
| 2019/0211294 A1 | 7/2019 | Karnieli | |

FOREIGN PATENT DOCUMENTS

| | | | |
|---|---|---|---|
| CN | 106062185 A | 10/2016 | |
| DE | 4021123 A1 | 4/1991 | |
| EP | 248675 A1 | 12/1987 | |
| GB | 1356794 A | 6/1974 | |
| JP | H02-119772 A | 5/1990 | |
| JP | H02-174848 A | 7/1990 | |
| JP | H03-500847 A | 2/1991 | |
| JP | H05-503418 A | 6/1993 | |
| JP | H06-54678 A | 3/1994 | |
| JP | H06-261736 A | 9/1994 | |
| JP | H07-501206 A | 2/1995 | |
| JP | H08-56646 A | 3/1996 | |
| JP | H11-507229 A | 6/1999 | |
| JP | 2001-275659 A | 10/2001 | |
| JP | 2001-517428 A | 10/2001 | |
| JP | 2002-500004 A | 1/2002 | |
| JP | 2008-113600 A | 5/2008 | |
| JP | 2011-036263 A | 2/2011 | |
| JP | 2017-513499 A | 6/2017 | |
| JP | 2017-513891 A | 6/2017 | |
| JP | 2017-514517 A | 6/2017 | |
| KR | 20000023786 U | 9/2001 | |
| KR | 2016-0145162 A | 12/2016 | |
| WO | 91/05849 A1 | 5/1991 | |
| WO | 93/03142 A1 | 2/1993 | |
| WO | 97/12960 A2 | 4/1997 | |
| WO | 99/33951 A1 | 7/1999 | |
| WO | 99/47922 A2 | 9/1999 | |
| WO | 2000/046349 A1 | 8/2000 | |
| WO | 2001/000783 A2 | 1/2001 | |
| WO | 2001/02030 A2 | 1/2001 | |
| WO | 2002/028996 A1 | 4/2002 | |
| WO | 2002/088295 A1 | 11/2002 | |
| WO | 2003/022985 A2 | 3/2003 | |
| WO | 2003/085101 A1 | 10/2003 | |
| WO | 2003/087292 A2 | 10/2003 | |
| WO | 2013/082509 A1 | 6/2013 | |
| WO | 2015/162211 A1 | 10/2015 | |
| WO | 2016/069993 A1 | 5/2016 | |
| WO | 2016/118780 A1 | 7/2016 | |
| WO | 2016/168275 A1 | 10/2016 | |
| WO | 2017/068425 A1 | 4/2017 | |
| WO | 2018/015561 A1 | 1/2018 | |
| WO | 2018/136566 A1 | 7/2018 | |

OTHER PUBLICATIONS

Atkuri et al., "Culturing at atmospheric oxygen levels impacts lymphocyte function," PNAS (2005) 102 (10):3756-3759.

Austyn et al., "T cell activation by anti-CD3 antibodies: function of Fc receptors on B cell blasts, but not resting B cells, and CD18 on the responding T cells." European Journal of Immunology (1987) 17(9):1329-1335.

Avgoustiniatos et al., "Commercially Available Gas-Permeable Cell Culture Bags May Not Prevent Anoxia in Cultured or Shipped Islets," Transplant Proc. (2008) 40(2):395-400.

Baroja et al., "The anti-T cell monoclonal antibody 9.3 (Anti-CD28) provides a helper signal and bypasses the need for accessory cells in T Cell activation with immobilized anti-CD3 and mitogens," Cellular Immunology (1989) 120 (1):205-217.

Berdeja et al., "First-in-human multicenter study of bb2121 anti-BCMA CAR T-cell therapy for relapsed/refractory multiple myeloma: Updated results," Journal of Clinical Oncology (2017) 35(15):3010.

Bohnenkamp et al., "Bioprocess development for the cultivation of human T-lymphocytes in a clincal scale," Cytotechnology (2002) 38:135-145.

Carpenter et al., "Non-Fc Receptor-Binding Humanized Anti-CD3 Antibodies Induce Apoptosis of Activated Human T Cells," The Journal of Immunology (2000) 165(11):6208-6213.

Ceuppens et al., "T cell unresponsiveness to the mitogenic activity of OKT3 antibody results from a deficiency of monocyte Fc gamma receptors for murine IgG2a inability to cross-link the T3-Ti complex," The Journal of Immunology (1985) 135(6):3882-3886.

Chai et al., "Immobilized anti-CD3 mAb induces anergy in murine naïve and memory CD4+ T cells in vitro.," Int Immunol. (1997) 9(7):935-944.

Charron et al., "Monocyte:T cell interaction regulates human T cell activation through a CD28/CD46 crosstalk," Immunol Cell Biol. (2015) 93(9):796-803.

Church et al., "Tumor-specific CD4+ T cells maintain effector and memory tumor-specific CD8+ T cells," European Journal of Immunology (2014) 44:69-79.

Clavreul et al., "Interelationship between CD3 and CD28 pathways in a murine T cell thymoma," Molecular Immunology (2000) 37(10):571-577.

(56) References Cited

OTHER PUBLICATIONS

Declaration form James C. Leung, Sumbitted in *Lonza Walkersville, Inc. v. Adva Biotechnology LTD.,* United States District Court for the District of Maryland, Case No. 8:20-cv-03099-PX, Jan. 7, 2022.
Declaration from Mark Selker, Submitted in *Lonza Walkersville, Inc. v. Adva Biotechnology LTD.,* United States District Court for the District of Maryland, Case No. 8:20-cv-03099-PX, Jan. 5, 2022.
Dudley et al., "Generation of Tumor-Infiltrating Lymphocyte Cultures for Use in Adoptive Transfer Therapy for Melanoma Patients," J Immunother. (2003) 26(4):332-342.
Farndale, "Pulsed Electromagnetic Fields to Promote Collagen Production in Bone Marrow Fibroblasts via Athermal Mechanisms" Calcif Tissue Int (1985) 37:178-182.
Fathman et al., "Molecular mechanisms of CD4+ T-cell anergy," Nature Reviews Immunology (2007) 7:599-609.
FDA, Available online at: https://www.fda.gov/downloads/AdvisoryCommittees/CommitteesMeetingMaterials/Drugs/OncologicDrugsAdvisoryCommittee/UCM566166.pdf, 2017.
FDA, Regenerative Medicine Advanced Therapy Designation. (2017). Available at: https://www.fda.gov/BiologicsBloodVaccines/CellularGeneTherapyProducts/ucm537670.htm. (Accessed: Aug. 8, 2017).
FDA, Sepax Cell Separation System and single use kits. (2011). Available at: https://www.fda.gov/downloads/BiologicsBloodVaccines/BloodBloodProducts/ApprovedProducts/SubstantiallyEquivalent510kDeviceInformation/UCM278385.pdf. (Accessed: Nov. 8, 2017).
Feldmann et al., "Novel humanized and highly efficient bispecific antibodies mediate killing of prostate stem cell antigen-expressing tumor cells by CD8+ and CD4+ T cells," J Immunol. (2012) 189(6):3249-3259.
Fleischer et al., "Differential expression and function of CD80 (B7-1) and CD86 (B7-2) on human peripheral blood monocytes," Immunology (1996) 89(4):592-598.
Gottschalk et al., The hype, hope and reality of personalization. The Medicine Maker (2015) p. 38-41.
Greenwald et al., "The B7 Family Revised," Annual Review of Immunology (2005) 23:515-548.
Grishagin, Ivan V., "Automatic cell counting with ImageJ," Analytical Biochemistry (2015) 473:63-65.
Hammill et al., "Designed ankyrin repeat proteins are effective targeting elements for chimeric antigen receptors," Journal for ImmunoTherapy of Cancer (2015) 3(55):1-11.
Harding et al., "CD28-mediated signalling co-stimulates murine T cells and prevents induction of anergy in T-cell clones," Nature (1992) 356:607-609.
Hasegawa et al., "In vitro Stimulation of CD8 and CD4 T Cells by Dendritic Cells Loaded with a Complex of Cholesterol-Bearing Hydrophobized Pullulan and NY-ESO-1 Protein: Identification of a New HLA-DR15-Binding CD4 T-Cell Epitope," Clinical Cancer Research (2006) 12(6):1921-1927.
Hollyman et al., "Manufacturing validation of biologically functional T cells targeted to CD19 antigen for autologous adoptive cell therapy," J Immunother. (2009) 32(2):169-180.
Ju et al., "A functional anti-human 4-1BB ligand monoclonal antibody that enhances proliferation of monocytes by reverse signaling of 4-1BBL," Hybrid Hybridomics (2003) 22(5):333-338.
Kaiser et al., "Towards a commercial process for the manufacture of genetically modified T cells for therapy," Cancer Gene Therapy (2015) 22:72-78.
Kalos et al., "T Cells with Chimeric Antigen Receptors Have Potent Antitumor Effects and Can Establish Memory in Patients with Advanced Leukemia," Sci Transl Med. (2011) 3(95):1-21.
Kebriaei et al., "Phase I trials using Sleeping Beauty to generate CD19-specific CAR T cells," The Journal of Clinical Investigation (2016) 126(9):3363-3376.
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," Journal of Clinical Oncology (2016 33(6):540-549.
Konstantin B. Konstantinov, "Monitoring and Control of the Physiological State of Cell Cultures", Biotechnology and Bioengineering, vol. 52, pp. 271-289 (1996) (Year: 1996).
Lafferty et al., "A new analysis of allogeneic interactions," Aust J Exp Biol Med Sci. (1975) 53(1):27-42.
Laux et al., "Response Differences between Human CD4+ and CD8+ T-Cells during CD28 Costimulation: Implications for Immune Cell-Based Therapies and Studies Related to the Expansion of Double-Positive T-Cells during Aging," Clinical Immunology (2000) 96(3):187-197.
Ledbetter et al., "CD28 Ligation in T-cell Activation: Evidence for Two Signal Transduction Pathways," Blood (1990) 75(7):1531-1539.
Levine et al., "Global Manufacturing of CAR T Cell Therapy," Molecular: Therapy: Methods & Clinical Development (2017) 4:92-101.
Li et al., "Comparison of anti-CD3 and anti-CD28-coated beads with soluble anti-CD3 for expanding human T cells: Differing impact on CD8 T cell phenotype and responsiveness to restimulation," Journal of Translational Medicine (2010) 8(104):1-15.
Lock et al., "Automated Manufacturing of Potent CD20-Directed Chimeric Antigen Receptor T Cells for Clinical Use," Human Gene Therapy (2017) 28(10):914-925.
Locke et al., "Abstract CT019: Primary results from ZUMA-1: a pivotal trial axicabtagene ciloleucel (axicel; KTE-C19) in patients with refractory aggressive non-Hodgkin lymphoma (NHL)," Cancer Research (2017) 77(13).
Locke et al., "Phase 1 Results of ZUMA-1: A Multicenter Study of KTE-C19 Anti-CD19 CAR T Cell Therapy in Refractory Aggressive Lymphoma," Molecular Therapy (2017) 25(1):285-295.
Lu et al., "A Rapid Cell Expansion Process for Production of Engineered Autologous CAR-T Cell Therapies," Human Gene Therapy Methods (2016) 27(6):209-218.
Lu et al., "Automated dynamic fed-batch process and media optimization for high productivity cell culture process development," (2013) 110(1):191-205.
Lu et al., "Treatment of Patients with Metastatic Cancer Using a Major Histocompatibility Complex Class II-Restricted T-Cell Receptor Targeting the Cancer Germline Antigen MAGE-A3," Journal of Clinical Oncology (2017) 35 (29):3322-3329.
Mock et al., "Automated manufacturing of chimeric antigen receptor T cells for adoptive immunotherapy using CliniMACS Prodigy," Cytotherapy (2016) 18(8):1002-1011.
Morrissey et al., "End-to-End Cell Therapy Automation: An Immunotherapy Case Study," BioPharm International (2017) 2:10-18.
Nilsson et al., "Optimal Blood Mononuclear Cell Isolation Procedures for Gamma Interferon Enzyme-Linked Immunospot Testing of Healthy Swedish and Tanzanian Subjects," Clinical and Vaccine Immunology (2008) 15 (4):585-589.
Nociari et al., "A novel one-step, highly sensitive fluorometric assay to evaluate cell-mediated cytotoxicity," Journal of Immunological Methods (1998) 213(2):157-167.
Odeleye et al., "On the fluid dynamics of a laboratory scale single-use stirred bioreactor," Chemical Engineering Science (2014) 111(100):299-312.
Reusch et al., "A tetravalent bispecific TandAb (CD19/CD3), AFM11, efficiently recruits T cells for the potent lysis of CD19+ tumor cells," MAbs (2015) 7(3):584-604.
Riddell et al., "Adoptive Therapy with Chimeric Antigen Receptor Modified T Cells of Defined Subset Composition," Cancer J (2014) 20(2):141-144.
Riddell et al., "The use of anti-CD3 and anti-CD28 monoclonal antibodies to clone and expand human antigen-specific T cells," Journal of Immunological Methods (1990) 128(2):189-201.
Romagnani, S, "Type 1 T helper and type 2 T helper cells: functions, regulation and role in protection and disease," Int J Clin Lab Res (1991) 21(2):152-158.
Schwartz, RH, "A cell culture model for T lymphocyte clonal anergy," Science (1990) 248(4961):1349-1356.

(56) References Cited

OTHER PUBLICATIONS

Schwartz, RH, "T cell anergy," Annu Rev Immunol. (2003) 21:305-334.
Shi et al., Performance of Mammalian Cell Culture Bioreactor with a New Impeller Design, Biotechnology and Bioengineering, Jun. 20, 1992, pp. 260-270, vol. 40, John Wiley & Sons, Inc.
Tangying et al., "A Rapid Cell Expansion Process for Production of Engineering Autologous CAR-T Cell Therapies," Human Gene Therapy Methods (2016) 27(6):209-218.
Tax et al., "Polymorphism in mitogenic effect of IgG1 monoclonal antibodies against T3 antigen on human T cells," Nature (1983) 304(5925):445:447.
Trainor et al., "Rethinking clinical delivery of adult stem cell therapies," Nature Biotechnology (2014) 32:729-735.
Trickett et al., "T cell stimulation and expansion using anti-CD3/CD28 beads," Journal of Immunological Methods (2003) 275(1-2):251-255.
Tuefferd et al., "HER2 Status in Ovarian Carcinomas: A Multicenter GINECO Study of 320 Patients," PLoS ONE (2007) 11:e1138.
Turtle et al., "CD19 CAR-T cells of defined CD4+ :CD8+ composition in adult B cell ALL patients," The Journal of Clinical Investigation (2016) 126(6):2123-2138.
Vanseggelen et al., "Chimeric antigen receptor-engineered T cells as oncolytic virus carriers," Molecular Therapy—Oncolytics (2015) 150014.
Verwilghen et al., "Differences in the stimulating capacity of immobilized anti-CD3 monoclonal antibodies: variable dependence on interleukin-1 as a helper signal for T-cell activation," Immunology (1991) 72:269-276.
Wang et al., "Clinical manufacturing of CAR T cells: foundation of a promising therapy" Mol. Ther.—Oncolytics (2016) 3:16015.
Wang et al., "Manufacture of tumor- and virus-specific T lymphocytes for adoptive cell therapies," Cancer Gene Ther. (2015) 22(2):85-94.
Wauwe et al., "OKT3: a monoclonal anti-human T lymphocyte antibody with potent mitogenic properties," The Journal of Immunology (1980) 124(6):2708-2713.
Wegener, C, "Cell Washing with the LOVO Cell Processing System," BioProcess International (2014) p. 78.
Weiss et al., "T cell activation: differences in the signals required for IL 2 production by nonactivated and activated T cells," J Immunol (1985) 135(6):3669-3673.
Wolf et al., "Induction of anergy in resting human T lymphocytes by immobilized anti-CD3 antibodies," European Journal of Immunology (1994) 24(6):1410-1417.
Yan et al., "HER2 expression status in diverse cancers: review of results from 37,992 patients," Cancer Metastasis Rev (2015) 34:157-164.
Zhu et al., "CD137 stimulation delivers an antigen-independent growth signal for T lymphocytes with memory phenotype," Immunobiology (2007) 109(11):4882-4889.
Aitken-Christie et al., Automation in Plant tissue culture—general introduction and overview, in Automation and Environmental Control in Plant Tissue Culture 757 (J. Aitken-Christie, T. Kozai & M. Lila Smith eds., 1995).
Apel et al., Integrated Clinical Scale Manufacturing System for Cellular Products Derived by Magnetic Cell Separation, Centrifugation and Cell Culture, Chemie Ingenieur Technik (2013).
Armstrong et al., Clinical Systems for the Production of Cells and Tissues for Human Therapy, in Novel Therapeutics From Modern Biotechnology 221 (D.L. Oxender et al. eds., 1999).
Blaeschke et al., Induction of A Central Memory and Stem Cell Memory Phenotype in Functionally Active CD4+ and CD8+ CAR T Cells Produced in an Automated Good Manufacturing Practice System for the Treatment of CD19+ Acute Lymphoblastic Leukemia, Cancer Immunology, Immunotherapy vol. 67, pp. 1053-1066 (2018), published Mar. 31, 2018.
Bousso, T-cell activation by dendritic cells in the lymph node: lessons from the movies, 8 Nature Reviews Immunology 675 (2008) ("Bousso 2008").
Kempner et al., A Review of Cell Culture Automation, 7 Journal of the Association for Laboratory Automation 56 (2002) ("Kempner 2002").
Koller et al., Clinical-scale human umbilical cord blood cell expansion in a novel automated perfusion culture system, Bone Marrow Transplantation (1998) ("Koller 1998").
Koller et al., Large-Scale Expansion of Human Stem and Progenitor Cells from Bone Marrow Mononuclear Cells in Continuous Perfusion Cultures, Blood (1993) ("Koller 1993A").
Koller et al., Tissue Engineering: Reconstitution of Human Hematopoiesis Ex Vivo, Biotechnology and Bioengineering (1993) ("Koller 1993B").
Kostov et al., Low-Cost Microbioreactor for High-Throughput Bioprocessing, 72 Biotechnology and Bioengineering, Feb. 5, 2001 ("Kostov 2001").
Krug et al., A GMP-compliant protocol to expand and transfect cancer patient T cells with mRNA encoding a tumor-specific chimeric antigen receptor, Cancer Immunol Immunotherapy (2014) ("Krug 2014").
Morse, Technology evaluation: Stem-cell therapy, Aastrom Biosciences Inc., Current Opinion in Molecule Therapeutics (1999) ("Morse 1999").
Oh et al., Frequent Harvesting from Perfused Bone Marrow Cultures Results in Increased Overall Cell and Progenitor Expansion, Biotechnology and Bioengineering (1994).
Priesner et al., Automated Enrichment, Transduction, and Expansion of Clinical-Scale CD62L+ T Cells for Manufacturing of Gene Therapy Medicinal Products, 27 Human Gene Therapy 10, 860-869 (2016).
Rosazza et al., Gene Electrotransfer: A Mechanistic Perspective, Current Gene Therapy (2016) ("Rosazza 2016").
Stiff et al., Autologous transplantation of ex vivo expanded bone marrow cells grown from small aliquots after high-dose chemotherapy for breast cancer, Blood (2000) ("Stiff 2000").
Zhang et al., Characterization of clinical grade CD19 chimeric antigen receptor T cells produced using automated CliniMACS Prodigy system, Drug Design, Development and Therapy (2018) ("Zhang 2018").
Zhu et al., Closed-system manufacturing of CD19 and dual-targeted CD20/19 chimeric antigen receptor T cells using the CliniMACS Prodigy device at an academic medical center, Cytotherapy (2018).
ReadyToProcess Wave 25 Bioreactor Systems, retrieved from https://www.cytivalifesciences.com/en/us/search#q=wave%2025%20rocking%20bioreactor%20system%20pdf&t=coveo5819fbca&f:@content_type=[Documents] (Publication Date: Feb. 18, 2022).

\* cited by examiner

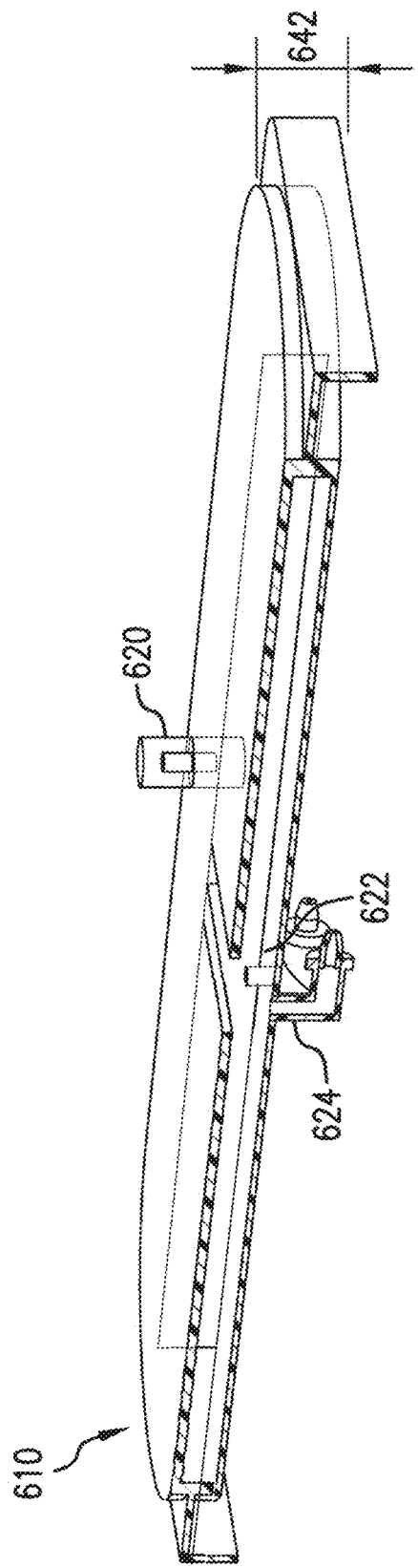

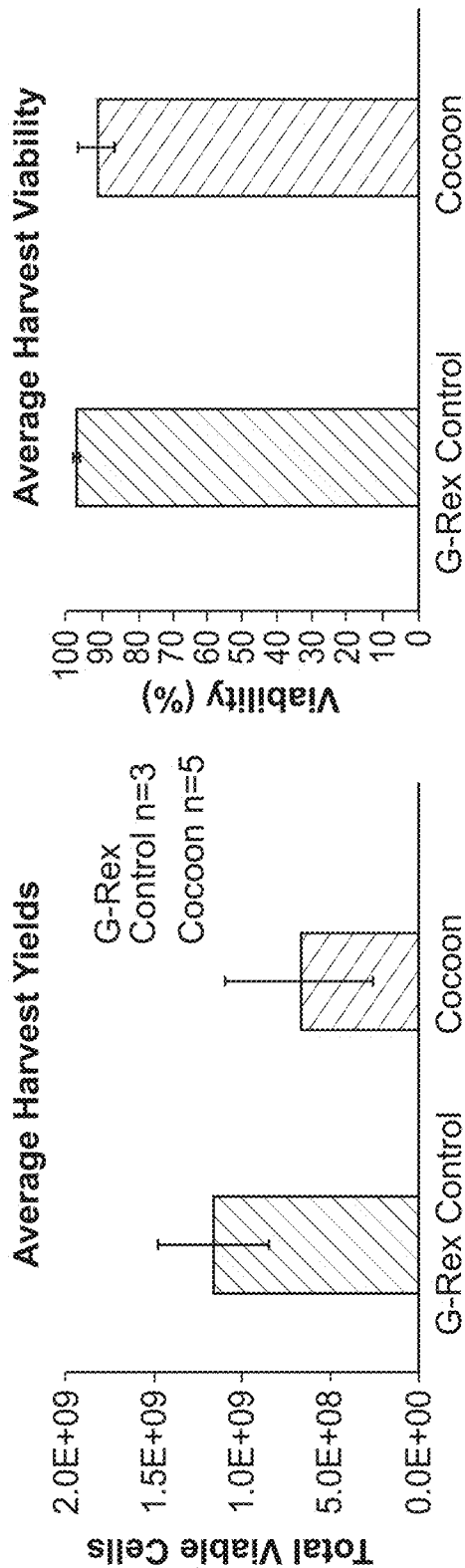
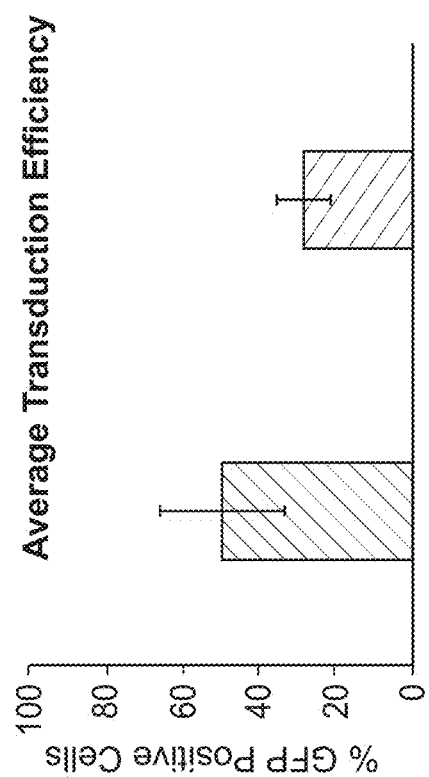
FIG. 7A
FIG. 7B
FIG. 7C

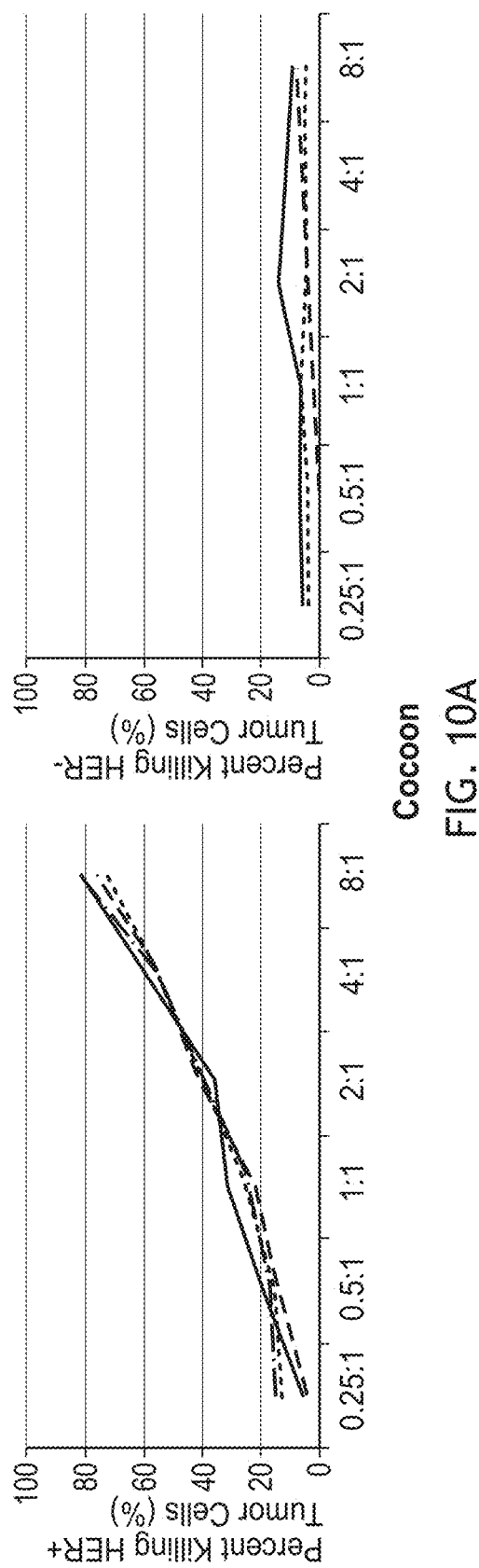
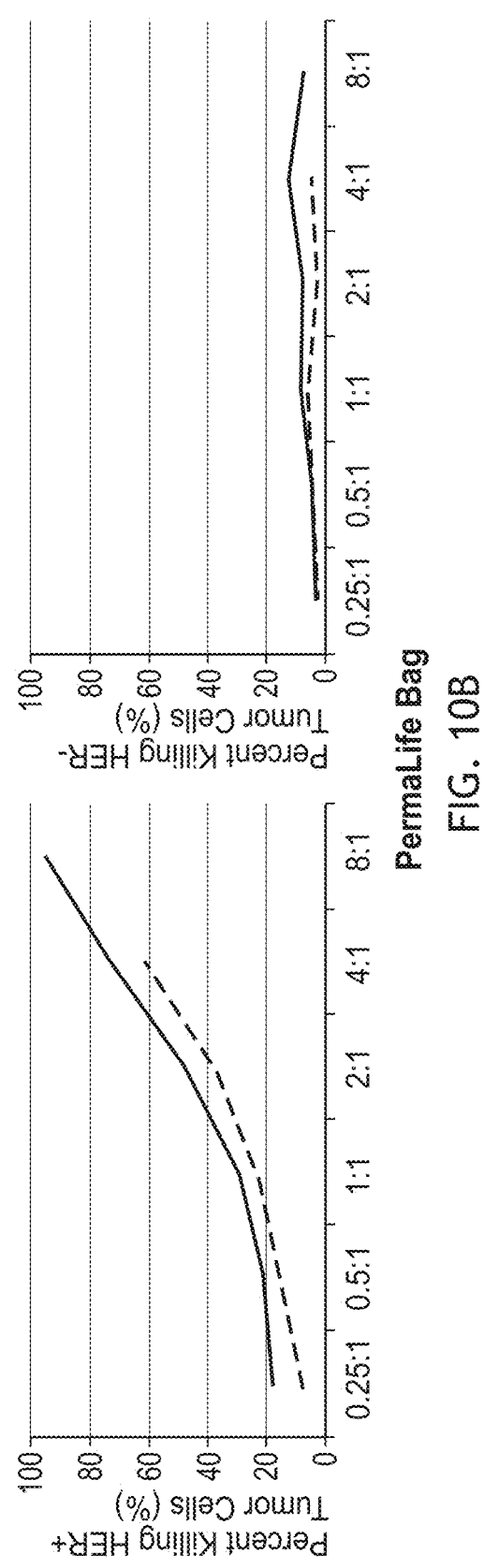
FIG. 10A Cocoon
FIG. 10B PermaLife Bag

| System | Total media (L) | Day 10 working volume (L) | CD3+CD4+ Cells (%) | CD3+CD8+ Cells (%) | Viability (%) | Total Viable Cells (x10⁹) | CAR T Cells (%) | Total CAR T Cells (x10⁹) | TNFα Producing CAR T Cells (%) | IFNγ Producing CAR T Cells (%) |
|---|---|---|---|---|---|---|---|---|---|---|
| Bag - Dynabead (n=2) | 1.15 | 1.15 | 48.2 ± 0.4 | 47.7 ± 0.1 | 98.0 ± 0.1 | 1.53 ± 0.07 | 41.8 ± 0.7 | 0.64 ± 0.04 | 41.4 ± 6.2 | 34.2 ± 4.5 |
| Bag - OKT3 (n=2) | 1.15 | 1.15 | 6.2 ± 0.2 | 85.9 ± 0.2 | 98.5 ± 0.1 | 2.08 ± 0.06 | 57.0 ± 0.8 | 1.19 ± 0.02 | 23.5 ± 2.1 | 6.8 ± 1.4 |
| Cocoon - Dynabead (n=4) | 1.15 | 0.46 | 41.3 ± 2.0 | 55.1 ± 2.5 | 96.5 ± 1.0 | 2.14 ± 0.08 | 64.6 ± 5.8 | 1.39 ± 0.13 | 53.1 ± 4.8 | 30.1 ± 6.9 |
| Cocoon - OKT3 (n=2) | 1.15 | 0.46 | 11.0 ± 2.1 | 83.2 ± 1.8 | 97.6 ± 0.7 | 2.55 ± 0.10 | 65.1 ± 2.4 | 1.66 ± 0.00 | 31.7 ± 3.3 | 12.6 ± 1.5 |

FIG. 16

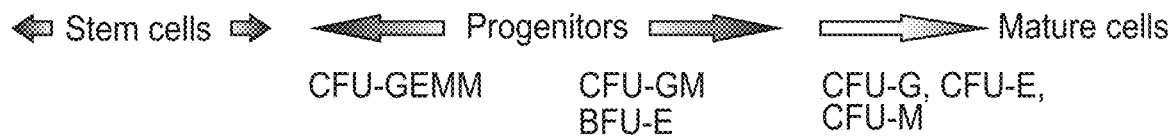
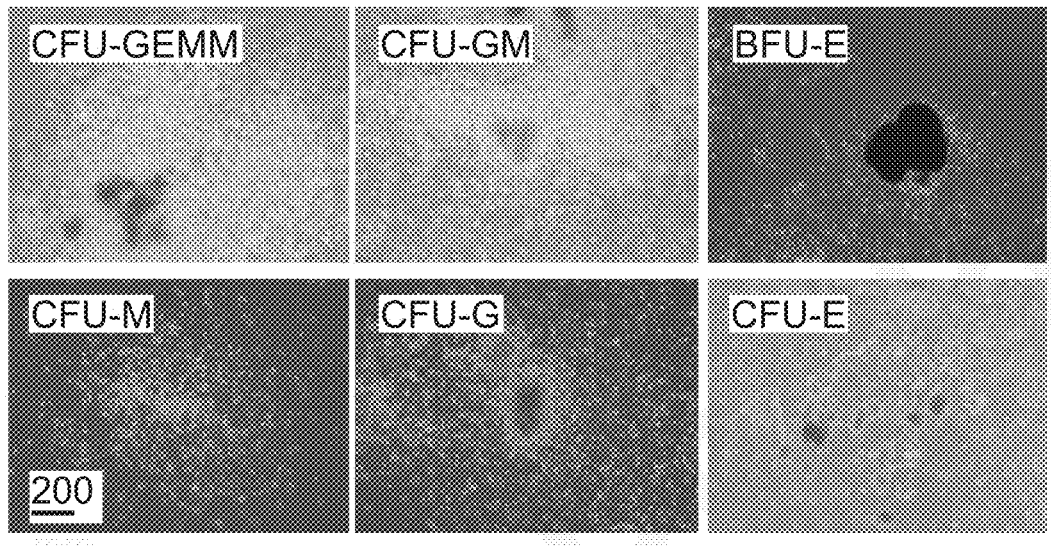
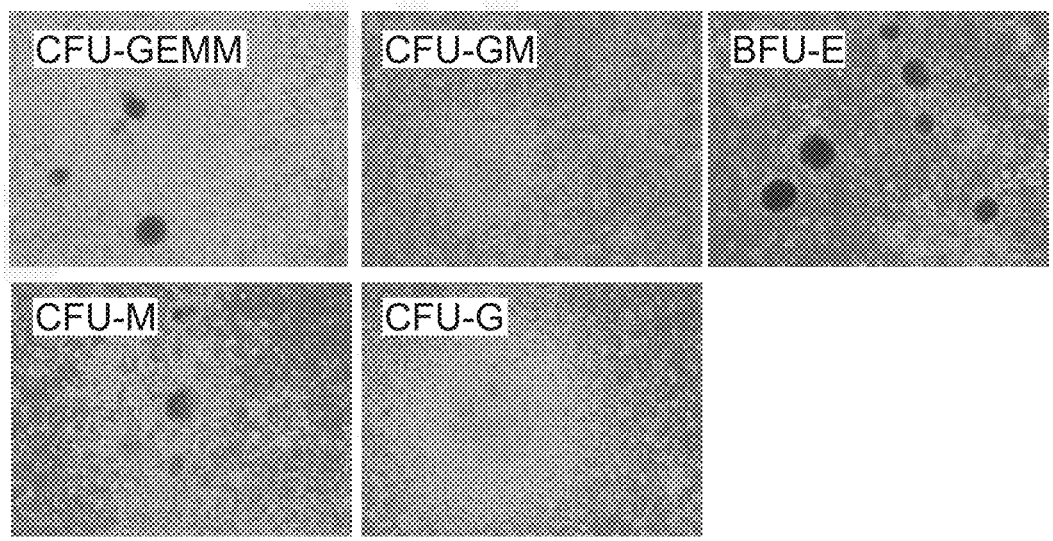
FIG. 22

END-TO-END CELL THERAPY AUTOMATION

CROSS-REFERENCE TO RELATED APPLICATIONS

The present application is a continuation of U.S. application Ser. No. 16/119,618, filed Aug. 31, 2018, which claims the benefit of U.S. Provisional Patent Application No. 62/670,391, filed May 11, 2018, and U.S. Provisional Patent Application No. 62/553,214, filed Sep. 1, 2017, the disclosures of each of which are incorporated by reference herein in their entireties.

FIELD OF THE INVENTION

The present disclosure provides an automated method of producing genetically modified immune cells, including chimeric antigen receptor T (CAR T) cells, utilizing a fully-enclosed cell engineering system.

BACKGROUND OF THE INVENTION

As anticipation builds about accelerated clinical adoption of advanced cell therapies, more attention is turning to the underlying manufacturing strategies that will allow these therapies to benefit patients worldwide. While cell therapies hold great promise clinically, high manufacturing costs relative to reimbursement present a formidable roadblock to commercialization. Thus, the need for cost effectiveness, process efficiency and product consistency is driving efforts for automation in numerous cell therapy fields, and particularly for T cell immunotherapies (see, e.g., Wang 2016).

Recent successful clinical results from immunotherapy trials using chimeric antigen receptor (CAR) T cells provide new hope to patients suffering from previously untreatable cancers (see, e.g., Lu 2017; Berdeja 2017; Kebriaei 2016). As these novel therapeutics move from the clinical trial stage to commercial scale-up, challenges arise related to cell manufacturing (see, e.g., Morrissey 2017).

The production of these cells may require significant manual involvement due to the patient-specific product. Automation of CAR T cell culture is particularly challenging due to the multiple sensitive unit operations, including cell activation, transduction and expansion. Activation may be particularly important as the efficiency of this process can impact transduction and expansion.

Integration of cell activation, transduction and expansion into a commercial manufacturing platform is critical for the translation of these important immunotherapies to the broad patient population. For these life-saving treatments to be applicable to the global patient population, a shift in manufacturing techniques must be implemented to support personalized medicine. The benefits of automation have previously been described (see, e.g., Trainor 2014; Mahdavi 2015). These benefits include labor time savings associated with using automation as well as improved product consistency, decreased room classification, decreased clean room footprint, decreased training complexities, and improved scale-up and tracking logistics. Furthermore, software can be used to streamline the documentation processes by using automatically generated electronic batch records to provide a history of all processing equipment, reagents, patient identification, operator identification, in-process sensor data, and so forth.

SUMMARY OF THE INVENTION

In some embodiments provided herein is a method for automated production of a genetically modified immune cell culture, the method comprising: activating an immune cell culture with an activation reagent to produce an activated immune cell culture; transducing the activated immune cell culture with a vector, to produce a transduced immune cell culture; expanding the transduced immune cell culture; concentrating the expanded immune cell culture of (c); and harvesting the concentrated immune cell culture of (d) to produce a genetically modified immune cell culture, further comprising washing either or both the expanded immune cell culture and the concentrated immune cell culture, wherein (a) through (e) are performed by a fully enclosed cell engineering system and (a) through (e) are optimized via a process to produce the genetically modified immune cell culture.

In further embodiments, provided herein is a method for promoting a preferred phenotype of a genetically modified immune cell culture, the method comprising: activating an immune cell culture with an activation reagent to produce an activated immune cell culture, wherein the activation reagent and activating conditions promote the phenotype of the genetically modified immune cell culture; transducing the activated immune cell culture with a vector, to produce a transduced immune cell culture; expanding the transduced immune cell culture; concentrating the expanded immune cell culture of (c); and harvesting the concentrated immune cell culture of (d) to produce a genetically modified immune cell culture, wherein (a) through (e) are performed by a fully enclosed, automated cell engineering system.

In additional embodiments, provided herein is a method for automated production of a genetically modified immune cell culture, the method comprising: activating an immune cell culture with an activation reagent to produce an activated immune cell culture; transducing the activated immune cell culture with a vector, to produce a transduced immune cell culture; expanding the transduced immune cell culture; concentrating the expanded immune cell culture of (c); and harvesting the concentrated immune cell culture of (d) to produce a genetically modified immune cell culture, wherein (a) through (e) are performed by a fully enclosed, automated cell engineering system, and wherein each of (a) through (e) are performed with immune cell cultures having an optimized cell density (cells/mL) and an optimized cell confluency (cells/cm$^2$).

In additional embodiments, provided herein is a method for automated production of a genetically modified immune cell culture, the method comprising: activating an immune cell culture with an activation reagent to produce an activated immune cell culture; transducing the activated immune cell culture with a vector, to produce a transduced immune cell culture; expanding the transduced immune cell culture, wherein the transduced cell culture is not shaken during the expanding; concentrating the expanded immune cell culture of (c); and harvesting the concentrated immune cell culture of (d) to produce a genetically modified immune cell culture, wherein (a) through (e) are performed by a fully enclosed, automated cell engineering system.

In still further embodiments, provided herein is a method for automated production of a genetically modified immune cell culture, the method performed by a cell engineering system, comprising: activating an immune cell culture with an activation reagent to produce an activated immune cell culture in a first chamber of the cell engineering system; transducing the activated immune cell culture, the transducing comprising: transferring the activated immune cell culture from the first chamber to an electroporation unit; electroporating the activated immune cell culture with a vector, to produce a transduced immune cell culture; transferring the transduced immune cell culture to a second chamber of the cell engineering system; expanding the transduced immune cell culture; concentrating the expanded immune cell culture of (c); and harvesting the concentrated immune cell culture of (d) to produce a genetically modified cell culture.

In additional embodiments, provided herein is a cassette for use in an automated cell engineering system, comprising: a low temperature chamber, for storage of a cell culture media; a high temperature chamber for carrying out activation, transduction and expansion of an immune cell culture, wherein the high temperature chamber is separated from the low temperature chamber, by a thermal barrier, the high temperature chamber including a cell culture chamber; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber.

In still further embodiments, provided herein is a cassette for use in an automated cell engineering system, comprising: a cell culture chamber for carrying out activation, transduction and/or expansion of an immune cell culture having a chamber volume that is configured to house an immune cell culture, a satellite volume for increasing the working volume of the chamber by providing additional volume for media and other working fluids without housing the immune cell culture, wherein the satellite volume is fluidly connected to the cell culture chamber via one or more fluidics pathways such that media is exchanged with the culture chamber without disturbing the immune cell culture.

BRIEF DESCRIPTION OF THE FIGURES

FIG. 6A shows a COCOON™ system in the closed configuration. FIG. 6B shows a Cassette that can be inserted into the COCOON™. FIG. 6C shows a COCOON™ system in the open configuration.

FIG. 6F shows a more detailed view of the cell culture chamber utilized in a COCOON™ system.

FIGS. 7A-7C show results of experiments described in Example 1, comparing GFP transduction in the COCOON™ system and manual manipulation. FIG. 7A shows a comparison of average harvest yields. FIG. 7B shows a comparison of average harvest viability. FIG. 7C shows a comparison of average transduction efficiency.

FIG. 8A shows a comparison of the viable cell yield. FIG. 8B shows a comparison of viability and transduction efficiency.

FIG. 9A shows a comparison of relative CAR T purity. FIG. 9B shows a comparison of CD8+ cell percentage. FIGS. 9C and 9D show production of TNFα and INFγ, respectively.

FIGS. 10A-10B show results of experiments described in Example 1, comparing the killing of target tumor cells by CAR T cells cultured in the COCOON™ system (FIG. 10A) and the PERMALIFE™ bag (FIG. 10B).

FIG. 11A shows a disposable T cell cassette that can be loaded into the COCOON™ system. FIG. 11B shows a COCOON™ system in the open configuration. FIG. 11C shows the cassette loaded into the COCOON™. FIG. 11D shows the COCOON™ in a closed configuration. FIG. 11E shows a detailed view of a cassette for use with the COCOON™.

FIG. 13A compares viable cell yield. FIG. 13B compares population doubling level (PDL). FIG. 13C compares viable CD3+ T cell yield. FIG. 13D compares CD3+ cells PDL. FIG. 13E compares percentage of CD3+ subsets (CD4+ and CD8+). FIG. 13F compares cell exhaustion as measured by anti-PD-1. FIGS. 13G and 13H show cytometry plots of CD8+CD3+ T cells activated with DYNABEAD(S)™ or OKT3, respectively.

FIG. 14A compares transduction efficiency of CD3+ cells. FIG. 14B compares total number of viable CAR T cells. FIG. 14C compares transduction efficiency of T cell subsets (CD4+ and CD8+). FIG. 14D compares total CAR T cells by subsets. FIGS. 14E and 14F show cytometry plots of CD3+ OKT3 activated cells in COCOON™ and PERMALIFE™ bags, respectively.

FIG. 15A compares percentage of cells producing TNFα. FIG. 15B compares percentage of cells producing IFNγ. FIGS. 15C and 15D show cytometry plots of DYNABEAD(S)™-activated COCOON™-produced cells secreting TNFα and IFNγ, respectively. FIGS. 15E and 15F show tumor killing efficiency of CAR T cells produced from PERMALIFE™ bags or COCOON™ system, respectively.

FIG. 16 shows a summary of the comparison between COCOON™ and PERMALIFE™, and activation by DYNABEAD(S)™ or OKT3.

FIG. 22 shows further evidence of differentiation of cell phenotype.

DETAILED DESCRIPTION OF THE INVENTION

The present disclosure provides an automated method of producing chimeric antigen receptor T (CAR T) cells. The production of CAR T cells typically requires manual involvement due to the patient-specific product. Automation of CAR T cell culture has been particularly challenging due to the multiple sensitive unit operations, including cell activation, transduction, and expansion. Thus, disclosed herein are automated methods of CAR T cell production utilizing a fully-enclosed cell engineering system.

Automated Cell Processing

For autologous cell treatments such as T cell therapy, the need for cost effectiveness, process efficiency, and product consistency is particularly acute, as manufacturing micro-lot (one patient per lot) batches lacks the economies of scale that allogeneic (multiple patients per lot) processes can exploit (see, e.g., Jones 2012; Trainor 2014). The larger and more localized workforce and facilities required for micro-lots places considerable demands on logistics, GMP compliance for manual production, especially with respect to availability and training of staff. In addition, the potential for variability in technique between operators can pose an undesirable risk to consistently meeting release criteria and ensuring a safe and dependable product.

As described herein, installation and comprehensive validation of automated manufacturing provides a solution to these logistical and operational challenges. An important approach to introducing automation to a production process is identifying the key modular steps where the operator applies a physical or chemical change to the production material, termed "unit operations." In the case of cell manufacturing, this includes steps such as cell separation, genetic manipulation, proliferation, washing, concentration, and cell harvesting. Manufacturers often identify focal process bottlenecks as the immediate opportunities for introducing automation. This is reflected in the technical operation spectrum of the majority of commercially available bioreactors, which tend to focus on discrete process steps. Process challenges in cell manufacturing (from sterility maintenance to sample tracking) are addressed herein by end-to-end automation that generates consistent cellular outputs while ameliorating inevitable process variability. The methods described herein also provide simplification, and the associated electronic records aid in complying with GMP standards (see, e.g., Trainor 2014).

Automation of Unit Operations and Key Process Sensitivities

The recent rapid progress of the clinical development of modified autologous T cells for cancer immunotherapy has led to planning for the associated translation and scale up/out implications.

Figure 1:
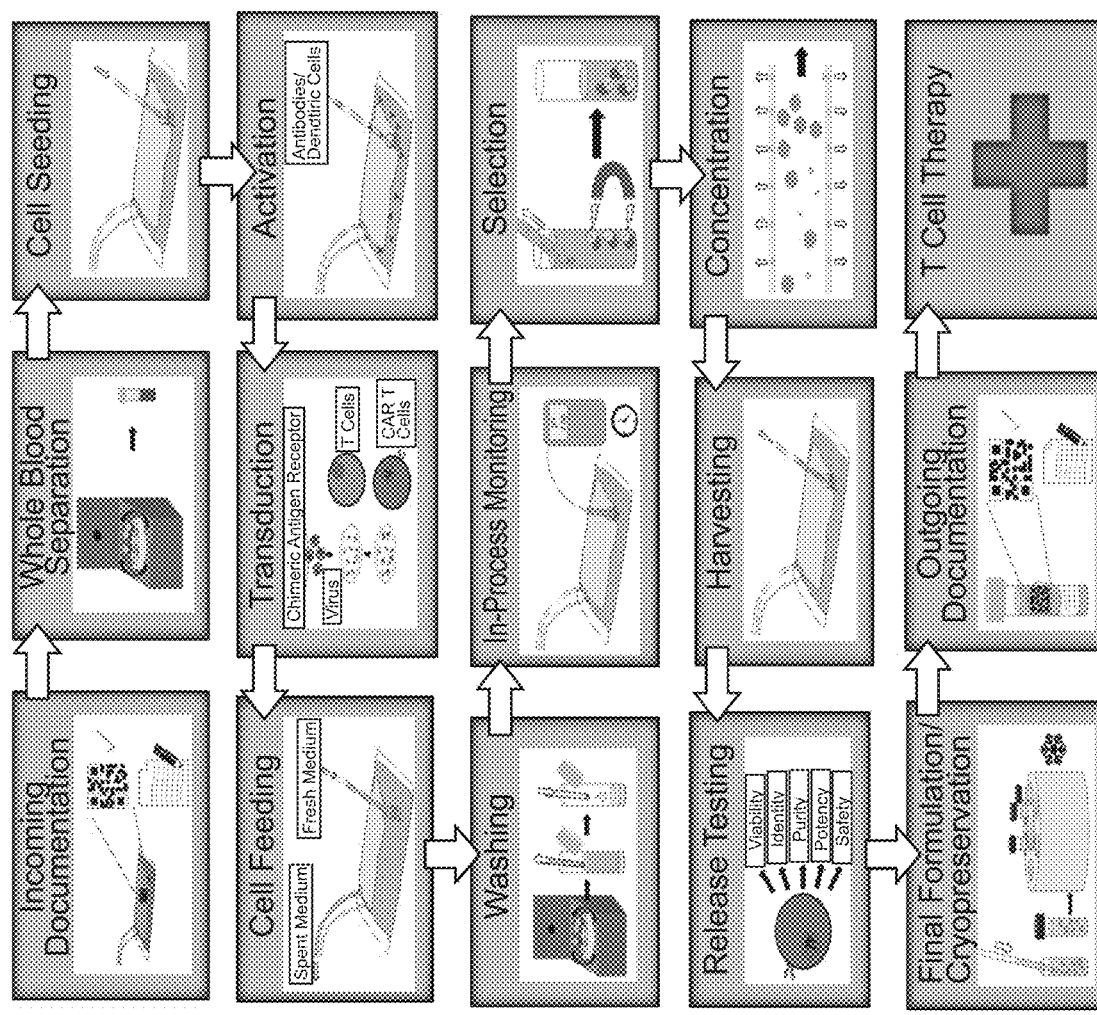
FIG. 1 shows a generalized manufacturing process for chimeric antigen receptor (CAR) T cells.

While specific protocols may vary for T cell manufacturing, a generalized chimeric antigen receptor T cell (CAR T) process is illustrated in FIG. 1. FIG. 1 describes unit operations of CAR T cell manufacturing, from initial processing of a patient blood sample to formulating output cells for autologous T cell therapy.

As described herein, to achieve cell manufacturing automation, the methods described herein provide for understanding the status of the cells at each transition point and how they are impacted by the specific unit operation. The micro-lot production for patient-specific therapies should be respectful of key process sensitivities that impact the feasibility of automation. Automation described herein successfully embraces various process steps.

Table 1 below highlights the challenges of some process steps identified for T cell automation and notes the impact of the sensitivity on the automation strategy. Note that for all unit operations, open transfer of cells between respective equipment is a key sensitivity due to the risk of contamination.

TABLE 1

| Automation Challenges and Benefits | | |
| --- | --- | --- |
| Unit Operation | Challenges of Key Process Steps | Benefit of Automating |
| Fractionation | Highly variable based on donor cells and operator technique (see e.g., Nilsson 2008) Residual impurities can impact performance | High purity of target starting population More consistent and improved product |
| Cell Seeding | Inhomogeneous cell distribution leads to variability in growth rates | Homogenous automated seeding strategy can improve consistency and potency |
| Activation | Stable contact between cells and activation reagent Uniform activation - homogeneous distribution | Automated loading can ensure reproducibly homogeneous distribution and activation which can be difficult to consistently achieve with manual methods |

TABLE 1-continued

Automation Challenges and Benefits

| Unit Operation | Challenges of Key Process Steps | Benefit of Automating |
|---|---|---|
| Transduction | Efficiency can be affected by the degree of cell-virus mixing, which may vary based on operator handling Increased exposure time may have negative impact on cells | Volume reduction prior to virus addition enables high degree of cell-virus contact Time-based operation enables cell transfer regardless of time of day Closed system decreases risk to operator |
| Electroporation | Efficiency can vary based on operator mixing, washing and concentration technique | Standardized protocols ensure consistent results when upstream and downstream steps are integrated |
| Feeding | Timing of media exchange needs to consider nutritional requirements based on cell growth (see, e.g., Bohenkamp 2002), and the component stability at 37° C. | Biofeedback can optimize feeding schedule (see, e.g., Lu 2013) and minimize media use Components can be stored at refrigerated temperatures to prolong stability and automatically pre-warmed before use |
| Selection | Extensive handling steps can result in cell loss Operator variability | Full automation improves consistency |
| Harvest | Acellular materials (such as cell separation beads) to be removed prior to final formulation (see e.g., Hollyman 2009) Manual pipetting variability can impact final yield | Cells automatically transferred from culture vessel regardless of time of day Improved final yield consistency over manual pipetting |
| Washing | Aggressive washing may induce shear stress or cause cell loss during supernatant removal | Gentle washing, filtration, or sedimentation without moving the culture vessels, can be utilized to reduce cell loss and remove residuals |
| Concentration | Cell recovery may vary by operator during aspiration | Automated volume reduction reduces operator variability Filtration methods also minimize cell loss |
| Formulation | Product must be well mixed Small working volumes magnify impact of volume inaccuracies Viability decreases with longer exposure times to cryopreservative | Automated mixing ensures homogenous distribution of cells in final formulation Automated volume addition removes risk of manual pipetting error or variability Increased automation reduces variability in temperature sensitive steps |

Tailoring the automation of a manual process around the sensitivities listed in Table 1 can support successful translation, maintenance or improvement on the performance of the cell therapy.

Integration of Automated Unit Operations

Along with considering the GMP logistics, economics and patient safety implications of automation, unit operations can be assessed in the context of typical labor hours per unit operation (including working hours for both the operator and the quality assurance monitor). Table 2 identifies nominal manual processing timelines for representative steps in CAR T automation. This table highlights the resource commitments required for each unit operation in a generalized CAR T cell process. For each step, the estimated remaining labor time for an automated process is identified, as well as the rationale for the reduction.

TABLE 2

Automation Reduction of Labor Hours

| Unit Operation | Manual Labor | Automated Labor | Labor Reduction |
|---|---|---|---|
| Incoming Documentation | 2 hours | 0.5 hours | Identification, sample tracking details and operation log all initiated by uniform labelling and corresponding software |

TABLE 2-continued

Automation Reduction of Labor Hours

| Unit Operation | Manual Labor | Automated Labor | Labor Reduction |
|---|---|---|---|
| Reagent Preparation | 4 hours | 2 hours | Single reagent preparation step with storage in a refrigerated zone removes need to prepare reagents before each unit operation |
| Isolation from whole blood | 3 hours | 0.5 hours | Once blood sample is loaded, automated PBMC isolation from whole blood possible using centrifugation (see, e.g., FDA 2011), filtration (see, e.g., Wegener 2014) and/or antibody selection |
| Cell Seeding | 1 hour | 0 hours | Automated seeding immediately after fractionation |
| Activation | 2 hours | 0 hours | T cell activation by common methods such as antibodies or beads performed by automated mixing of reagents with cell culture (see, e.g., Trickett 2003) Activation by dendritic cell co-culture would invoke the same automated culture principles (see, e.g., Hasegawa 2006) |
| Transduction | 6 hours | 2 hours | T cells automatically transferred to a transduction chamber (with optional coating if viral vectors used) Manual interaction required to attach viral vectors if not stable in refrigerated conditions |
| Electroporation | 2 hours | 0 hours | Integrated electroporation removes the need for additional preparation steps |
| Cell Feeding | 13.5 hours | 0 hours | Media removal and feeding automated |
| Washing | 1 hour | 0 hours | Automated and integrated gentle cell washing Cell concentration by filtration reduces time spent washing compared with centrifugation |
| In-Process Documentation/ Monitoring | 2 hours | 1 hours | Biosensor monitoring (e.g. pH, oxygen, glucose) Responses to process readouts pre-programmed; potentially averting emergencies Application of imaging technology to processes such as fluid monitoring (see, e.g., Odeleye 2014) and cell counting (see, e.g., Grishagin) being developed for automated processes |
| Selection | 2 hours | 0 hours | Automated mixing of cells and selection reagents Magnetic cell sorting performed by binding antibody-conjugated beads to cells and passing them through a magnetized chamber |
| Concentration | 2 hours | 0 hours | Cell centrifugation or filtration all automated |
| Harvest | 2 hours | 0 hours | T cells automatically harvested by agitation, fluid flow and washing |
| Release Testing | 9 hours | 7 hours | Biomass or capacitance detection indicate relative abundance of cells Automated cell counters, flow cytometers, and other analysis equipment reduce manual counting time Phenotypic and functional assays still likely require manual labor |
| Final Formulation or Cryopreservation | 2 hours | 1 hour | Cell concentration and mixing with formulation solution automated Notifications to operator required for quick transfer to controlled rate freeze if not being shipped |
| Outgoing Tracking and Documentation | 4 hours | 2 hours | Identification, sample tracking details and operation log all generated by software for labelling and delivery to patient |
| Total Labor | 57.5 hours | 16 hours | Automation can lead to a 72% reduction in labor time |

Based on the methods described herein, the automation of unit operations can reduce a nominal manual process by nearly 40 hours to approximately a quarter of the original time.

Discrete Versus Fully Integrated Automation

While there is compelling evidence for the value of automation (see, e.g., Trainor 2014; Levine 2017), there needs to be a subsequent analysis on the value and practicality of integrating these automation steps in an end-to end sequence with automated transfers. There are different perspectives on the advantages of discrete process automation versus the advantages of end-to-end integration.

The key benefit to discrete automation is flexibility. This relates to the areas of:
1) Maintenance of unique process operations
2) Acceleration of translational activities based on individual unit operation validation
3) Ability to modify processing steps to accommodate donor-to-donor variability The first point related to increased flexibility provides the operator with more control of the process. This is important in circumstances where the process has highly sensitive steps that can impact the final product. Switching to an all-in-one system may impose constraints that influence the product outcome. A discrete approach provides the flexibility to choose how to perform each step, which may be particularly important with highly sensitive unit operations. The discrete approach also allows gradual translation into automation from manual processing, which helps to demonstrate equivalency if each unit operation can be tested independently. Additionally, automating specific unit operations provides the flexibility for decisions to be made based on the cell performance. For example, if cells are growing rapidly, there may be the need to expand from one cell culture bag to two. Lastly, the approach to automation using discrete systems also enables groups to pick-and-choose which equipment to use for each unit operation.

Equipment utilization is another argument for discrete automation. There may be some unit operations that require significantly more time than others. An end-to-end processing system requires all multiple unit operations to run on a single system, thus occupying the equipment for the duration of the culture process.

While there are benefits to discrete automation, an end-to-end approach offers different, though no less compelling benefits. Firstly, a fully integrated system greatly reduces the risk of contamination. As there is increased handling required with a discrete approach, there is a greater chance of product variability due to operator interventions. Secondly, and as previously mentioned, this inevitably leads to higher labor costs.

The flexibility provided by the discrete approach is important. In situations where the process is important in defining the product, an end-to-end system should have the flexibility to integrate unique sensitivities. This may include certain feeding strategies, oxygen levels, surface treatments, and so forth. Such an approach requires flexibility in both the software and the disposable component. The system should provide the option to pull cell and media samples at various points in the process to confirm that specific unit operations meet product specification checkpoints. If modifications need to be made, the software should be able to implement these changes to provide ideal conditions. While easy-to-use and flexible software is highly beneficial for translational purposes, it is important that the software can be easily locked down to comply with clinical standards (FDA 21 CFR Part 11). Once locked down, there should be limited if any ability for the operator to change the protocol. However, to address issues with inherent donor-variability, there should be the option to select from a range of validated protocols based on cell growth rates. For example, if the cells are growing rapidly, the system should be able to respond to this and adjust the feed or harvest time points, accordingly.

Figure 2:
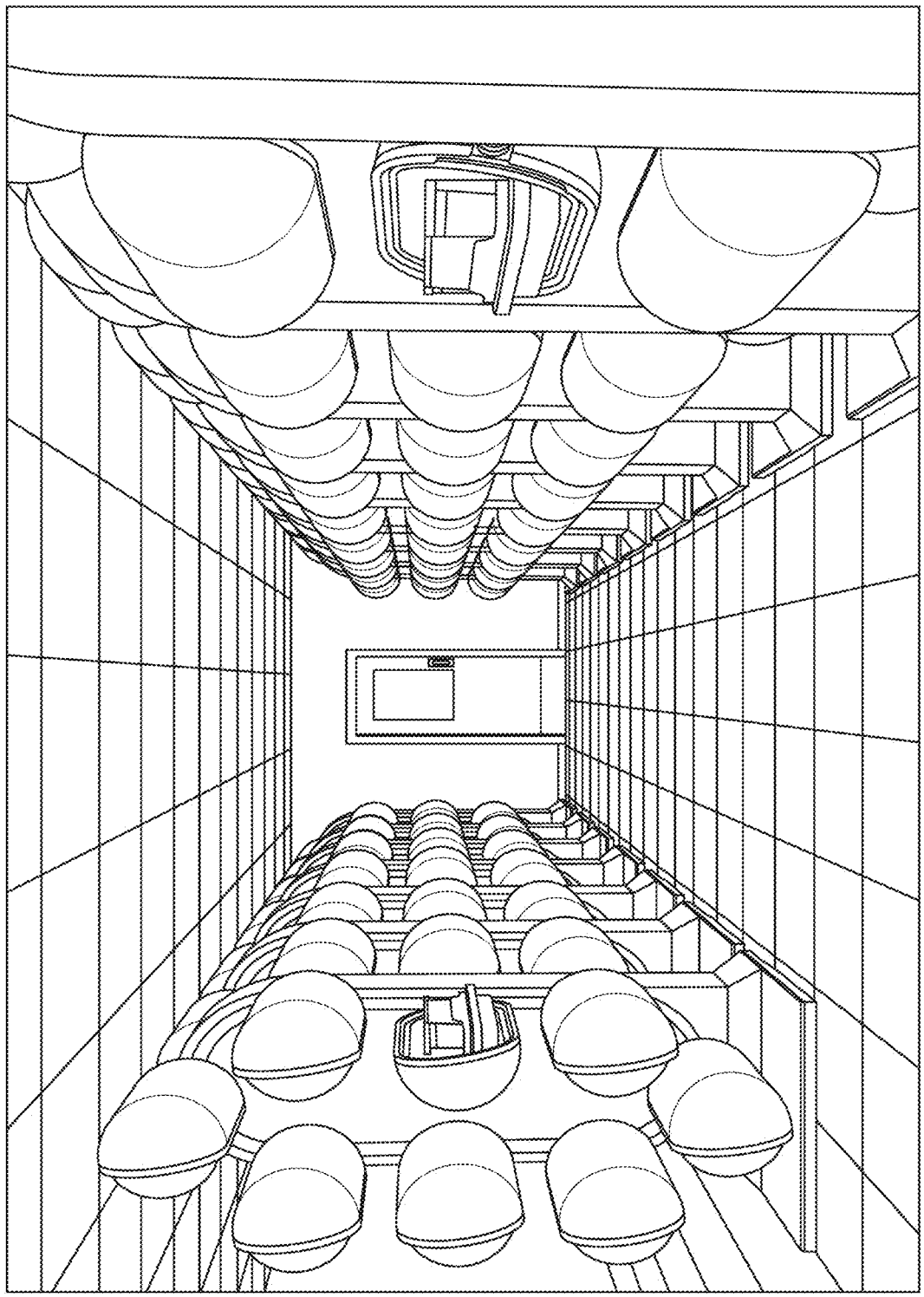
FIG. 2 shows a lab space containing exemplary cell engineering systems as described in embodiments herein.

The selection of end-to-end integration versus discrete automation is also dependent upon the long-range vision for the clinical process. A single all-in-one system can offer significantly greater space efficiency to minimize the required footprint in expensive GMP clean rooms. For example, as shown in FIG. 2, fully integrated automated systems are designed to maximize required footprint to reduce expensive GMP clean room space. FIG. 2 shows 96 patient-specific end-to-end units running in a standard lab space.

A single system also provides greater ease of data tracking, whereas discrete systems may not offer compliant software that links together all electronic data files. Software platforms such as VINETI® (Vineti Ltd) and TRAKCEL (TrakCel Ltd) allow electronic monitoring and organization of supply chain logistics. However, single all-in-one culture systems can go further still by incorporating a history of both processing events and biomonitoring culture conditions associated with each unit operation into a batch record. Accordingly, the benefits of end-to-end integration offer a significant competitive advantage.

Commercial Platforms for Integration of Unit Operations

Clinical trial success in a number of autologous cell therapies, especially immunotherapy for blood-based cancers, has highlighted the importance of enabling translation of new clinical protocols to robust production platforms to meet projected clinical demand (see, e.g., Levine 2017; Locke 2017). For autologous therapies, processing each patient-specific cell treatment suitably utilizes comprehensive manufacturing activities and operations management. The methods herein link unit operations in a turnkey automated system to achieve process optimization, security and economy.

The challenge in designing an autologous process is two-fold. Firstly, unlike allogeneic manufacturing in which separate processing steps can occur in physically separate and optimized pieces of equipment, scaled-out autologous platforms suitably perform all of the necessary steps in a single closed, self-contained automated environment. Secondly, unlike an allogeneic process in which every run theoretically starts with a high-quality vial from a cell bank, with known quality and predictable process behavior, the starting material in an autologous process is highly variable, and generally comes from individuals with compromised health.

Thus, provided herein are methods that are able to sense culture conditions and respond accordingly as a sophisticated bioreactor, by controlling factors such as physical agitation, pH, feeding, and gas handling. Furthermore, there are significantly different challenges with technology transfer related to autologous treatments compared to allogeneic treatments. Autologous products may have greater restrictions on stability between the manufacturing process and the patient treatment. Sites can be located globally rather than at a single center. Having a locked down (e.g., fully enclosed) all-in-one system significantly improves the technology transfer process between sites.

While source variability cannot be eliminated, automation helps to remove variability of the final autologous product through standardization and reproducibility. This practice is adopted by leading cell system providers to obtain a cell performance reference point via biosensors that monitor the status of the active cell cultures. In end-to-end integration, output from any specific stage in the process should be within acceptable parameters for the onward progression of the process.

As described herein, in embodiments, the methods provided utilize the COCOON™ platform (Octane Biotech (Kingston, ON)), which integrates multiple unit operations in a single turnkey platform. Multiple cell protocols are provided with very specific cell processing objectives. To provide efficient and effective automation translation, the methods described utilize the concept of application-specific/sponsor-specific disposable cassettes that combine multiple unit operations—all focused on the core requirements of the final cell therapy product.

Figure 3:
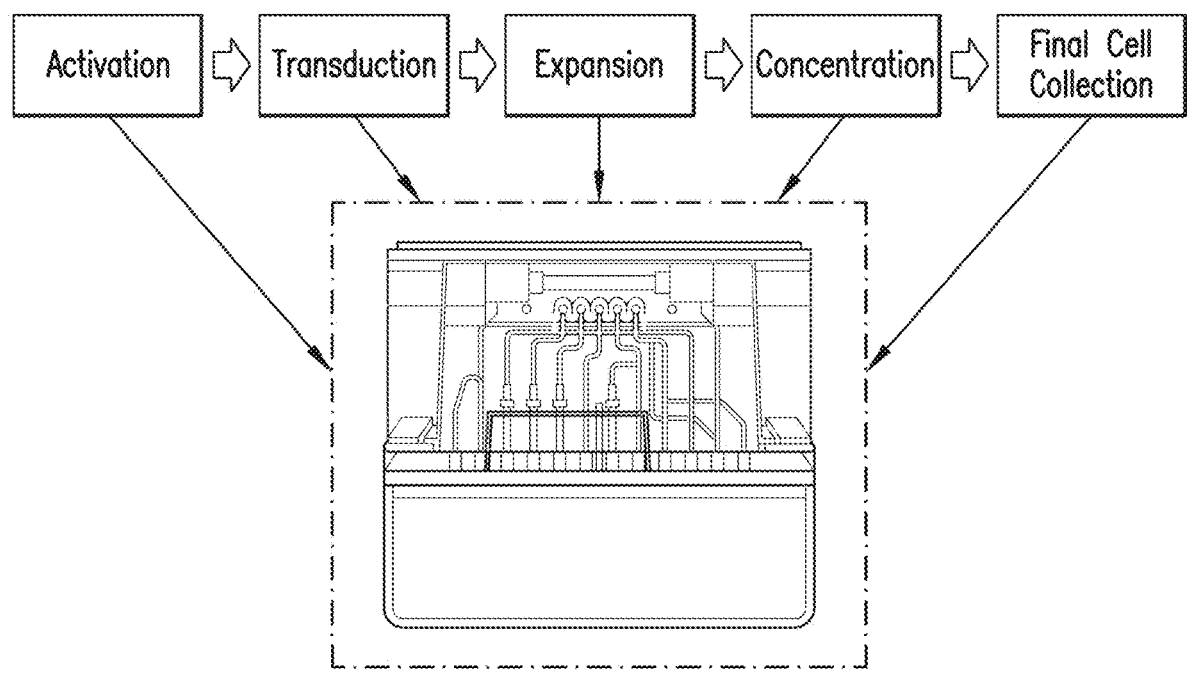
FIG. 3 shows a CAR T cell production process that can be performed in a cell engineering system as described in embodiments herein.

The methods described herein have been used to expand CAR T cells (including activation, viral transduction and expansion, concentration and washing) in a fully-integrated closed automation system (FIG. 3).

Figure 4:
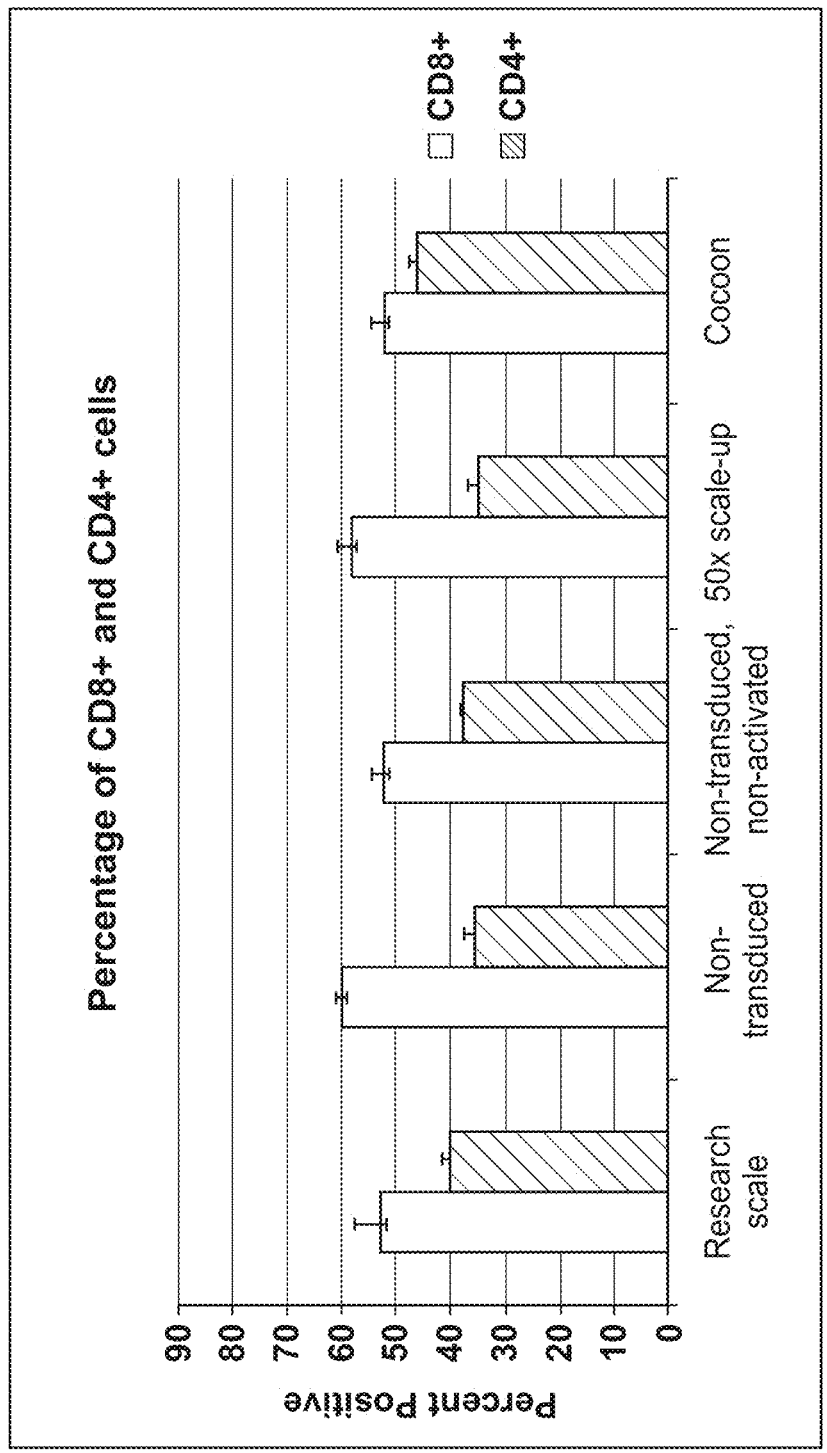
FIG. 4 shows comparisons between the COCOON™ system and control methods for maintaining populations of CD8+ and CD4+ cells.
Figure 5:
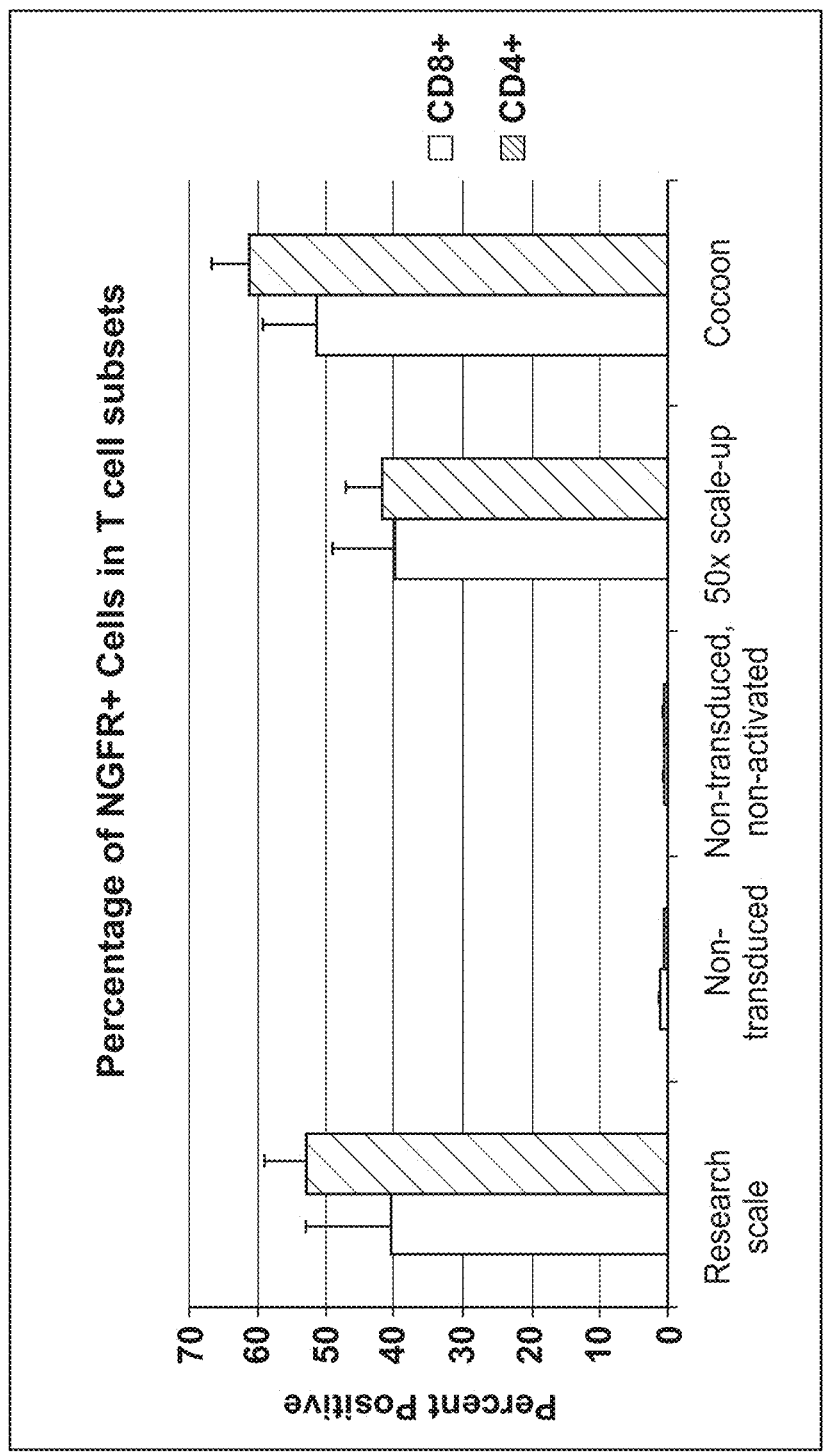
FIG. 5 shows comparisons between the COCOON™ system and control methods for amount of CAR T cells in the CD8+ and CD4+ cell populations.

In the experiments conducted, the fold expansion of CART cells, in 10-14 day cultures, reached around 40 to 60. Both CD4+ and CD8+ T cell subsets are required for successful CAR T therapy. Therefore, the runs and associated controls were evaluated via flow cytometry for their ability to maintain cultures of both T cell subsets. FIG. 4 shows that all runs as well as all controls were able to maintain both T cell subsets. The percentage of CAR T cells present was also evaluated in each population of T cell subset (FIG. 5). In all samples, there was a higher detection of NGFR (indicative of CAR construct) in the CD4+ fraction compared to the CD8+ fraction although in all samples, the NGFR+ fraction in the CD8+ portion was >50% of the fraction found in the paired CD4+ population. In summary, automated CAR T process using the methods described herein yields healthy populations of T cell subsets.

Advantages of Automation

Automation of unit operations in cell therapy production provides the opportunity for universal benefits across allogeneic and autologous cell therapy applications. In the unique scenario of patient-specific, autologous cell products, and ever more emphasized by the recent clinical success of these therapies, the advantages of automation are particularly compelling due to the significant micro-lot complexities of small batch GMP compliance, economics, patient traceability and early identification of process deviations. The associated emergence of complex manufacturing protocols draws attention to the fact that the value of end-to-end integration of automated unit operations in micro-lot cell production has not been a point of significant study. However, the expected demand for these therapies following their impending approval indicates that implementation of a fully closed end-to-end system can provide a much needed solution to manufacturing bottlenecks, such as hands-on-time and footprint.

Developers of Advanced Therapies are encouraged to consider automation early in the rollout of clinical translation and scale up of clinical trial protocols. Early automation can influence protocol development, avoid the need for comparability studies if switching from a manual process to an automated process at a later stage, and provide a greater understanding of the longer-term commercialization route.

Methods of Producing Genetically Modified Immune Cells, Including CAR T Cells

In embodiments, provided herein is a method for automated production of a genetically modified immune cell culture. As used herein a "genetically modified immune cell culture" (or genetically modified immune cells) refers to cells of the immune system that are modified or primed (e.g., through co-culture with antigen presenting cells), resulting in cells that have a desired phenotype useful in treating, preventing or ameliorating one or more diseases in an animal, including a human. As used herein an "immune cell culture" refers to a collection of cells prepared by a method described herein, and can include a cell population for use in research or clinical trials, as well as for administration to a mammal, including a human patient, for a medical therapy. The genetically modified immune cell cultures that can be produced using the methods described herein can include mast cells, dendritic cells, naturally killer cells, B cell, T cells, etc.

The various methods described herein can also be extended to other genetically modified cell cultures, including for example, the generation of genetically modified human stem cell cultures, including hematopoietic stem cells.

In exemplary embodiments, the method comprises activating an immune cell culture with an activation reagent to produce an activated immune cell culture, transducing the activated immune cell culture with a vector, to produce a transduced immune cell culture, expanding the transduced immune cell culture, concentrating the expanded immune cell culture and harvesting the concentrated immune cell culture to produce a genetically modified immune cell culture. Suitably, the method further includes either or both the expanded immune cell culture and the concentrated immune cell culture. In embodiments, the various steps of the method are performed by a fully enclosed cell engineering system and are optimized via a process to produce the genetically modified immune cell culture.

Methods for optimizing the process for producing the genetically modified immune cells include optimization of cell culture conditions before beginning an automated method, as well as the use of feedback from various sensors, etc., to assist with real-time modifications to growth conditions (e.g., gas concentration, media conditions, temperature, pH, waste and nutrient concentrations, etc.).

In embodiments, the optimizing process is a self-adjusting process, that is one that does not require input from an external (human) user, and is able via various computer programs and conditions to determine the required modifications to a cell culture or other characteristics to optimize the automated process. In embodiments, the self-adjusting process includes monitoring with one or more of a temperature sensor, a pH sensor, a glucose sensor, an oxygen sensor, a carbon dioxide sensor, and an optical density sensor. As described herein, the use of these various sensors in the fully enclosed cell engineering system occurs at various times and locations within the system, and work together in concert to provide the optimization. For example, the self-adjusting process can adjust (e.g., raise or lower) one or more of a temperature, a pH level, a glucose level, an oxygen level, a carbon dioxide level, and an optical density of the transduced T cell culture, based on the monitoring.

The optimization process can also be based on the unique characteristics of the starting cell population, including for example, the total cell number, the source of the cells, the density of the cells, the age of the cells, etc. These starting cell population characteristics can be input into a computer control system prior to beginning the automated methods, upon which the system will make various initial modifications to optimize the methods, e.g., oxygen and carbon dioxide concentration, flow rates, incubation times, pH, etc. Alternately, the monitoring of cell processes enables the automated characterization of the progress of the cell culture sequence from the starting population to enable case-by-case adjustment of conditions for optimized final cell culture properties.

In exemplary embodiments, the methods described herein produce at least about 50 million viable genetically modified immune cells. In suitable embodiments, the methods described produce at least about 100 million viable genetically modified immune cells, or at least about 200 million cells, at least about 300 million cells, at least about 400 million cells, at least about 500 million cells, at least about 600 million cells, at least about 700 million cells, at least about 800 million cells, at least about 1 billion cells, at least about 1.1 billion cells, at least about 1.2 billion cells, at least about 1.3 billion cells, at least about 1.4 billion cells, at least about 1.5 billion cells, at least about 1.6 billion cells, at least about 1.7 billion cells, at least about 1.8 billion cells, at least about 1.9 billion cells, at least about 2 billion cells, least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, or at least about 3.0 billion genetically modified immune cells.

As described herein, the genetically modified immune cell culture produced by the methods is suitably a T cell culture, including a chimeric antigen receptor T (CAR T) cell culture. In such embodiments, the vector utilized to produce such CAR T cells is a vector encoding a chimeric antigen receptor. Suitably the immune cell culture comprises peripheral blood mononuclear cells and/or purified T cells. In embodiments, the immune cell culture comprises at least one accessory cell, suitably a monocyte or a monocyte-derived cell. As described herein, in embodiments, the accessory cell comprises antigens for a T cell receptor, including CD28, CD40, CD2, CD40L and/or ICOS.

Suitably, the activation reagent comprises an antibody or a dendritic cell. In embodiments, the antibody is immobilized on a surface, which can include an polystyrene plastic, silicone or other surface, including for example, the surface of a bead.

In other embodiments, the activation reagent comprises an antibody that is a soluble antibody, including at least one of an anti-CD3 antibody and an anti-CD28 antibody. Exemplary antibodies include OKT3.

Various methods for transducing the cells can be utilized in the automated methods, including for example, viral infection, electroporation, membrane disruption, or combinations thereof.

In exemplary embodiments, the vector that is utilized in the methods is a lentiviral vector or a retrovirus. Suitably, the transducing comprises mixing the vector in cell culture media and delivering the vector in the media uniformly to the activated immune cell culture. As described herein, the uniform delivery of the vector in a homogenous manner to the cells provides for optimization of the various cell characteristics of high output of desired genetically modified immune cells.

As described herein, the methods of expanding the cells suitably include at least one or more of feeding, washing, monitoring, and selecting of the transduced immune cell culture.

The various methods described herein are conducted in a manner such that the oxygen level of the transduced immune cell culture is optimized for the immune cell culture. This optimization allows for production of a large number of viable cells having the desired phenotypic characteristics, including, as described herein, the promoting of a desired cell phenotype. In embodiments, oxygen level or concentration is optimized by the cell engineering system recirculating cell culture media through an oxygenation component during one or more of steps (a) to (e). As described herein, oxygenation suitably occurs through one or more fluidic pathways, including silicone-based tubing components.

In further embodiments, the cell engineering system recirculates nutrients, waste, released cytokines, and/or dissolved gasses during the various method processes. This recirculation helps aid in the production of a large number of viable cells having the desired phenotype(s). Suitably, the carbon dioxide level provided by the cell engineering system decreases during step the expansion step so as to optimize cell growth, etc. In other embodiments, the $CO_2$ level can be raised, for example, if a complete media exchange is utilized.

Other mechanisms for optimizing the growth conditions for the cells include modifying and controlling the flow rate of the media provided to the cells. As the cells begin to grow, the circulation rate of the media provided is increased, which improves gas exchange and allows oxygen and carbon dioxide to either enter or leave the cell culture, depending on the conditions of the cells and the requirements at the time.

In embodiments, the cell engineering system is configured to perform several rounds of one or more of feeding, washing and monitoring, and in embodiments, selecting of the transduced immune cell culture. These various activities can be performed in any order, and can be performed alone or in combination with another activity. In embodiments, concentrating of the cells comprises centrifugation, supernatant removal following sedimentation, or filtration. Suitably, the optimization process further includes adjusting parameters of the centrifugation or filtration, suitably in a self-adjusting process. Selecting of the transduced cells can be carried out by, for example, magnetic separation, filtration, adherence to a plastic or other substrate, etc.

In embodiments as described herein, the cell engineering system comprises a plurality of chambers, and wherein each of the steps of the method is performed in a different chamber of the plurality of chambers of the cell engineering system.

Suitably, the method further includes removing the activation reagent from the activated immune cell culture after step (a), and can include removing the vector following the transducing step. The activation reagent is suitably removed from the immune cell culture by washing, draining or physically removing the cells or the activation reagent. The vector can be removed by washing, or by binding the vector to a surface (e.g., a retronectin or fibronectin coated surface) and then transferring the cells to a different chamber.

In exemplary embodiments, the cell engineering system contains the cell culture, the activation reagent, the vector, and cell culture medium prior to starting the method. In other embodiments, the activation reagent and/or the vector can be added separately following the start of the method of production, or at any suitable time during the process.

In additional embodiments, provided herein is method for promoting a preferred phenotype of a genetically modified immune cell culture, the method comprising activating an immune cell culture with an activation reagent to produce an activated immune cell culture, wherein the activation reagent and activating conditions promote the phenotype of the genetically modified immune cell culture, transducing the activated immune cell culture with a vector, to produce a transduced immune cell culture, expanding the transduced immune cell culture, concentrating the expanded immune cell culture, and harvesting the concentrated immune cell culture of (d) to produce a genetically modified immune cell culture. As described herein, the methods are suitably performed by a fully enclosed, automated cell engineering system.

As described herein, selection of the appropriate activation reagent and the appropriate activation conditions provide for the promotion of a desired phenotype of a genetically modified immune cell culture. That is, the phenotype of the immune cell culture can be specifically selected and promoted, so that suitable a majority of the cells that are produced by the methods have the desired, preferred phenotype. In other embodiments, a desired ratio of one cell phenotype to another phenotype can be controlled and promoted, providing a desired, preferred phenotype balance.

As described herein, it has been found that through the use of activation reagents that are antibodies, and particularly soluble antibodies, the desired phenotype of a genetically modified immune cell can be promoted. Suitably, the antibodies that are utilized are at least one of an anti-CD3 antibody, an anti-CD28 antibody and an anti-CD2 antibody, including the soluble antibody OKT3.

In embodiments, the activating conditions provide a substantially undisturbed immune cell culture allowing for stable contact between the activation reagent and the immune cell culture. As described herein, it has been found that allowing the cells to activate under substantially undisturbed conditions, and via the use of a cell culture chamber that is flat and substantially non-flexible. This provides an environment where the cells can be homogenously contacted with the activation reagent, as well as interact with the necessary nutrients, dissolved gasses, etc., to achieve the desired and promoted phenotype.

The methods described herein can influence the characteristics of the final immune cell culture product by selecting an appropriate activation method to provide the preferred phenotype. For example, activation utilizing a bead-based process as described herein promotes a more balanced CD4:CD8 ratio, whereas use of a soluble anti-CD3 promotes a higher population of CD8 than CD4. Other levels of CD8 and CD4 can also be provided using the methods described herein. In exemplary embodiments, as described herein, the methods can be utilized to prepare CAR T cells. Suitably, the methods can be utilized to promote a phenotype of the CAR T cells that has a ratio of CD8+ cells to CD4+ of about 0.1:1 to about 10:1, including a ratio of CD8+ cells to CD4+ cells of about 0.5:1 to about 5:1, about 0.8: to about 3:1, or about 1:1, about 2:1, etc.

In additional embodiments, methods are provided for automated production of a genetically modified immune cell culture, the method comprising, activating an immune cell culture with an activation reagent to produce an activated immune cell culture, transducing the activated immune cell culture with a vector, to produce a transduced immune cell culture, expanding the transduced immune cell culture, concentrating the expanded immune cell culture of (c), and harvesting the concentrated immune cell culture of (d) to produce a genetically modified immune cell culture. As described herein, the method is suitably performed by a fully enclosed, automated cell engineering system. In embodiments, each of the steps of the method is performed with immune cell cultures having an optimized cell density (cells/mL) and an optimized cell confluency (cells/cm$^2$).

As described herein, it has been determined that utilizing an optimized cell density (cells per mL of cell media) and/or cell confluency (cells per area (cm$^2$) of a cell culture chamber on which the cells are being acted one and grown), provide for increased production of viable cells, as well as better control of cell phenotype, etc.

In embodiments, the optimized cell density for is about 0.05*10$^6$ cells/mL to about 60*10$^6$ cells/mL, about 0.05*10$^6$ cells/mL to about 40*10$^6$ cells/mL, or about 0.05*10$^6$ cells/mL to about 20*10$^6$ cells/mL. The optimized cell density can vary over the course of the methods of production, such that at each stage of the method (i.e., activating, transducing, expanding, concentrating), the cell density is controlled or manipulated to provide the best cell density for that particular step of the method. The cell density can be optimized by, for example, selection of the optimal starting cell density, increasing or decreasing oxygen and/or carbon dioxide concentration, regulating pH, temperature, nutrients, removal of waste, etc. Exemplary cell densities include about 0.05*10$^6$ cells/mL, about 0.08*10$^6$ cells/mL, about 1*10$^6$ cells/mL, about 5*10$^6$ cells/mL, about 10*10$^6$ cells/mL, about 20*10$^6$ cells/mL, about 30*10$^6$ cells/mL, about 40*10$^6$ cells/mL, about 50*10$^6$ cells/mL, or about 60*10$^6$ cells/m L, etc.

In embodiments, the optimized cell confluency for is about 0.1*10$^6$ cells/cm$^2$ to about 60*10$^6$ cells/cm$^2$, or about 0.1*10$^6$ cells/cm$^2$ to about 40*10$^6$ cells/cm$^2$, or about 0.1*10$^6$ cells/cm$^2$ to about 20*10$^6$ cells/cm$^2$. The optimized cell confluency can vary over the course of the methods of production, such that at each stage of the method (i.e., activating, transducing, expanding, concentrating), the cell confluency is controlled or manipulated to provide the best cell confluency for that particular step of the method. The cell confluency can be optimized by, for example, selection of the optimal starting cell confluency, material selection of the cell culture chamber, increasing or decreasing oxygen and/or carbon dioxide concentration, regulating pH, temperature, nutrients, removal of waste, etc. Exemplary cell confluency include about 0.1*10$^6$ cells/cm$^2$, about 0.5*10$^6$ cells/cm$^2$, about 1*10$^6$ cells/cm$^2$, about 0.5*10$^6$ cells/cm$^2$, about 10*10$^6$ cells/cm$^2$, about 20*10$^6$ cells/cm$^2$, about 30*10$^6$ cells/cm$^2$, about 40*10$^6$ cells/cm$^2$, about 50*10$^6$ cells/cm$^2$, or about 60*10$^6$ cells/cm$^2$, etc.

In embodiments, the methods include the recirculation of nutrients, waste, released cytokines, and/or dissolved gasses are homogenously provided to the cells having a density of about 0.05*10$^6$ cells/mL to about 20*10$^6$ cells/mL and a confluency of about 0.1*10$^6$ cells/cm$^2$ to about 20*10$^6$ cells/cm$^2$.

In further embodiments, methods for automated production of a genetically modified immune cell culture are provided, the method comprising activating an immune cell culture with an activation reagent to produce an activated immune cell culture, transducing the activated immune cell culture with a vector, to produce a transduced immune cell culture, expanding the transduced immune cell culture, wherein the transduced cell culture is not shaken during the expanding, concentrating the expanded immune cell culture, and harvesting the concentrated immune cell culture of to produce a genetically modified immune cell culture. As described herein, suitably the methods are performed by a fully enclosed, automated cell engineering system.

As described herein, it has been surprisingly found that allowing the cells to expand under conditions where they are not shaken (i.e., not rotated or shaken in order to cause the cells to flow over top of one another), the methods provide optimal cell characteristics, including high viable cell yield and desired phenotypes. It has been determined that a large, un-shaken cell culture chamber, can provide homogenous access of the cells to the necessary reagents, nutrients, gas exchange, etc., while removing cellular waste, without the requirement to shake or disturb the cells to achieve the desired outcome. In fact, as described herein, it has been found that such methods for the automated production of genetically modified immune cells produce higher numbers of viable cells, greater numbers/ratios of desired cells types, and more robust cellular characteristics, as compared to methods that utilize cellular shaking, for example, as described in Miltenyi et al., "Sample Processing System and Methods," U.S. Pat. No. 8,727,132.

Suitably, the expanding step of the methods include at least one or more of feeding, washing, monitoring, and selecting of the transduced immune cell culture, without shaking the immune cell culture.

Also provided herein are methods for automated production of a genetically modified immune cell culture, the method performed by a cell engineering system, comprising activating an immune cell culture with an activation reagent to produce an activated immune cell culture in a first chamber of the cell engineering system, transducing the activated immune cell culture. In exemplary methods, the transducing comprises transferring the activated immune cell culture from the first chamber to an electroporation unit, electroporating the activated immune cell culture with a vector, to produce a transduced immune cell culture, and transferring the transduced immune cell culture to a second chamber of the cell engineering system. The methods further include expanding the transduced immune cell culture, concentrating the expanded immune cell culture of, and harvesting the concentrated immune cell culture of (d) to produce a genetically modified cell culture.

Figure 17:
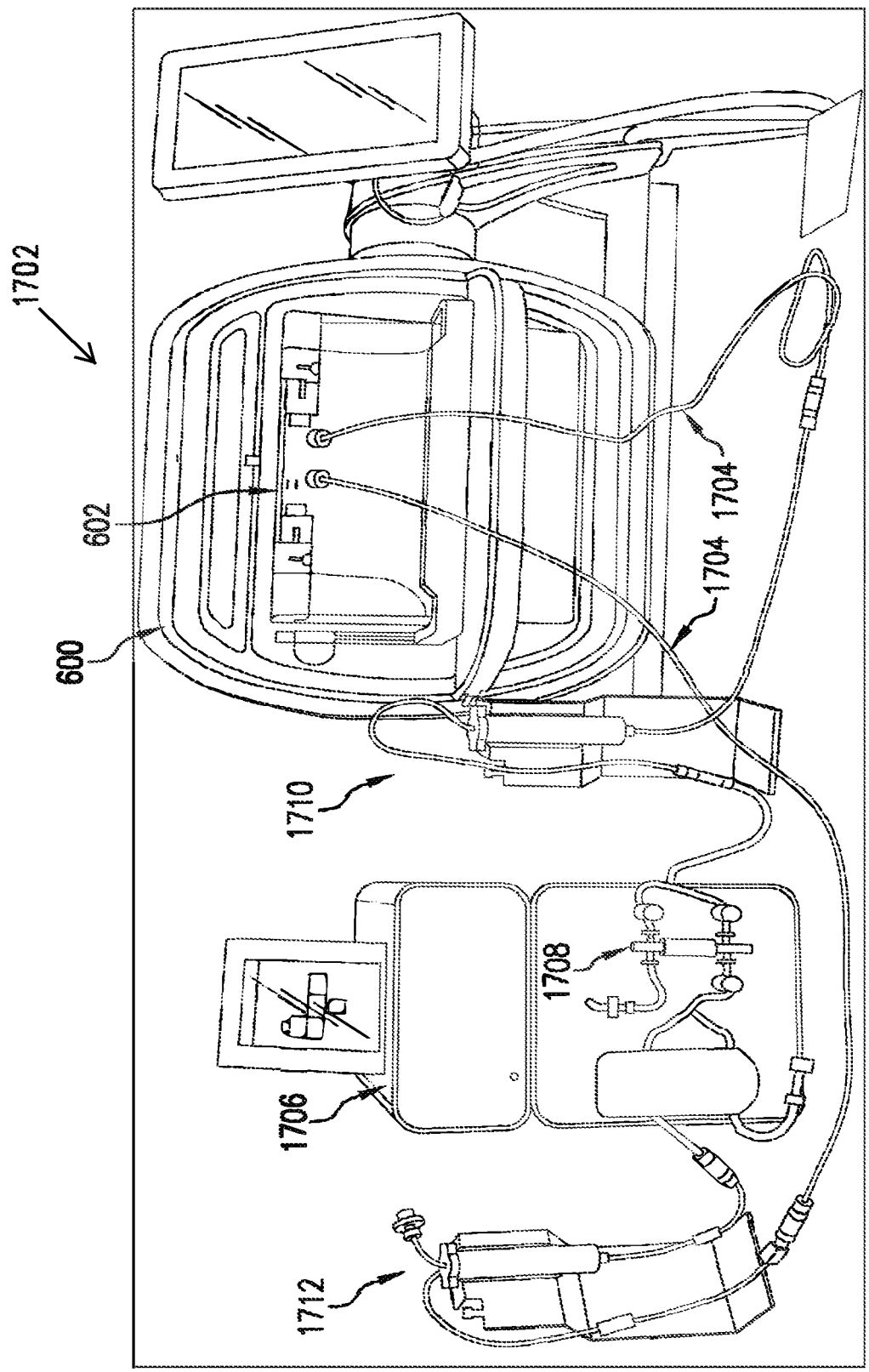
FIG. 17 shows the incorporation of an electroporation unit with a cell engineering system, in accordance with embodiments hereof.

For example, as shown in FIG. 17, an activated immune cell culture is transferred, e.g., via connection tubing 1704, from cassette 602 of a cell engineering system 600 to an electroporation unit 1706. Electroporation unit 1706 suitably includes an electroporation cartridge 1708, which holds the cell culture during the electroporation process. Following the electroporation process, the transduced immune cell culture is transferred back, via connection tubing 1704, to cell engineering system 600. FIG. 17 also shows the use of two optional reservoirs 1710 and 1712, which are used to hold the cell culture prior to and after electroporation, to help in the transfer between the cell engineering system and the electroporation unit as a result of different pump speeds, required pressures and flow rates. However, such reservoirs can be removed and the cell culture transferred directly from cell engineering system 1702 to electroporation unit 1706.

Figure 18:
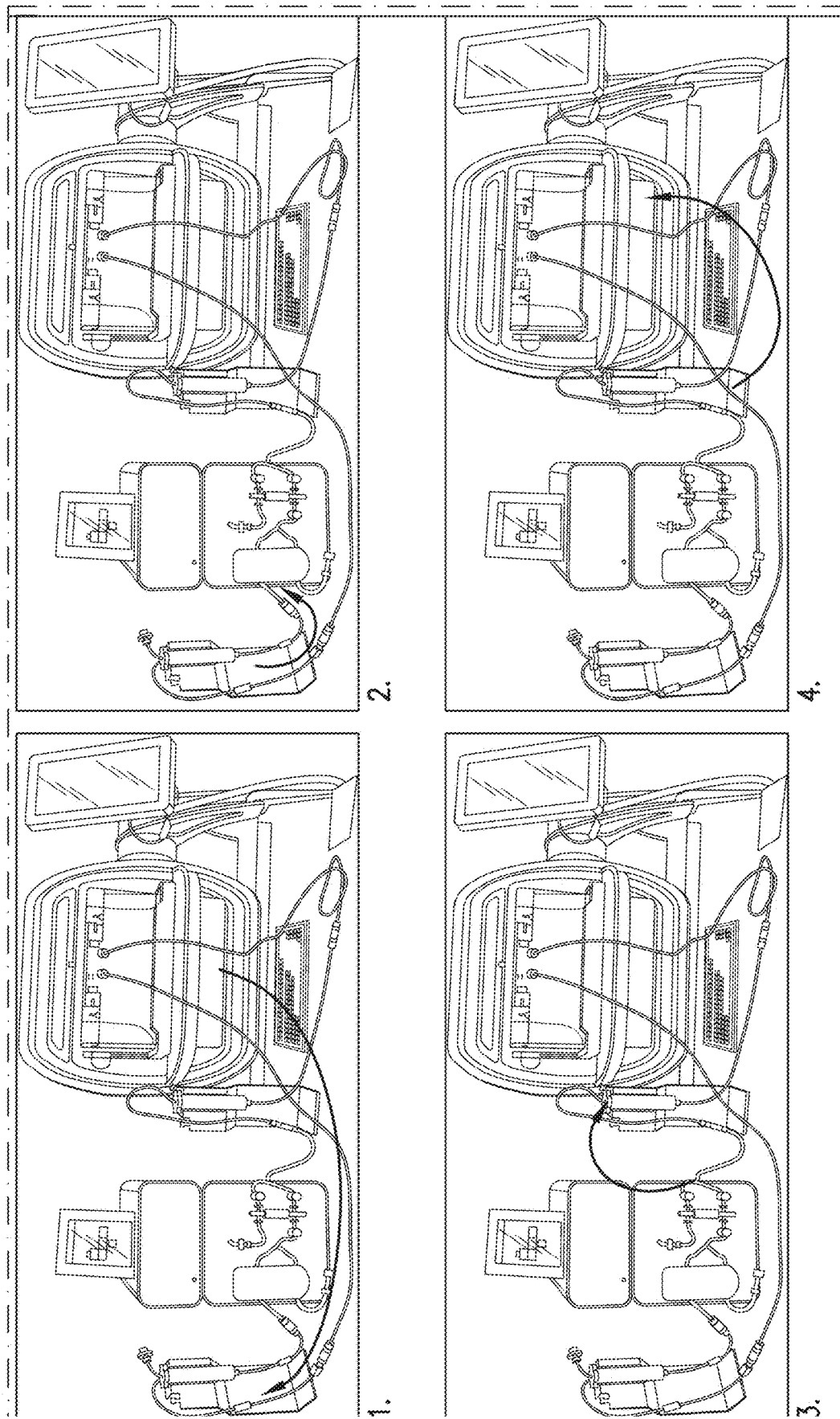
FIG. 18 shows the flow of immune cell culture from a cell engineering system to an electroporation unit and back again.

FIG. 18 shows a flow diagram of the cell culture 1) from the cell engineering system to a first reservoir, 2) to the electroporation unit, 3) to a second reservoir, and finally 4) back to cell engineering system.

In exemplary embodiments, as shown in FIGS. 17 and 18, electroporation unit 1706 is located outside of cell engineering system 1702. In such embodiments, the transducing comprises transferring via a first sterile, closed connection (e.g., connection tubing 1704), the activated immune cell culture from the first chamber to the electroporation unit, electroporating the activated immune cell culture with the vector, to produce the transduced immune cell culture, and transferring via a second sterile, closed connection (e.g., connection tubing 1704), the transduced immune cell culture to the second chamber of the cell engineering system.

It should also be understood that multiple, separate cell engineering systems 600 (see, e.g., FIG. 2) can be connected to a single electroporation unit, and run in appropriate order such that cell cultures are transferred from the cell engineering systems, to the electroporation unit, and then back to the appropriate cell engineering system.

In other embodiments, electroporation unit 1706 can be located within cell engineering system 600, such that the entire system is a closed, self-contained system. Methods for including electroporation unit 1706 inside of cell engineering system 600 are known by those of ordinary skill in the art, and utilize various miniaturization strategies, etc.

The various methods described herein allow for the production of genetically modified immune cell cultures where the transduction efficiency of the method is at least 20% higher than the transduction efficiency of the method utilizing a flexible, gas permeable bag for cell culture. As described herein, and as demonstrated in the Examples, the methods utilizing a cell engineering system as described herein are superior to traditional methods which rely on the use of a flexible, gas permeable bag for carrying out the cell culture. In further embodiments, the transduction efficiency of the method is at least 10% higher than the transduction efficiency of the method utilizing a flexible, gas permeable bag for cell culture, more suitably at least 20% higher, at least 25% higher, at least 30% higher, at least 35% higher, or in embodiments, at least 40% higher.

Suitably, the methods described herein produce at least 20% more genetically modified immune cells than a method utilizing manual cell culture with a flexible, gas permeable bag. More suitably, the methods produce at least 25% more genetically modified immune cells, at least 30% more genetically modified immune cells, at least 35% more genetically modified immune cells, or at least 40% more genetically modified immune cells than a method utilizing manual cell culture with a flexible, gas permeable bag.

In exemplary embodiments, the cell engineering systems described herein comprise a plurality of chambers, and wherein each of steps of the various method described herein are performed in a different chamber of the plurality of chambers of the cell engineering system, each of the activation reagent, the vector, and cell culture medium are contained in a different chamber of the plurality of the chambers prior to starting the method, and wherein at least one of the plurality of chambers is maintained at a temperature for growing cells (e.g., at about 37° C.) and at least one of the plurality of chambers is maintained at a refrigerated temperature (e.g., at about 4-8° C.).

In some embodiments, the disclosure provides a method of producing chimeric antigen receptor T cells, the method including: (a) activating a peripheral blood mononuclear cell culture, suitably with culture media comprising at least one of an anti-CD3 antibody and an anti-CD28 antibody, to produce an activated T cell culture; (b) transducing the activated T cell culture with a lentiviral vector, the vector encoding a chimeric antigen receptor, to produce a transduced T cell culture; (c) expanding the transduced T cell culture to a pre-defined culture size; (d) concentrating the expanded T cell culture of (c) to a volume of about 20 mL to about 500 mL, suitably about 50 mL to about 200 mL; and (e) harvesting the concentrated T cell culture of (d) to produce a chimeric antigen receptor T (CAR T) cell culture, wherein the activated T cell culture is substantially undisturbed during steps (a) to (b); wherein the method is performed by a fully enclosed cell engineering system, suitably having instructions thereon for performing steps (a) to (e). Suitably steps (a) to (e) are performed in one or more chambers of the cell engineering system. As described herein, in embodiments, the method produces at least 20% more CAR T cells than a method utilizing a flexible, gas permeable bag for cell culture. In exemplary embodiments, the method produce at least 2 billion viable CAR T cells.

A chimeric antigen receptor T cell, or "CART cell," is a T cell that is modified with a chimeric antigen receptor (CAR) to more specifically target cancer cells. In general, a CAR includes three parts: the ectodomain, the transmembrane domain, and the endodomain. The ectodomain is the region of the receptor that is exposed to extracellular fluid and includes three parts: a signaling peptide, an antigen recognition region, and a spacer. The signaling peptide directs the nascent protein into the endoplasmic reticulum. In CAR, the signaling peptide is a single-chain variable fragment (scFv). The scFv includes a light chain ($V_L$) and a heavy chain ($V_H$) of immunoglobins connected with a short linker peptide. In some embodiments, the linker includes glycine and serine. In some embodiments, the linker includes glutamate and lysine.

The transmembrane domain of the CAR is a hydrophobic α-helix that spans the membrane. In some embodiments, the transmembrane domain of a CAR is a CD28 transmembrane domain. In some embodiments, the CD28 transmembrane domain results in a highly expressed CAR. In some embodiments, the transmembrane domain of a CAR is a CD3-δ transmembrane domain. In some embodiments, the CD3-δ transmembrane domain results in a CAR that is incorporated into a native T cell receptor.

The endodomain of the CAR is generally considered the "functional" end of the receptor. After antigen recognition by the antigen recognition region of the ectodomain, the CARs cluster, and a signal is transmitted to the cell. In some embodiments, the endodomain is a CD3-δ endodomain, which includes 3 immunoreceptor tyrosine-based activation motifs (ITAMs). In this case, the ITAMs transmit an activation signal to the T cell after antigen binding, triggering a T cell immune response.

During production of CAR T cells, T cells are removed from a human subject, genetically altered, and re-introduced into a patient to attack the cancer cells. CAR T cells can be derived from either the patient's own blood (autologous), or derived from another healthy donor (allogenic). In general, CAR T cells are developed to be specific to the antigen expressed on a tumor that is not expressed in healthy cells.

Activation of T Cells. In some embodiments, an immune cell culture produced by the methods described herein is a CAR T cell culture. CAR T cells can be activated to form an activated T cell culture. In vivo, antigen-presenting cells (APCs), such as dendritic cells, act as the stimulus for T cell activation through the interaction of the T Cell Receptor (TCR) with the APC major histone compatibility complex (MHC). TCR associates with CD3, a T cell co-receptor that helps to activate both cytotoxic T cells (e.g., CD8+ naïve T cells) and T helper cells (e.g., CD4+ naïve T cells). In general, T cell activation follows a two-signal model, requiring stimulation of the TCR/CD3 complex as well as a co-stimulatory receptor. Activation of T cells is further described in, e.g., Kochenderfer 2015; Kalos 2011.

Without the co-stimulatory signal, the cells are susceptible to anergy and become non-responsive. Thus, T cell co-stimulation may be important for T cell proliferation, differentiation, and survival. Non-limiting examples of co-stimulatory molecules for T cells include CD28, which is a receptor for CD80 and CD86 on the membrane of APC; and CD278 or ICOS (Inducible T-cell COStimulator), which is a CD28 superfamily molecule expressed on activated T cells that interacts with ICOS-L. Thus, in some embodiments, the co-stimulatory molecule is CD28. In other embodiments, the co-stimulatory molecule is ICOS. In vivo, the co-stimulatory signal can be provided by the B7 molecules on the APC, which bind to the CD28 receptor on T cells. B7 is a peripheral transmembrane protein found on activated APCs that can interact with CD28 or CD152 surface proteins on a T cell to produce a co-stimulatory signal. Thus, in some embodiments, the co-stimulatory molecule is B7. Co-stimulatory receptors are further described in, e.g., Lafferty 1975; Harding 1992; Clavreul 2000; Charron 2015; Fathman 2007; Greenwald 2005. Co-stimulation is further described in, e.g., Carpenter 2000; Andris 2004. B7 molecules are further described in, e.g., Fleischer 1996; Schwartz 2003.

Various methods of activation are utilized in vitro to simulate T cell activation. In embodiments, a T cell culture is activated with an activation reagent. In further embodiments, the activation reagent is an antigen-present cell (APC). In still further embodiments, the activation reagent is a dendritic cell. Dendritic cells are APCs that process antigen and present it on the cell surface to T cells. In some embodiments, the activation reagent is co-cultured with the T cell culture. Co-culturing may require separate purification and culturing of a second cell type, which may increase labor requirements and sources of variability. Thus, in some embodiments, alternative activation methods are used.

In embodiments, the cells maintain stable contact with the activation reagent during the activating step. One way to maintain stable contact between the cells and the activation reagent is by preventing unnecessary or excessive movement of the cells. Accordingly, in embodiments, the cell culture is substantially undisturbed during the activation step. "Substantially undisturbed" means that the cells generally remain in the same area of the cell culture chamber, e.g., the bottom of the chamber, while the cell culture media is being changed. Cells may be disturbed if they are moved between different vessels, e.g., transferred from one culture flask to another, or cells may be disturbed if the vessel is flexible. A flexible vessel such as, e.g., a culture bag, can cause the cells to move when the bag is handled. As described herein, the methods suitably utilize a cell culture chamber that is substantially flat, and low, to allow for uniform access of the cells to various nutrients and gases, also allowing for ease of removal of waste products and media transfer. The substantially flat cell culture chamber also allows for the cells to touch each other during various stages of the methods which can enhance cell growth and production of the desired cell phenotype(s).

In some embodiments, the activation reagent is an antibody. In some embodiments, the cell culture is activated with an antibody bound to a surface, including a polymer surface, including a beads In further embodiments, the one or more antibodies is an anti-CD3 and/or anti-CD28 antibody. For example, the beads may be magnetic beads such as, e.g., DYNABEAD(S)™, coated with anti-CD3 and anti-CD28. The anti-CD3 and anti-CD28 beads can suitably provide the stimulatory signals to support T cell activation. See, e.g., Riddell 1990; Trickett 2003.

In other embodiments, the cell culture is activated with a soluble antibody. In further embodiments, the soluble antibody is a soluble anti-CD3 antibody. OKT3 is a murine monoclonal antibody of the immunoglobulin IgG2a isotype and targets CD3. Thus, in some embodiments, the soluble anti-CD3 antibody is OKT3. OKT3 is further described in, e.g., Dudley 2003; Manger 1985; Ceuppens 1985; Van Wauwe 1980; Norman 1995.

In some embodiments, the co-stimulatory signal for T cell activation is provided by accessory cells. Accessory cells may include, for example, a Fc receptor, which enables cross-linking of the CD3 antibody with the TCR/CD3 complex on the T cell. In some embodiments, the cell culture is a mixed population of peripheral blood mononuclear cells (PBMCs). PBMC may include accessory cells capable of supporting T cell activation. For example, CD28 co-stimulatory signals can be provided by the B7 molecules present on monocytes in the PBMC. Accordingly, in some embodiments, the accessory cells include a monocyte or a monocyte-derived cell (e.g., a dendritic cell). In additional embodiments, the accessory cells include B7, CD28, and/or ICOS. Accessory cells are further described in, e.g., Wolf 1994; Chai 1997; Verwilghen 1991; Schwartz 1990; Ju 2003; Baroja 1989; Austyn 1987; Tax 1983.

As described herein, activation reagent may determine the phenotype of the CAR T cells produced, allowing for the promotion of a desired phenotype. In some embodiments, the activation reagent determines the ratio of T cell subsets, i.e., CD4+ helper T cells and CD8+ cytotoxic T cells. The cytotoxic CD8+ T cells are typically responsible for killing cancer cells (i.e., the anti-tumor response), cells that are infected (e.g., with viruses), or cells that are damaged in other ways. CD4+ T cells typically produce cytokines and help to modulate the immune response, and in some cases may support cell lysis. CD4+ cells activate APCs, which then primes naïve CD8+ T cells for the anti-tumor response. Accordingly, in embodiments, the methods of the present disclosure further include producing CAR T cells of a pre-defined phenotype (i.e., promoting cells of a desired phenotype). The pre-defined phenotype may be, for example, a pre-defined ratio of CD8+ cells to CD4+ cells. In some embodiments, the ratio of CD8+ cells to CD4+ cells in a population of CAR T cells is about 1:1, about 0.25:1, or about 0.5:1. In other embodiments, the ratio of CD8+ cells to CD4+ cells in a population of CAR T cells is about 2:1, about 3:1, about 4:1, or about 5:1.

In embodiments, the activation reagent is removed from the activated T cell culture after the activation step. The activation reagent, e.g., an anti-CD3 antibody and/or an anti-CD28 antibody may be present in the cell culture media. Thus, in some embodiments, the cell culture media containing the activation reagent, e.g., an anti-CD3 antibody and/or an anti-CD28 antibody, is removed from the activated T cell culture after the activation step. In some embodiments, removal of the activation reagent includes removing a soluble antibody. For example, the soluble antibody can be removed by exchanging the cell culture media. The soluble antibody can also be removed by affinity methods specific for the soluble antibody. In other embodiments, removal of the activation reagent includes removing the bead containing the antibody. Bead removal can include, for example, filtering the beads or removal by a magnet.

Transduction of Activated T Cells. In some embodiments, the genetically modified immune cell culture is an activated T cell culture that is transduced with a vector encoding a chimeric antigen receptor to produce a transduced T cell culture. In some embodiments, the transduction includes viral infection, transposons, m RNA transfection, electroporation, or combinations thereof. In some embodiments, the transduction includes electroporation. Accordingly, in embodiments, the cell engineering system includes an electroporation system or electroporation unit, as described herein. In additional embodiments, the transduction includes viral infection. The vector may be a viral vector, such as, for example, a lentiviral vector, a gammaretroviral vector, an adeno-associated viral vector, or an adenoviral vector. In embodiments, the transduction includes introducing a viral vector into the activated T cells of the cell culture. In additional embodiments, the vector is delivered as a viral particle.

In some embodiments, the transduction step includes transducing the activated T cells with a lentiviral vector, wherein the lentiviral vector is introduced at a multiplicity of infection (MOI) of about 0.5 to about 50, about 0.5 to about 30, or about 0.5 to about 20. In some embodiments, the lentiviral vector is introduced at a MOI of about 0.5 to about 8. In some embodiments, the lentiviral vector is introduced at a MOI of about 0.5 to about 6. In some embodiments, the lentiviral vector is introduced at a MOI of about 0.5 to about 4. In some embodiments, the lentiviral vector is introduced at a MOI of about 0.5 to about 2. In some embodiments, the lentiviral vector is introduced at a MOI of about 0.6 to about 1.5. In some embodiments, the lentiviral vector is introduced at a MOI of about 0.7 to about 1.3. In some embodiments, the lentiviral vector is introduced at a MOI of about 0.8 to about 1.1. In some embodiments, the lentiviral vector is introduced at a MOI of about 0.5, about 0.6, about 0.7, about 0.8, about 0.9, about 1, about 1.1, about 1.2, about 1.3, about 1.4, about 1.5, about 1.6, about 1.7, about 1.8, about 1.9, or about 2.

In some embodiments, after the activation step, the cell culture media from the T cell culture is removed, and the media is then mixed with the vector (e.g., lentiviral vector) and distributed uniformly to the cells. In some embodiments, the removed cell culture media is used to dilute and uniformly deliver the vector to the activated T cell culture. Uniform distribution and consequent homogeneous exposure of the vector (e.g., lentiviral vector) in the T cell culture improves transduction efficiency. In some embodiments, the volume of the cell culture is reduced after activation, and prior to addition of the vector. Volume reduction may enable a higher degree of cell-vector contact. In some embodiments, the activated T cell culture is substantially undisturbed during the transduction. In some embodiments, the cell culture is substantially undisturbed during the activation and transduction steps, i.e., the cells remain generally in the same area of the chamber (e.g., the bottom of the cell culture chamber) while the activation reagent or the vector is being provided to the cells. This may facilitate uniform distribution and homogeneous exposure of the activation reagent and/or vector to the cells, and thus may improve the activation and/or transduction efficiency.

Accordingly, in some embodiments, the transduction efficiency of the method using the cell engineering system is higher than the transduction efficiency of a method using a flexible, gas-permeable bag for cell culture. In some embodiments, the transduction efficiency of the method for automated production of CAR T cells as described herein has at least 10% greater, at least 15% greater, at least 20% greater, at least 25% greater, at least 30% greater, at least 35% greater, at least 40% greater, at least 45% greater, at least 50% greater, at least 55% greater, at least 60% greater, at least 65% greater, at least 70% greater, at least 75% greater, at least 80% greater, at least 85% greater, at least 90% greater, at least 95% greater, or at least 100% greater than the transduction efficiency of a method utilizing a flexible, gas-permeable bag.

Expansion of Transduced T Cells. In some embodiments, the transduced T cell culture (or other immune cell culture) is expanded to a pre-defined culture size (i.e., number of cells). The pre-defined culture size may include a sufficient number of cells suitable for clinical use, i.e., transfusion into a patient, research and development work, etc. In some embodiments, a clinical or therapeutic dose of CAR T cells for administration to a patient is about $10^5$ cells, about $10^6$ cells, about $10^7$ cells, about $10^8$ cells, about $10^9$ cells, or about $10^{10}$ cells. In some embodiments, the method produces at least 1, at least 2, at least 3, at least 4, at least 5, at least 10, at least 15, at least 20, at least 25, at least 30, at least 35, at least 40, at least 45, at least 50, at least 60, at least 70, at least 80, at least 90, or at least 100 clinical doses of CAR T cells. In some embodiments, the transduced T cell culture is expanded to a total volume of from about 0.1 L to about 5 L, from about 0.1 L to about 2 L, or from about 0.2 L to about 2 L. In some embodiments, the transduced T cell culture is expanded to a total volume of about 0.1 L, about 0.2 L, about 0.3 L, about 0.4 L, about 0.5 L, about 0.6 L, about 0.7 L, about 0.8 L, about 0.9 L or about 1.0 L. The volume can also be varied through the process, as required based on the stage of the cell production process. In some embodiments, the pre-defined culture size is input by a user of the cell engineering system. The user may input the pre-defined culture size as a desired cell count to be produced (e.g., $10^{10}$ CART cells), or, the pre-defined culture size may be input as a desired number of clinical or therapeutic doses to be produced (e.g., 10 clinical or therapeutic doses of CART cells). In embodiments, the number of CAR T cells produced by the methods described herein is at least about 100 million (i.e., $1*10^6$) cells, or at least about 300 million, at least about 500 million, at least about 600 million, at least about 700 million, at least about 800 million, at least about 900 million, at least about 1 billion (i.e., $1*10^9$), at least about 1.1 billion, at least about 1.2 billion, at least about 1.3 billion, at least about 1.4 billion, at least about 1.5 billion, at least about 1.6 billion, at least about 1.7 billion, at least about 1.8 billion, at least about 1.9 billion, at least about 2 billion (i.e., $2*10^9$) cells, including at least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, or at least about 3.0 billion CAR T cells.

In some embodiments, the expanding of the transduced T cell culture includes at least one round of feeding, washing, monitoring, and selecting of the transduced T cell culture. Feeding the cell culture may include supplementing the cell culture with media and/or additional nutrients. Washing the cell culture may include removing spent media (i.e., media that is depleted of nutrients and/or contains cellular waste products) and replenishing the cell culture with fresh media. Monitoring the cell culture may include monitoring the temperature, pH, glucose, oxygen level, carbon dioxide level, and/or optical density of the cell culture. Selecting the cell culture may include selecting the cells with the desired characteristics such as, e.g., viability, type, and/or morphology, and removing cells that do not have the desired characteristics. In some embodiments, the cell engineering system is configured to perform several rounds of the feeding, washing, monitoring, and/or selecting of the transduced T cell culture to achieve the pre-defined culture size. In some embodiments, the cell engineering system performs at least 2, at least 3, at least 4, at least 5, at least 6, at least 7, at least 8, at least 9, at least 10, at least 15, at least 20, at least 25, at least 30, at least 35, at least 40, at least 45, at least 50, or at least 100 rounds of the feeding, washing, monitoring, and/or selecting of the transduced T cell culture to achieve the pre-defined culture size.

In embodiments, one or more of the feeding, washing and monitoring can be removed, or the order of the events can be changed depending on the desired cellular phenotype or number of cells, etc.

In embodiments, the monitoring includes monitoring with a temperature sensor, a pH sensor, a glucose sensor, an oxygen sensor, a carbon dioxide sensor, and/or an optical density sensor. Accordingly, in some embodiments, the cell engineering system includes one or more of a temperature sensor, a pH sensor, a glucose sensor, an oxygen sensor, a carbon dioxide sensor, and/or an optical density sensor. In additional embodiments, the cell engineering system is configured to adjust the temperature, pH, glucose, oxygen level, carbon dioxide level, and/or optical density of the cell culture, based on the pre-defined culture size. For example, if the cell engineering system detects that the current oxygen level of the cell culture is too low to achieve the necessary growth for a desired cell culture size, the cell engineering system will automatically increase the oxygen level of the cell culture by, e.g., introducing oxygenated cell culture media, by replacing the cell culture media with oxygenated cell culture media, or by flowing the cell culture media through an oxygenation component (i.e., a silicone tubing). In another example, if the cell engineering system detects that the current temperature of the cell culture is too high and that the cells are growing too rapidly (e.g., possible overcrowding of the cells may lead to undesirable characteristics), the cell engineering system will automatically decrease the temperature of the cell culture to maintain a steady growth rate (or exponential growth rate, as desired) of the cells. In still further embodiments, the cell engineering system automatically adjusts the schedule of cell feeding (i.e., providing fresh media and/or nutrients to the cell culture) based on the cell growth rate and/or cell count, or other monitored factors, such as pH, oxygen, glucose, etc. The cell engineering system may be configured to store media (and other reagents, such as wash solutions, etc.) in a low-temperature chamber (e.g., 4° C. or −20° C.), and to warm the media in a room temperature chamber or a high-temperature chamber (e.g., 25° C. or 37° C., respectively) before introducing the warmed media to the cell culture.

In embodiments, the washing includes washing the cells by filtration or sedimentation. In some embodiments, the washing step does not require moving the cell culture vessels or flasks, i.e., the cells can be washed in the same cell culture vessel or flask. In further embodiments, the cells remain substantially undisturbed during the washing step. In embodiments, the selecting includes mixing the cell culture with one or more selection reagents. The selection reagent may be a bead, e.g., a magnetic bead, that is specific for the desired cell type, and the cells bound to the beads are then separated from non-bound cells, e.g., by passing through a magnetic chamber. For example, the selection bead includes an antibody specific for a desired cell type, e.g., an anti-CD8 antibody or an anti-CD4 antibody. Selection can also be performed by filtration to remove or select certain cell types based on size. Cell selection by plastic-adhesion (i.e. cells can start in one chamber, the unwanted cells stick to the surface and then the desired cells, that are still in suspension, are moved to another chamber), can also be utilized.

Suitably, during the expansion stage, the cells are not shaken or rotated. It has been determined that maintaining the cells in a relatively stationary position during expansion helps aid in overall cell production, as well as providing the desired cellular phenotype.

Concentration of the Expanded Culture. In some embodiments, the expanded T cell culture (or other immune cell culture) is concentrated to a pre-defined concentration. The pre-defined concentration is of a volume that can be suitably infused into a patient. For example, the expanded T cell culture can be concentrated to about 1 ml, about 2 ml, about 5 ml, about 10 ml, about 15 ml, about 20 ml, about 25 ml, about 30 ml, about 35 ml, about 40 ml, about 45 ml, about 50 ml, about 55 ml, about 60 ml, about 65 ml, about 70 ml, about 75 ml, about 80 ml, about 85 ml, about 90 ml, about 95 ml, or about 100 ml. In some embodiments, the concentration is performed by centrifugation. In some embodiments, the concentration is performed by filtration. In some embodiments, the filtration is ultrafiltration and/or diafiltration. In some embodiments, the pre-defined concentration is input by a user of the cell engineering system. In other embodiments, the pre-defined concentration is determined by the cell engineering system, based on a different parameter input by the user, for example, the number or volume of clinical or therapeutic doses to be produced; or the number of cells to be produced. In some embodiments, the cell engineering system automatically adjusts the volume or number of clinical or therapeutic doses produced, based on the input parameters. In some embodiments, the cell engineering system automatically adjusts parameters of the centrifugation (e.g., speed, duration of centrifuging) or filtration (e.g., filter size, volume, duration) based on the pre-defined concentration.

Sedimentation based on the port position and design of the chamber can also be utilized. That is, the fluid volume can be reduced in the chamber to approximately 0.5 mL without removing the cells.

CAR T Cell Culture Harvest. In some embodiments, the concentrated T cell culture (or other immune cell culture) is harvested, suitably to produce a chimeric antigen receptor (CAR) T cell culture. In some embodiments, the harvesting includes agitation, fluid flow, and washing of the CAR T cells. In some embodiments, the harvesting includes separation of the cells from undesired products, which include, e.g., cellular waste products, selection reagents such as beads (e.g., beads containing antibodies and/or beads used for separation of cells), or excess viral vectors. In some embodiments, the harvesting includes uniform distribution of the CAR T cells into one or more flasks, vials or vessels. In some embodiments, the harvesting includes resuspending the CAR T cells in a formulation reagent, e.g., a solution that stabilizes the CAR T cells for long-term storage. In some embodiments, the harvesting includes cryopreservation of the CAR T cells.

Further Downstream Processes. In some embodiments, the CAR T cells undergo further downstream processing prior to therapeutic use in a patient. For example, the cryopreserved CAR T cells may be filtered by sterile filtration to remove potential viral particle remnants. After sterile filtration, the CAR T cells may undergo at least one more concentration step before packaged in one or more vials, flasks, vessels, or containers. The packaged CAR T cells may be subjected to quality assessment and/or quality control testing. In some embodiments, the CAR T cells undergo minimal downstream processing prior to administration to a patient. For example, in some embodiments, harvested CAR T cells are not cryopreserved but transferred to the patient within a short time period after harvest. Avoiding the cryopreservation step may increase the viability of the cells.

Cell Engineering Systems. In some embodiments, the methods described herein are performed by a fully enclosed cell engineering system 600 (see FIGS. 6A, 6B), suitably having instructions thereon for performing the activating, transducing, expanding, concentrating, and harvesting steps. Cell engineering systems for automated production of genetically modified immune cells, including CAR T cells, are described herein, and are also called automated cell engineering system, COCOON™, or COCOON™ system throughout. For example, a user can provide a cell engineering system pre-filled with a cell culture and reagents (e.g., an activation reagent, a vector, cell culture media, nutrients, selection reagent, and the like) and parameters for the cell production (e.g., starting number of cells, type of media, type of activation reagent, type of vector, number of cells or doses to be produced, and the like), the cell engineering system is able to carry out the methods of producing genetically modified immune cell cultures, including CAR T cells, without further input from the user. At the end of the automated production process, the cell engineering system may alert the user (e.g., by playing an alert message or sending a mobile app alert) for collecting the produced cells. In some embodiments, the fully enclosed cell engineering system includes sterile cell culture chambers. In some embodiments, the fully enclosed cell engineering system minimizes contamination of the cell cultures by reducing exposure of the cell culture to non-sterile environments. In additional embodiments, the fully enclosed cell engineering system minimizes contamination of the cell cultures by reducing user handling of the cells.

As described herein, the cell engineering systems suitably include a cassette 602. Thus, in embodiments, provided herein is a cassette for use in an automated cell engineering system. As used herein a "cassette" refers to a largely self-contained, removable and replaceable element of a cell engineering system that includes one or more chambers for carrying out the various elements of the methods described herein, and suitably also includes one or more of a cell media, an activation reagent, a vector, etc.

Figure 6A:
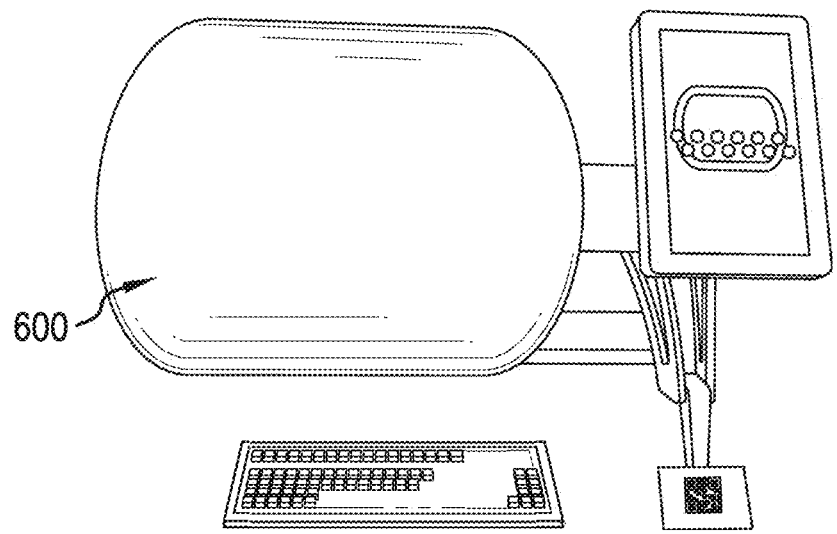
FIGS. 6A-6C show an overview of a COCOON™ system as used in Example 1.
Figure 6B:
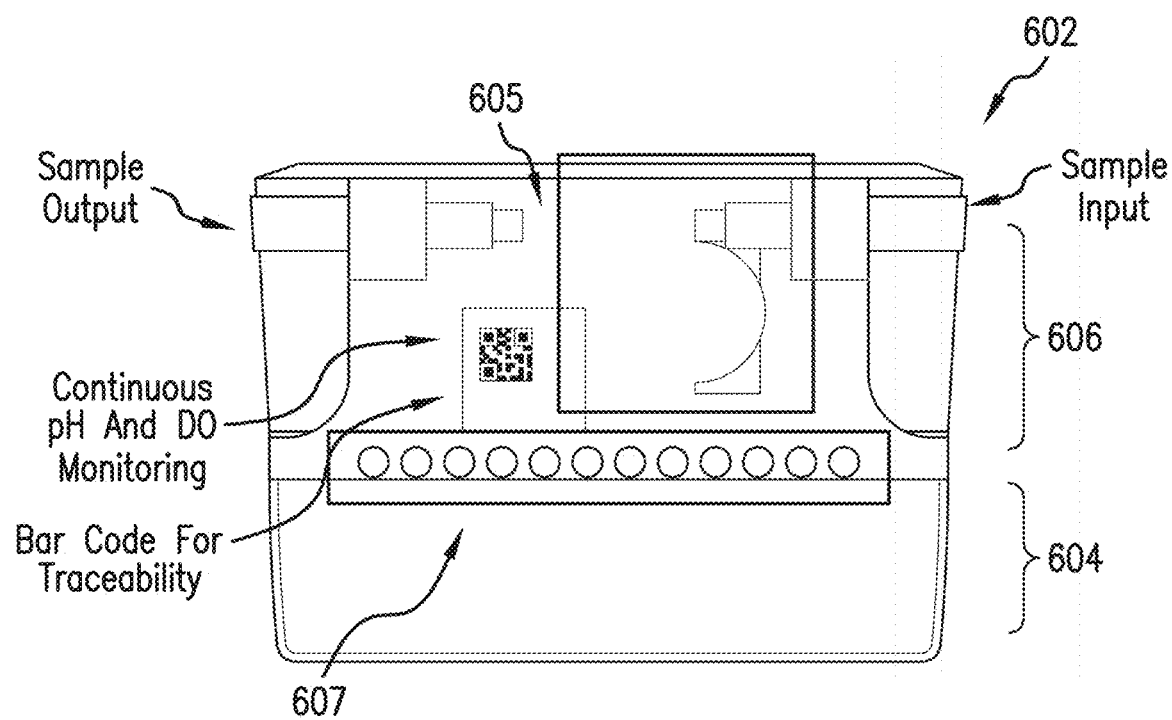

FIG. 6B shows an embodiments of a cassette 602 in accordance with embodiments hereof. In embodiments, cassette 602 includes a low temperature chamber 604, suitably for storage of a cell culture media, as well as a high temperature chamber 606, suitably for carrying out activation, transduction and/or expansion of an immune cell culture. Suitably, high temperature chamber 606 is separated from low temperature chamber 606 by a thermal barrier 1102 (see FIG. 11B). As used herein "low temperature chamber" refers to a chamber, suitably maintained below room temperature, and more suitably from about 4° C. to about 8° C., for maintenance of cell media, etc., at a refrigerated temperature. The low temperature chamber can include a bag or other holder for media, including about 1 L, about 2 L, about 3 L, about 4 L, or about 5 L of fluid. Additional media bags or other fluid sources can be connected externally to the cassette, and connected to the cassette via an access port.

As used herein "high temperature chamber" refers to chamber, suitably maintained above room temperature, and more suitably maintained at a temperature to allow for cell proliferation and growth, i.e., between about 35-40° C., and more suitably about 37° C.

Figure 6C:
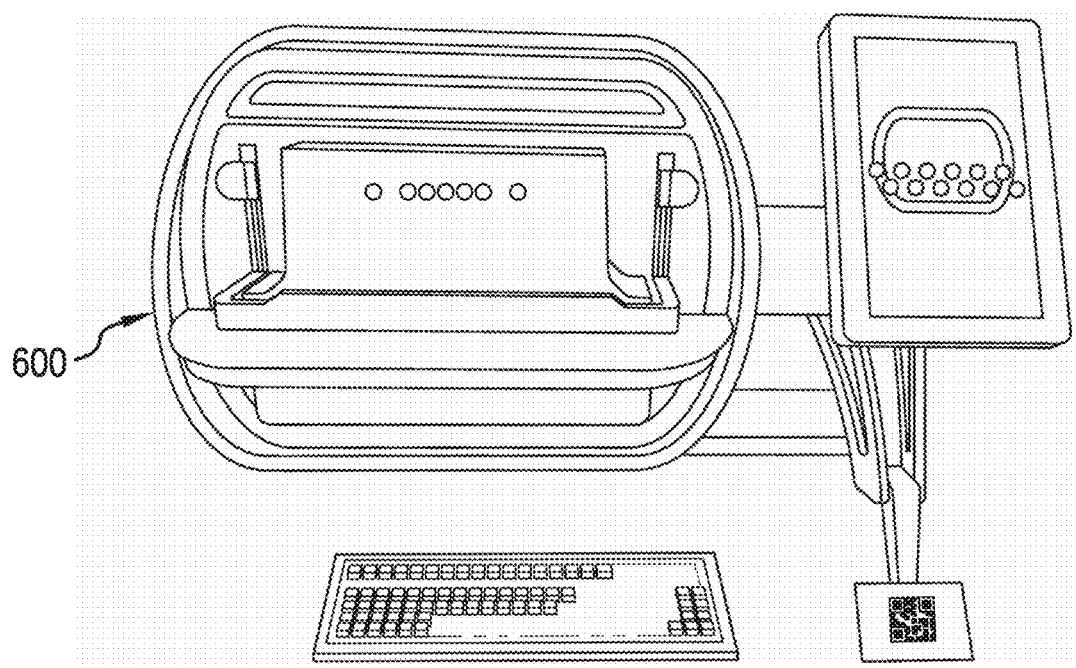
Figure 6D:
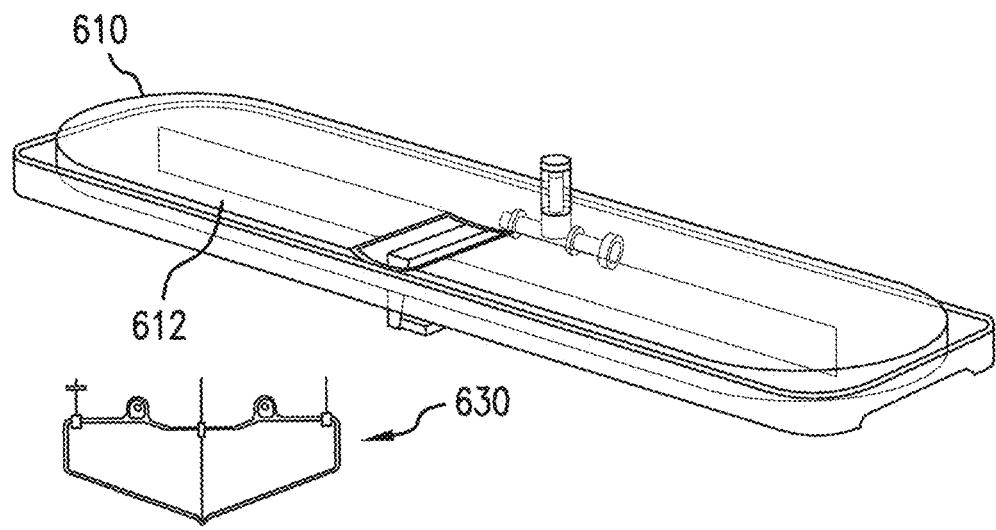
FIGS. 6D-6E show the location and orientation of a cell culture chamber utilized in a COCOON™ system.
Figure 6E:
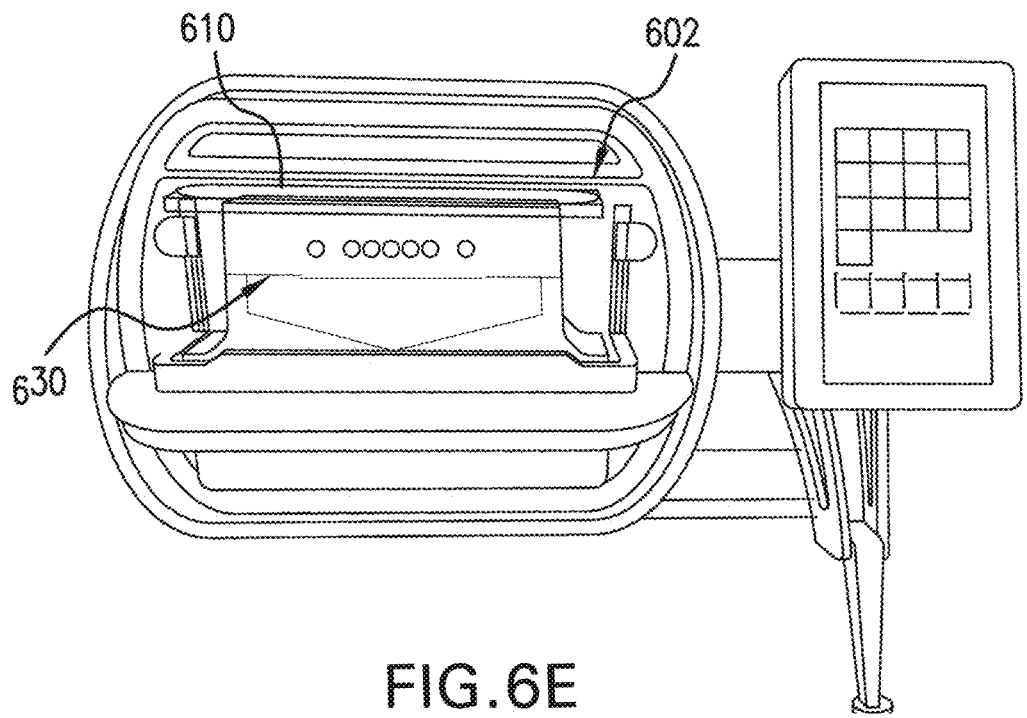

In embodiments, high temperature chamber 606 suitably includes a cell culture chamber 610 (also called proliferation chamber or cell proliferation chamber throughout), as shown in FIG. 6D and FIG. 6E.

The cassettes further include one or more fluidics pathways connected to the cell culture chamber, wherein the fluidics pathways provide recirculation, removal of waste and homogenous gas exchange and distribution of nutrients to the cell culture chamber without disturbing cells within the cell culture chamber. Cassette 602 also further includes one or more pumps 605, including peristaltic pumps, for driving fluid through the cassette, as described herein, as well as one or more valves 607, for controlling the flow through the various fluidic pathways.

In exemplary embodiments, as shown in FIG. 6D, cell culture chamber 610 is flat and non-flexible chamber (i.e., made of a substantially non-flexible material such as a plastic) that does not readily bend or flex. The use of a non-flexible chamber allows the cells to be maintained in a substantially undisturbed state. As shown in FIG. 6E, cell culture chamber 610 is oriented so as to allow the immune cell culture to spread across the bottom 612 of the cell culture chamber. As shown in FIG. 6E, cell culture chamber 610 is suitably maintained in a position that is parallel with the floor or table, maintaining the cell culture in an undisturbed state, allowing the cell culture to spread across a large area of the bottom 612 of the cell culture chamber. In embodiments, the overall thickness of cell culture chamber 610 (i.e., the chamber height 642) is low, on the order of about 0.5 cm to about 5 cm. Suitably, the cell culture chamber has a volume of between about 0.50 ml and about 300 ml, more suitably between about 50 ml and about 200 ml, or the cell culture chamber has a volume of about 180 ml. The use of a low chamber height 642 (less than 5 cm, suitably less than 4 cm, less than 3 cm, or less then 2 cm) allows for effective media and gas exchange in close proximity to the cells. Ports are configured to allow mixing via recirculation of the fluid without disturbing the cells. Larger height static vessels can produce concentration gradients, causing the area near the cells to be limited in oxygen and fresh nutrients. Through controlled flow dynamics, media exchanges can be performed without cell disturbance. Media can be removed from the additional chambers (no cells present) without risk of cell loss.

As described herein, in exemplary embodiments the cassette is pre-filled with one or more of a cell culture, a culture media, an activation reagent, and/or a vector, including any combination of these. In further embodiments, these various elements can be added later via suitable injection ports, etc.

Figure 11A:
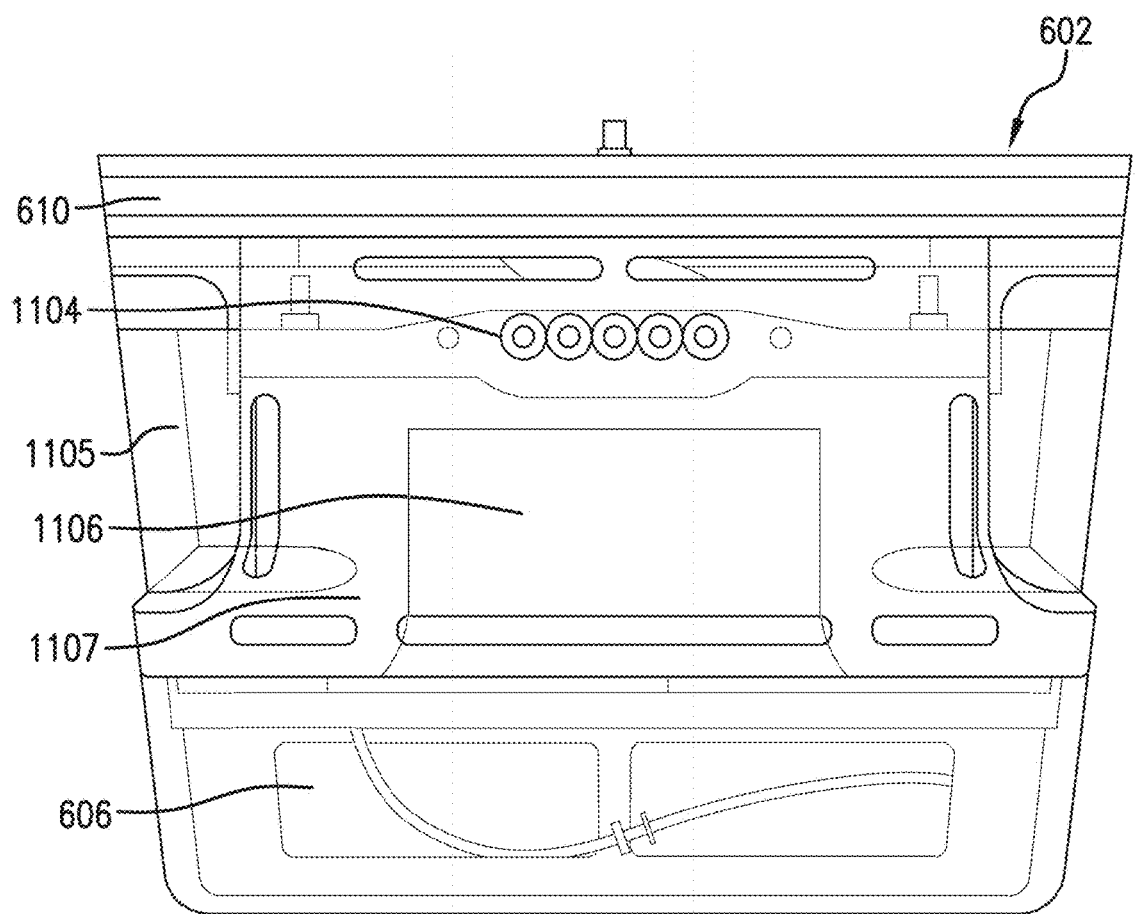
FIGS. 11A-11E show another configuration of a COCOON™ system as described in embodiments herein.

As described herein, in embodiments, the cassettes suitably further include one or more of a pH sensor, a glucose sensor, an oxygen sensor, a carbon dioxide sensor, a lactic acid sensor/monitor, and/or an optical density sensor. The cassettes can also include one or more sampling ports and/or injection ports. Examples of such sampling ports and injection ports (1104) are illustrated in FIG. 11A., and can include an access port for connecting the cartridge to an external device, such as an electroporation unit or an additional media source. FIG. 11A also shows the location of the cell input 1105, reagent warming bag 1106 which can be used to warm cell media, etc., as well as the culture zone 1107, which holds various components for use in the culture media, including for example, cell media, vectors, nutrients and waste products, etc.

Figure 11B:
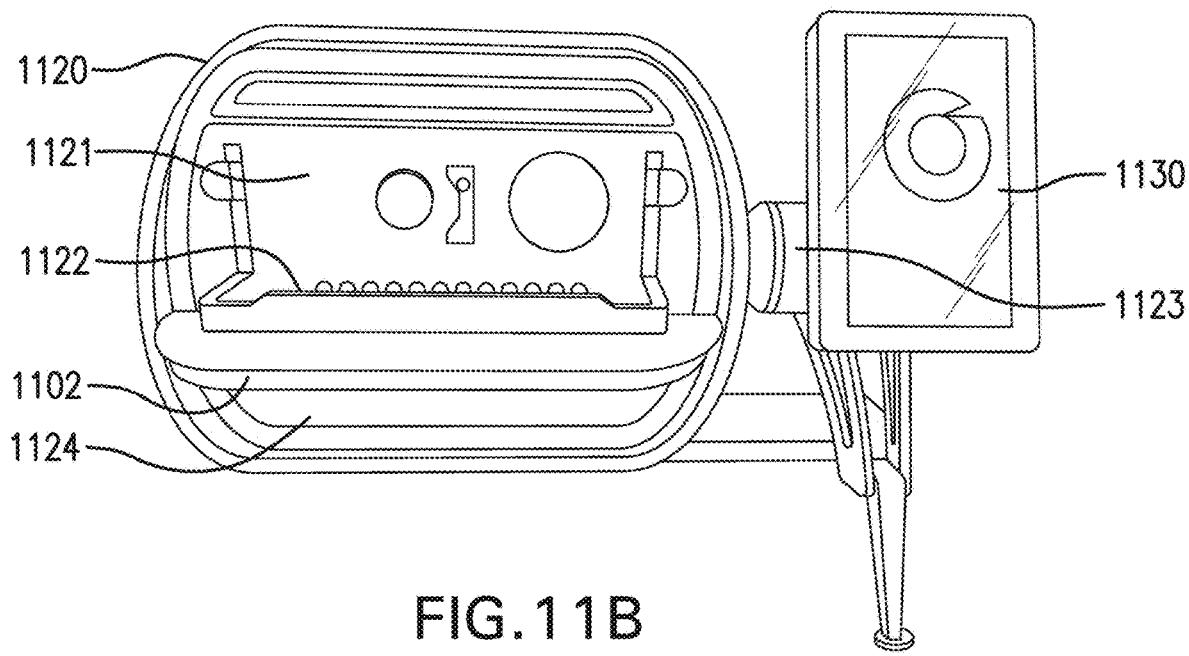
Figure 11C:
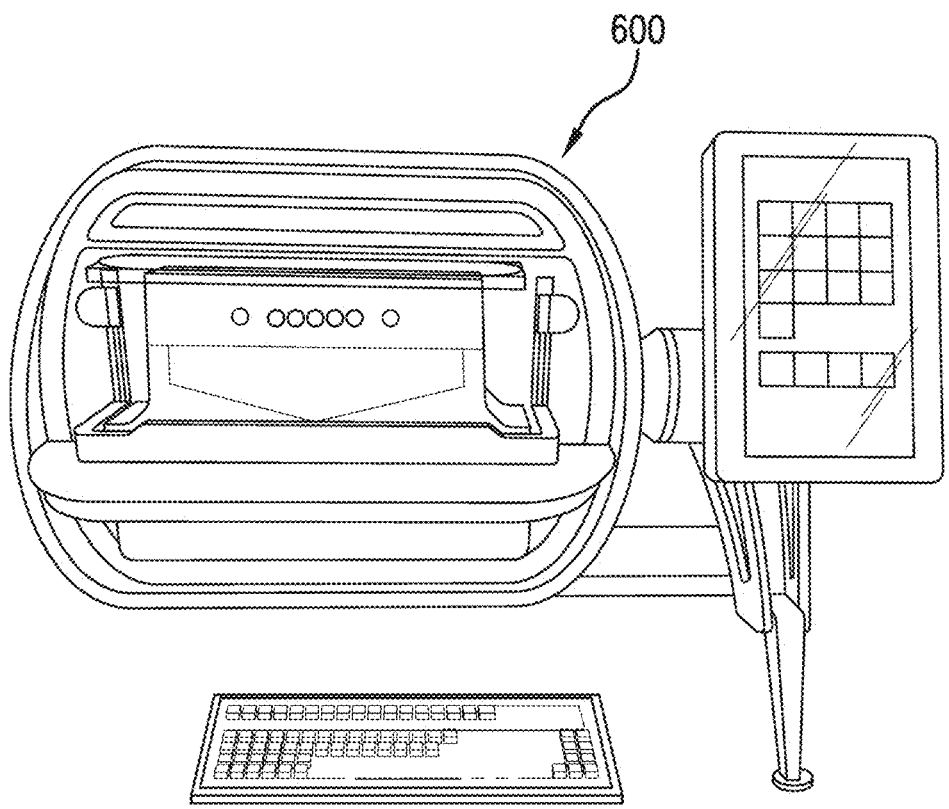
Figure 11D:
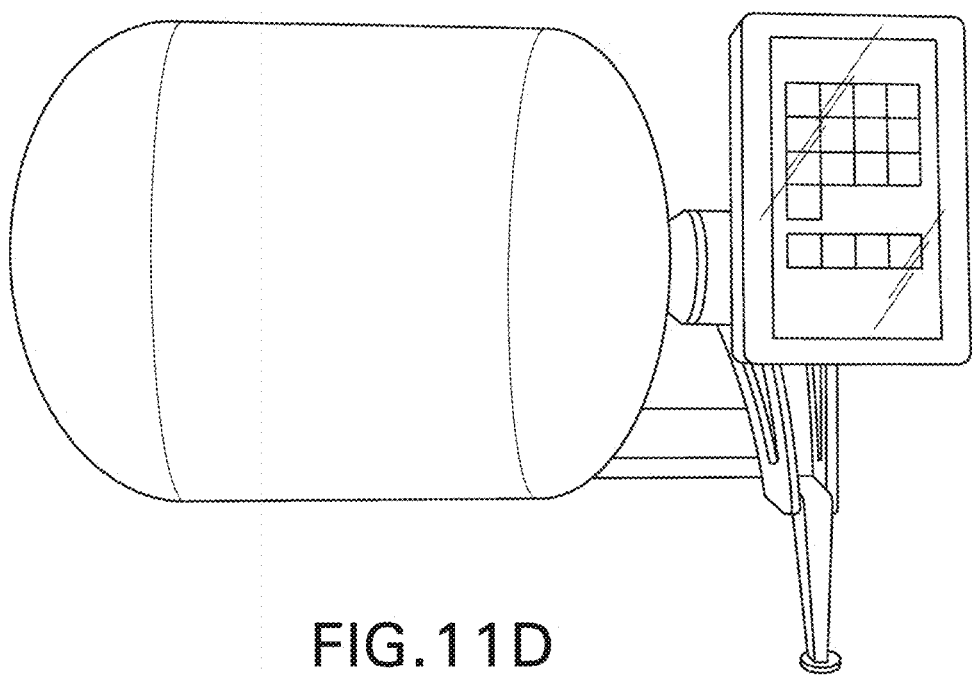
Figure 11E:
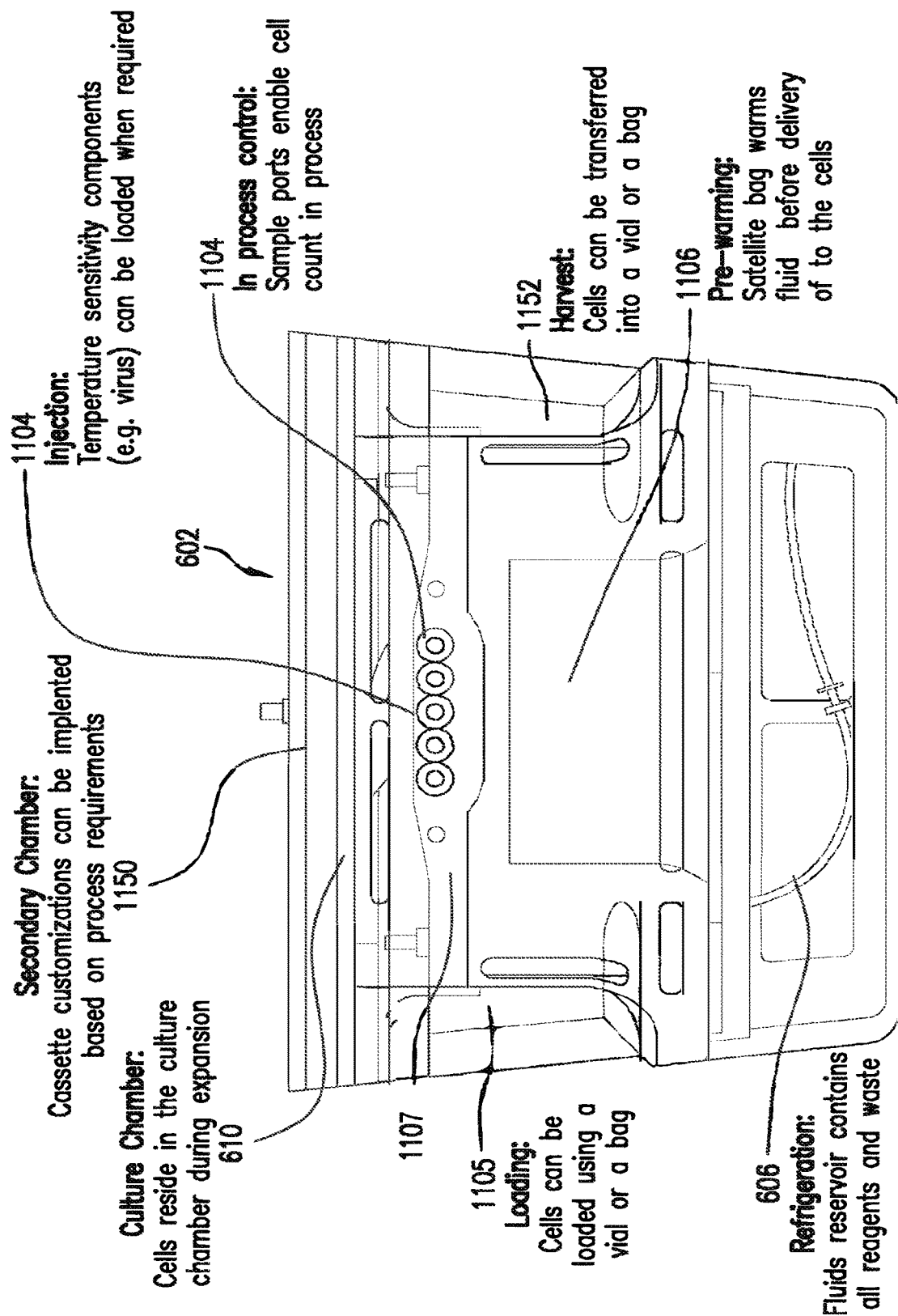

FIG. 11B shows the COCOON™ cell engineering system with cassette 602 removed. Visible in FIG. 11B are components of the cell engineering system, including gas control seal 1120, warming zone 1121, actuators 1122, pivot 1123 for rocking or tilting the cell engineering system as desired, and low temperature zone 1124 for holding low temperature chamber 606. Also shown is an exemplary user interface 1130, which can include a bar code reader, and the ability to receive using inputs by touch pad or other similar device. FIG. 11E shows an additional detailed view of cassette 602, including the location of secondary chamber 1150, which can be used is additional cell culture volume is required, as well as harvesting chamber 1152, which can be used to recover the final cell culture as produced herein.

In exemplary embodiments, as shown in FIG. 6F, cell culture chamber 610 further comprises at least one of: a distal port 620 configured to allow for the removal of air bubbles from the cell culture chamber and/or as a recirculation port; a medial port 622 configured to function as a recirculation inlet port; and a proximal port 624 configured to function as a drain port for cell removal.

In still further embodiments, provided herein is cassette 602 for use in an automated cell engineering system 600, comprising cell culture chamber 610 for carrying out activation, transduction and/or expansion of an immune cell culture having a chamber volume that is configured to house an immune cell culture and a satellite volume 630 for increasing the working volume of the cell culture chamber by providing additional volume for media and other working fluids without housing the immune cell culture (i.e., satellite volume does not contain any cells). Suitably, the satellite volume is fluidly connected to the cell culture chamber such that media is exchanged with the culture chamber without disturbing the immune cell culture. In exemplary embodiments, satellite volume is a bag, and in other embodiments, satellite volume is a non-yielding chamber. In embodiments, the satellite volume is between about 0.50 ml and about 300 ml, more suitably between about 150 ml and about 200 ml. FIG. 6D-6E show the position of a satellite volume 630 in cassette 602.

Figure 6G:
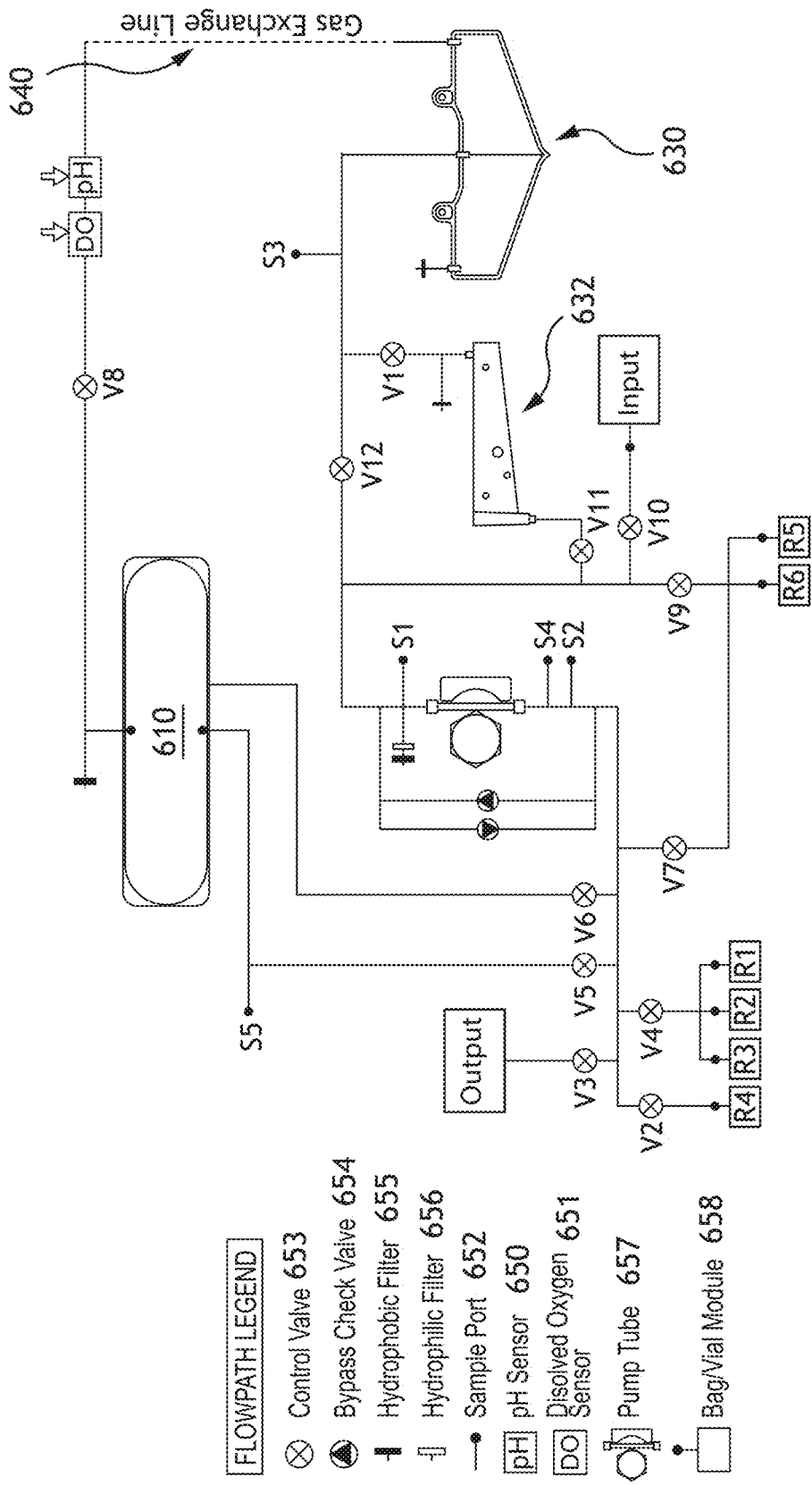
FIG. 6G shows process flow legend for a COCOON™ system.

FIG. 6G shows a schematic illustrating the connection between cell culture chamber 610, and satellite volume 630. Also illustrated in FIG. 6G are the positioning of various sensors (e.g., pH sensor 650, dissolved oxygen sensor 651), as well as sampling/sample ports 652 and various valves (control valves 653, bypass check valves 654), as well as one or more fluidic pathways 640, suitably comprising a silicone-based tubing component, connecting the components. As described herein, use of a silicone-based tubing component allows oxygenation through the tubing component to facilitate gas transfer and optimal oxygenation for the cell culture. Also show in FIG. 6G is the use of one or more hydrophobic filters 655 or hydrophilic filters 656, in the flow path of the cassette, along with pump tube 657 and bag/valve module 658.

Figure 6H:
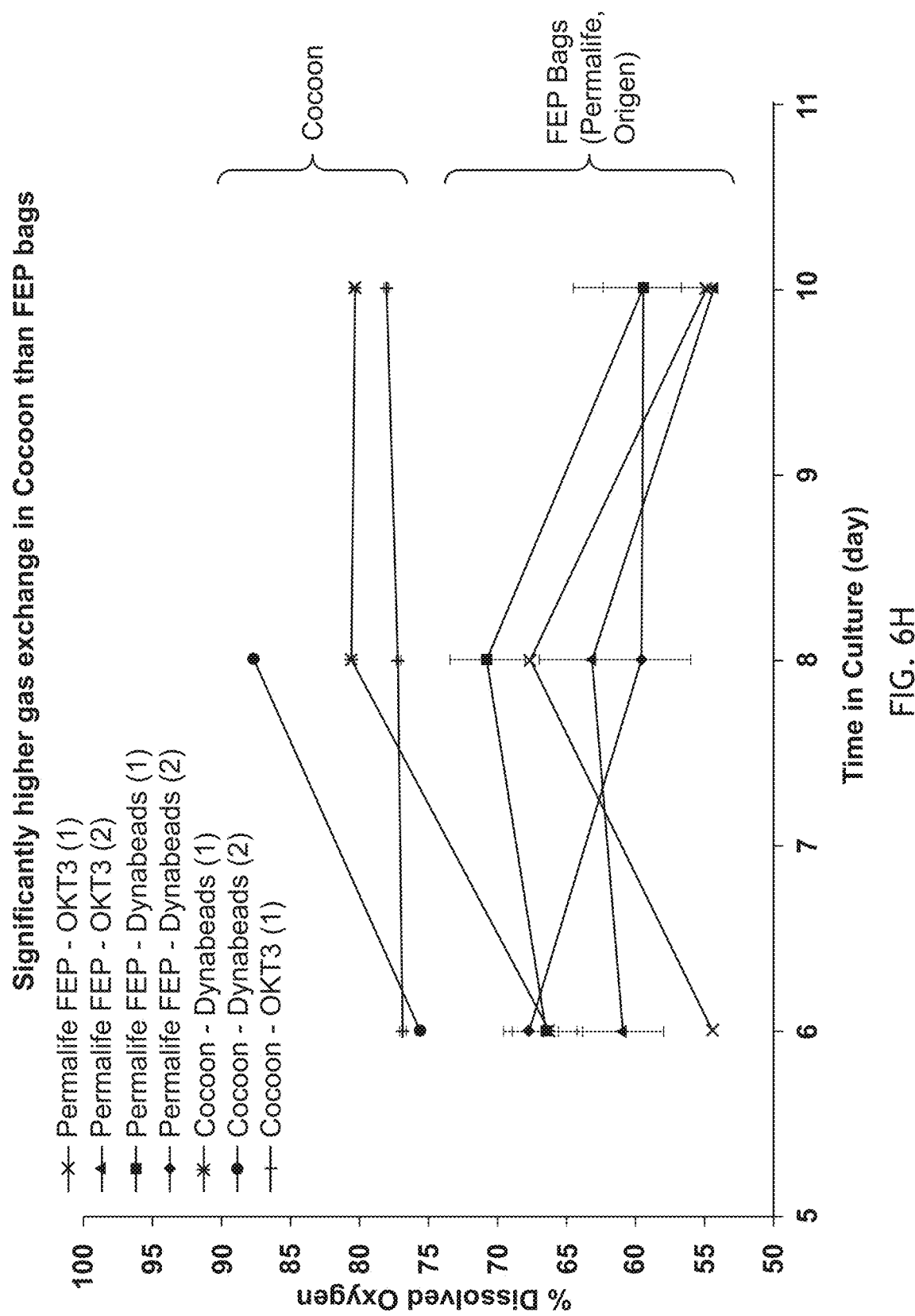
FIG. 6H shows gas transfer data using the COCOON™ system.

FIG. 6H shows gas exchange data using the COCOON™ system, as compared to traditional bags.

In embodiments, satellite volume 630 is further configured to allow media removal without loss of cells of the immune cell culture. That is, the media exchange between the satellite volume and the cell culture chamber is performed in such a manner that the cells are not disturbed and are not removed from the cell culture chamber.

In additional embodiments, as shown in FIG. 6G, cassette 602 suitably further includes a crossflow reservoir 632 for holding additional media, etc., as needed. Suitably, the crossflow reservoir has a volume of between about 0.50 ml and about 300 ml, more suitably between about 100 ml and about 150 ml.

The cell engineering systems described herein suitably have three relevant volumes, the cell culture chamber volume, the working volume, and the total volume. Suitably, the working volume used in the cassette ranges from 180 mL to 460 mL based on the process step, and can be increased up to about 500 mL, about 600 mL, about 700 mL, about 800 mL, about 900 mL or about 1 L. In embodiments, the cassette can readily achieve $4*10^9$ cells-$10*10^9$ cells. The cell concentration during the process varies from $0.3*10^6$ cells/ml to approximately $10*10^6$ cells/ml. The cells are located in the cell culture chamber, but media is continuously recirculated through additional chambers (e.g., crossflow reservoir and satellite volume) to increase the working volume, as described herein.

As described herein, unlike a flexible bag, which changes shape when filled with liquid (e.g., a cell culture) and when picked up or moved, a "substantially non-yielding chamber"

(e.g., an exemplary cell culture chamber 610) does not change shape (e.g., bend, curve, or deform) when filled with liquid, picked up, or moved during typical handling conditions. Thus, in some embodiments, a substantially non-yielding chamber allows cells to remain substantially in the same area of the chamber, even when the chamber is picked up or moved. A substantially non-yielding chamber also does not have the curvature associated with a bag. Thus, in some embodiments, the cells are distributed more uniformly in a substantially non-yielding chamber compared with a bag. In some embodiments, the activation reagent and/or the vector are distributed more uniformly in a substantially non-yielding chamber compared with a bag.

In some embodiments, the cell engineering system includes a plurality of chambers. In further embodiments, each of the activating, transducing, expanding, concentrating, and harvesting steps of the method for cells described herein is performed in a different chamber of the plurality of chambers of the cell engineering system. In some embodiments, the cells are substantially undisturbed during transfer from one chamber to another. In other embodiments, the steps of the method are performed in the same chamber of the cell engineering system, and the cell engineering system automatically adjusts the chamber environment as needed for each step of the method. Thus further allows for the cells to not be disturbed during the various steps.

In some embodiments, the cell engineering system has improved gas exchange compared with a flexible, gas-permeable bag for cell culture. In some embodiments, the cell engineering system includes gas exchange lines. The gas exchange lines may be made from a gas-permeable material such as, e.g., silicone. In some embodiments, the gas permeability coefficient of the gas exchange lines is higher than the permeability coefficient of the material used in the flexible, gas-permeable bag. In some embodiments, the cell engineering system recirculates oxygen throughout the substantially non-yielding chamber during the cell production methods. Thus, in some embodiments, the oxygen level of a cell culture in the cell engineering system is higher than the oxygen level of a cell culture in a flexible, gas-permeable bag. Higher oxygen levels may be important in the cell culture expansion step, as increased oxygen levels may support increased cell growth and proliferation.

In some embodiments, the cell engineering system continuously recirculates media throughout the chambers without disturbing the cells. For example, the cell engineering system can continuously replenish nutrients, remove waste, and circulate released cytokines and dissolved gases through the chamber, while the cells remain in the same area of the chamber. The continuous circulation can improve the uniform distribution of positive factors and uniform removal of negative factors, which reduces localized effects that are caused by uneven distribution, without disturbing the cells.

In some embodiments, the cell engineering system provides carbon dioxide throughout the chamber during the cell production methods (including CAR T production). $CO_2$ can help to maintain a target pH in the cell culture, which can be important for cell growth and proliferation. In some embodiments, the cell engineering system monitors the $CO_2$ level of the cell culture and adjusts the amount of $CO_2$ provided based on the measured $CO_2$ level. For example, as the cell culture increases, there is a corresponding increase in the amount of $CO_2$ produced by the cells, and the cell engineering system reduces the amount of $CO_2$ provided. The desired $CO_2$ level of the cell culture may be defined by the user, for example, about 1%, about 2%, about 3%, about 4%, about 5%, about 6%, about 7%, about 8%, about 9%, or about 10% $CO_2$. Since the cell engineering system is constantly adjusting the amount of $CO_2$ provided based on the measured $CO_2$ level of the cell culture, the cell engineering system is able to maintain a desired $CO_2$ level throughout the production process. The amount of $CO_2$ in a cell culture may also affect the pH of the culture, since dissolved $CO_2$ generally acidifies a solution (through reacting with water to form carbonic acid). Thus, maintaining a steady $CO_2$ level in the cell culture may result in a more stable pH. Accordingly, in embodiments, the pH level of the cell culture remains substantially constant during the production process. In further embodiments, the pH level of the transduced cell culture remains substantially constant during the expansion step.

Yields from genetically modified immune cell production, including CAR T cell production, may be influenced by activation and transduction efficiency, as well as growth conditions of the cells. Activation efficiency can improve with more stable contact between the cells and the activation reagent. Movement of the cells throughout the culture vessel may lead to an uneven distribution of the cells, and thus create localized effects when activation reagent is added to the cell culture chamber. In contrast to a flexible culture bag, cells grown in a non-yielding chamber remain undisturbed during the activation process, which may contribute to a higher activation efficiency.

Improving activation efficiency may also lead to greater vector transduction efficiency. If cells are activated and are actively dividing, the vector (e.g., lentiviral vector) could integrate more effectively into the cells. Homogeneous distribution of the cells in the cell culture chamber 610 may facilitate homogeneous exposure of the vector to the cells, whereas cells may be unevenly distributed, and thus receive different vector exposure, in a flexible cell culture bag. Thus, in some embodiments, the transduction efficiency of the method for automated production of genetically modified immune cells, including CAR T cells as described herein, is at least 10% greater, at least 15% greater, at least 20% greater, at least 25% greater, at least 30% greater, at least 35% greater, at least 40% greater, at least 45% greater, at least 50% greater, at least 55% greater, at least 60% greater, at least 65% greater, at least 70% greater, at least 75% greater, at least 80% greater, at least 85% greater, at least 90% greater, at least 95% greater, or at least 100% greater than the transduction efficiency of a method utilizing a flexible, gas-permeable bag.

Growth conditions of the cell cultures may also improve cell yields. For example, higher oxygen levels in the cell engineering system, facilitated by highly gas-permeable tubing and continuous recirculation of oxygen in the cell culture chamber, may increase cell proliferation. The ability of the cell engineering system to constantly monitor the state of the cell culture, and make adjustments accordingly, may also be advantageous. For example, the cell engineering system can monitor the $CO_2$ $O_2$, $N_2$, and/or pH level of the cell culture and adjust the level of $CO_2$ $O_2$, or $N_2$. Nutrients can also be provided in a timely and consistent manner and distributed uniformly to the cell culture. Thus, the automated methods for producing genetically modified immune cells, including CAR T cells, described herein advantageously results in higher cell yields compared with manual methods, or methods utilizing a flexible culture bag. Accordingly, in some embodiments, the method for automated production of genetically modified immune cells, including CAR T cells utilizing a cell engineering system as described herein, produces at least 10% more, at least 15% more at least 20% more, at least 25% more at least 30% more, at least 35% more at least 40% more, at least 45% more at least 50% more, at least 55% more at least 60% more, at least 65% more at least 70% more, at least 75% more at least 80% more, at least 85% more at least 90% more, at least 95% more or at least 100% more cells than a method utilizing a flexible, gas permeable bag for cell culture. In embodiments, the number of cells produced by the methods described herein is at least about 2 billion (i.e., $2*10^9$) cells, including at least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, or at least about 3.0 billion cells.

Additional Exemplary Embodiments

Embodiment 1 is a method for automated production of a genetically modified immune cell culture, the method comprising activating an immune cell culture with an activation reagent to produce an activated immune cell culture, transducing the activated immune cell culture with a vector, to produce a transduced immune cell culture, expanding the transduced immune cell culture, concentrating the expanded immune cell culture, and harvesting the concentrated immune cell culture to produce a genetically modified immune cell culture, further comprising washing either or both the expanded immune cell culture and the concentrated immune cell culture, wherein the steps are performed by a fully enclosed cell engineering system and the steps are optimized via a process to produce the genetically modified immune cell culture.

Embodiment 2 includes the method of embodiment 1, wherein the process is a self-adjusting process and includes monitoring with one or more of a temperature sensor, a pH sensor, a glucose sensor, an oxygen sensor, a carbon dioxide sensor, and an optical density sensor; and adjusting one or more of a temperature, a pH level, a glucose level, an oxygen level, a carbon dioxide level, and an optical density of the transduced T cell culture, based on the monitoring.

Embodiment 3 includes the method of embodiments 1-2, wherein the method produces at least about 100 million viable genetically modified immune cells Embodiment 4 includes the method of embodiments 1-3, wherein the method produces at least about 2 billion viable genetically modified immune cells Embodiment 5 includes the method of embodiments 1-4, wherein the immune cell culture is a T cell culture.

Embodiment 6 includes the method of embodiment 5, wherein T cell culture is a chimeric antigen receptor T (CAR T) cell culture.

Embodiment 7 includes the method of embodiment 6, wherein the vector encodes a chimeric antigen receptor.

Embodiment 8 includes the method of embodiments 1-7, wherein the immune cell culture comprises peripheral blood mononuclear cells and/or purified T cells.

Embodiment 9 includes the method of embodiments 1-8, wherein the immune cell culture comprises at least one accessory cell.

Embodiment 10 includes the method of embodiment 9, wherein the accessory cell comprises a monocyte or a monocyte-derived cell.

Embodiment 11 includes the method of embodiment 9, wherein the accessory cell comprises antigens for a T cell receptor, including CD28, CD40, CD2, CD40L and/or ICOS.

Embodiment 12 includes the method of embodiments 1 to 11, wherein the activation reagent comprises an antibody or a dendritic cell.

Embodiment 13 includes the method of embodiment 12, wherein the antibody is immobilized on a surface.

Embodiment 14 includes the method of embodiment 13, wherein the surface is a surface of a bead.

Embodiment 15 includes the method of embodiment 12, wherein the antibody is a soluble antibody.

Embodiment 16 includes the method of embodiments 12-15, wherein the antibody comprises at least one of an anti-CD3 antibody and an anti-CD28 antibody.

Embodiment 17 includes the method of embodiments 1-16, wherein the transducing comprises viral infection, electroporation, membrane disruption, or combinations thereof.

Embodiment 18 includes the method of embodiments 1-17, wherein the vector is a lentiviral vector or a retrovirus.

Embodiment 19 includes the method of embodiments 1-18, wherein the transducing comprises mixing the vector in cell culture media and delivering the vector in the media uniformly to the activated immune cell culture.

Embodiment 20 includes the method of embodiments 1-19, wherein the expanding comprises at least one or more of feeding, washing and monitoring of the transduced immune cell culture.

Embodiment 21 includes the method of embodiments 2-20, wherein the oxygen level of the transduced immune cell culture is optimized for the immune cell culture.

Embodiment 22 includes the method of embodiments 1-21, wherein the cell engineering system recirculates cell culture media through an oxygenation component during one or more of steps (a) to (e).

Embodiment 23 includes the method of embodiments 1-22, wherein the cell engineering system recirculates nutrients, waste, released cytokines, and/or dissolved gasses during steps (a) to (e).

Embodiment 24 includes the method of embodiments 2-23, wherein the carbon dioxide level provided by the cell engineering system decreases during step (c).

Embodiment 25 includes the method of embodiments 1-24, wherein the cell engineering system is configured to perform several rounds of one or more of feeding, washing, monitoring, and selecting of the transduced immune cell culture.

Embodiment 26 includes the method of embodiments 1-25, wherein the concentrating comprises centrifugation, supernatant removal following sedimentation, or filtration.

Embodiment 27 includes the method of embodiment 26, wherein the process further includes adjusting parameters of the centrifugation or filtration.

Embodiment 28 includes the method of embodiments 1 to 27, wherein the cell engineering system comprises a plurality of chambers, and wherein each of steps (a) to (e) is performed in a different chamber of the plurality of chambers of the cell engineering system.

Embodiment 29 includes the method of embodiments 1-28, further comprising removing the activation reagent from the activated immune cell culture after step (a).

Embodiment 30 includes the method of embodiments 1-29, wherein the cell engineering system contains the cell culture of (a), the activation reagent, the vector, and cell culture medium prior to starting the method.

Embodiment 31 is a method for promoting a preferred phenotype of a genetically modified immune cell culture, the method comprising activating an immune cell culture with an activation reagent to produce an activated immune cell culture, wherein the activation reagent and activating conditions promote the phenotype of the genetically modified immune cell culture, transducing the activated immune cell culture with a vector, to produce a transduced immune cell culture, expanding the transduced immune cell culture, concentrating the expanded immune cell culture; and harvesting the concentrated immune cell culture to produce a genetically modified immune cell culture, wherein the steps are performed by a fully enclosed, automated cell engineering system.

Embodiment 32 includes the method of embodiment 31, wherein the activation reagent comprises an antibody or a dendritic cell.

Embodiment 33 includes the method of embodiment 32, wherein the antibody is immobilized on a surface.

Embodiment 34 includes the method of embodiments 33, wherein the surface is a surface of a bead.

Embodiment 35 includes the method of embodiments 32, wherein the antibody is a soluble antibody.

Embodiment 36 includes the method of embodiments 32-35, wherein the antibody comprises at least one of an anti-CD3 antibody, an anti-CD28 antibody and an anti-CD2 antibody.

Embodiment 37 includes the method of embodiment 36, wherein the soluble antibody is OKT3.

Embodiment 38 includes the method of embodiments 31-37, wherein the activating conditions provide a substantially undisturbed immune cell culture allowing for stable contact between the activation reagent and the immune cell culture.

Embodiment 39 includes the method of embodiments 31-38, wherein the method produces at least about 100 million viable genetically modified immune cells Embodiment 40 includes the method of embodiment 39, wherein the method produces at least about 2 billion viable genetically modified immune cells Embodiment 41 includes the method of embodiments 31-40, wherein the immune cell culture is a T cell culture.

Embodiment 42 includes the method of embodiments 41, wherein T cell culture is a chimeric antigen receptor T (CAR T) cell culture.

Embodiment 43 includes the method of embodiments 42, wherein the vector encodes a chimeric antigen receptor.

Embodiment 44 includes the method of embodiments 31-43, wherein the immune cell culture comprises peripheral blood mononuclear cells and/or purified T cells.

Embodiment 45 includes the method of embodiments 31-44, wherein the cell culture comprises at least one accessory cell.

Embodiment 46 includes the method of embodiment 45, wherein the accessory cell comprises a monocyte or a monocyte-derived cell.

Embodiment 47 includes the method of embodiment 45, wherein the accessory cell comprises antigens for a T cell receptor, including CD28, CD40, CD2, CD40L and/or ICOS.

Embodiment 48 includes the method of embodiments 41-47, wherein the phenotype of the T cell culture has a ratio of CD8+ cells to CD4+ of about 0.1:1 to about 10:1.

Embodiment 49 includes the method of embodiments 31-48, wherein the transducing comprises viral infection, electroporation, membrane disruption, or combinations thereof.

Embodiment 50 includes the method of embodiments 31-49, wherein the vector is a lentiviral vector or a retrovirus.

Embodiment 51 includes the method of embodiments 31-50, wherein the transducing comprises mixing the vector in cell culture media and delivering the vector in the media uniformly to the activated immune cell culture.

Embodiment 52 includes the method of embodiments 31-51, wherein the expanding comprises at least one or more of feeding, washing and monitoring the transduced immune cell culture.

Embodiment 53 includes the method of embodiments 31-52, wherein an oxygen level of the transduced immune cell culture is optimized for the promoted phenotype.

Embodiment 54 includes the method of embodiments 31-53, wherein the cell engineering system recirculates cell culture media through an oxygenation component during one or more of steps (a) to (e).

Embodiment 55 includes the method of embodiments 31-54, wherein the cell engineering system recirculates nutrients, waste, released cytokines, and/or dissolved gasses during steps (a) to (e).

Embodiment 56 includes the method of embodiments 31-55, wherein a carbon dioxide level provided by the cell engineering system decreases during step (c).

Embodiment 57 includes the method of embodiments 31-56, wherein the cell engineering system is configured to perform several rounds of the feeding, washing, monitoring, and selecting of the transduced immune cell culture.

Embodiment 58 includes the method of embodiments 31-57, wherein the concentrating comprises centrifugation, supernatant removal following sedimentation, or filtration.

Embodiment 59 includes the method of embodiments 31-58, wherein the cell engineering system comprises a plurality of chambers, and wherein each of steps (a) to (e) is performed in a different chamber of the plurality of chambers of the cell engineering system.

Embodiment 60 includes the method of embodiments 31-59, further comprising removing the activation reagent from the activated immune cell culture after step (a).

Embodiment 61 includes the method of embodiments 31-60, further comprising removing the vector following the transducing in (b).

Embodiment 62 includes the method of embodiments 31-61, wherein the cell engineering system contains the cell culture of (a), the activation reagent, the vector, and cell culture medium prior to starting the method.

Embodiment 63 is a method for automated production of a genetically modified immune cell culture, the method comprising activating an immune cell culture with an activation reagent to produce an activated immune cell culture, transducing the activated immune cell culture with a vector, to produce a transduced immune cell culture, expanding the transduced immune cell culture, concentrating the expanded immune cell culture, and harvesting the concentrated immune cell culture to produce a genetically modified immune cell culture, wherein the steps are performed by a fully enclosed, automated cell engineering system, and wherein each of the steps are performed with immune cell cultures having an optimized cell density (cells/mL) and an optimized cell confluency (cells/cm$^2$).

Embodiment 64 includes the method of embodiment 63, wherein the optimized cell density for (a) is about $0.05*10^6$ cells/mL to about $60*10^6$ cells/mL.

Embodiment 65 includes the method of embodiments 63 or claim 64, wherein the optimized cell confluency for (a) is about $0.1*10^6$ cells/cm$^2$ to about $60*10^6$ cells/cm$^2$.

Embodiment 66 includes the method of embodiments 63-65, wherein the activation reagent comprises an antibody or a dendritic cell.

Embodiment 67 includes the method of embodiment 66, wherein the antibody is immobilized on a surface.

Embodiment 68 includes the method of embodiment 67, wherein the surface is a surface of a bead.

Embodiment 69 includes the method of embodiment 66, wherein the antibody is a soluble antibody.

Embodiment 70 includes the method of embodiments 66-69, wherein the antibody comprises at least one of an anti-CD3 antibody and an anti-CD28 antibody.

Embodiment 71 includes the method of embodiments 63-70, wherein the method produces at least about 100 million viable genetically modified immune cells.

Embodiment 72 includes the method of embodiments 63-71, wherein the method produces at least about 2 billion viable genetically modified immune cells.

Embodiment 73 includes the method of embodiments 63-72, wherein the immune cell culture is a T cell culture.

Embodiment 74 includes the method of embodiments 73, wherein T cell culture is a chimeric antigen receptor T (CAR T) cell culture.

Embodiment 75 includes the method of embodiments 74, wherein the vector encodes a chimeric antigen receptor.

Embodiment 76 includes the method of embodiments 64-75, wherein the immune cell culture comprises peripheral blood mononuclear cells and/or purified T cells.

Embodiment 77 includes the method of embodiments 64-76, wherein the cell culture comprises at least one accessory cell.

Embodiment 78 includes the method of embodiment 77 wherein the accessory cell comprises a monocyte.

Embodiment 79 includes the method of embodiment 77, wherein the accessory cell comprises antigens for a T cell receptor, including CD28, CD40, CD2, CD40L and/or ICOS.

Embodiment 80 includes the method of embodiments 63-79, wherein the transducing comprises viral infection, electroporation, membrane disruption, or combinations thereof.

Embodiment 81 includes the method of embodiments 63-80, wherein the vector is a lentiviral vector or a retrovirus.

Embodiment 82 includes the method of embodiments 63-81, wherein the transducing comprises mixing the vector in cell culture media and delivering the vector in the media uniformly to the activated immune cell culture.

Embodiment 83 includes the method of embodiments 63-82, wherein the expanding comprises at least one or more of feeding, washing, monitoring, and selecting of the transduced immune cell culture.

Embodiment 84 includes the method of embodiments 63-83, wherein an oxygen level of the transduced immune cell culture is optimized for the cell density and cell confluency.

Embodiment 85 includes the method of embodiments 63-84, wherein the cell engineering system recirculates cell culture media through an oxygenation component during one or more of steps (a) to (e).

Embodiment 86 includes the method of embodiment 85, wherein the oxygen recirculation is provided by silicone tubing during steps (a) through (c).

Embodiment 87 includes the method of embodiments 63-86, wherein the cell engineering system recirculates nutrients, waste, released cytokines, and/or dissolved gasses during steps (a) to (e).

Embodiment 88 includes the method of embodiments 63-87, wherein a carbon dioxide level provided by the cell engineering system decreases during step (c).

Embodiment 89 includes the method of embodiments 63-88, wherein the recirculation of nutrients, waste, released cytokines, and/or dissolved gasses is homogenously provided with the cells having a density of about $0.05*10^6$ cells/mL to about $60*10^6$ cells/mL and a confluency of about $0.1*10^6$ cells/cm$^2$ to about $60*10^6$ cells/cm$^2$.

Embodiment 90 includes the method of embodiments 63-89, wherein the cell engineering system is configured to perform several rounds of feeding, washing, monitoring, and selecting of the transduced immune cell culture.

Embodiment 91 includes the method of embodiments 63-90, wherein the concentrating comprises centrifugation, supernatant removal following sedimentation, or filtration.

Embodiment 92 includes the method of embodiments 63-91, wherein the cell engineering system comprises a plurality of chambers, and wherein each of steps (a) to (e) is performed in a different chamber of the plurality of chambers of the cell engineering system.

Embodiment 93 includes the method of embodiments 63-92, further comprising removing the activation reagent from the activated immune cell culture after step (a).

Embodiment 94 includes the method of embodiments 63-93, further comprising removing the vector following the transducing in (b).

Embodiment 95 includes the method of embodiments 63-94, wherein the cell engineering system contains the cell culture of (a), the activation reagent, the vector, and cell culture medium prior to starting the method.

Embodiment 96 is a method for automated production of a genetically modified immune cell culture, the method comprising activating an immune cell culture with an activation reagent to produce an activated immune cell culture, transducing the activated immune cell culture with a vector, to produce a transduced immune cell culture, expanding the transduced immune cell culture, wherein the transduced cell culture is not shaken during the expanding, concentrating the expanded immune cell culture, and harvesting the concentrated immune cell culture to produce a genetically modified immune cell culture, wherein the steps are performed by a fully enclosed, automated cell engineering system.

Embodiment 97 includes the method of embodiment 96, wherein the activation reagent comprises an antibody or a dendritic cell.

Embodiment 98 includes the method of embodiment 97, wherein the antibody is immobilized on a surface.

Embodiment 99 includes the method of embodiment 98, wherein the surface is a surface of a bead.

Embodiment 100 includes the method of embodiment 97, wherein the antibody is a soluble antibody.

Embodiment 101 includes the method of embodiments 96-100, wherein the antibody comprises at least one of an anti-CD3 antibody, an anti-CD28 antibody and an anti-CD2 antibody.

Embodiment 102 includes the method of embodiments 96-101, wherein the method produces at least about 100 million viable genetically modified immune cells Embodiment 103 includes the method of embodiment 102, wherein the method produces at least about 2 billion viable genetically modified immune cells Embodiment 104 includes the method of embodiments 96-103, wherein the immune cell culture is a T cell culture.

Embodiment 105 includes the method of embodiment 104, wherein T cell culture is a chimeric antigen receptor T (CAR T) cell culture.

Embodiment 106 includes the method of embodiment 105, wherein the vector encodes a chimeric antigen receptor.

Embodiment 107 includes the method of embodiments 96-106, wherein the immune cell culture comprises peripheral blood mononuclear cells and/or purified T cells.

Embodiment 108 includes the method of embodiments 96-107, wherein the cell culture comprises at least one accessory cell.

Embodiment 109 includes the method of embodiment 108 wherein the accessory cell comprises a monocyte or a monocyte-derived cell.

Embodiment 110 includes the method of embodiment 109, wherein the accessory cell comprises antigens for a T cell receptor, including CD28, CD40, CD2, CD40L and/or ICOS.

Embodiment 111 includes the method of embodiments 96-110, wherein the transducing comprises viral infection, electroporation, membrane disruption, or combinations thereof.

Embodiment 112 includes the method of embodiments 96-111, wherein the vector is a lentiviral vector or a retrovirus.

Embodiment 113 includes the method of embodiments 96-112, wherein the transducing comprises mixing the vector in cell culture media and delivering the vector in the media uniformly to the activated immune cell culture.

Embodiment 114 includes the method of embodiments 96-113, wherein the expanding comprises at least one or more of feeding, washing, monitoring, and selecting of the transduced immune cell culture, without shaking the immune cell culture.

Embodiment 115 includes the method of embodiments 96-114, wherein an oxygen level of the transduced immune cell culture is optimized for the immune cell culture.

Embodiment 116 includes the method of embodiments 96-115, wherein the cell engineering system recirculates cell culture media through an oxygenation component during one or more of steps (a) to (e).

Embodiment 117 includes the method of embodiments 96-116, wherein the cell engineering system recirculates nutrients, waste, released cytokines, and/or dissolved gasses.

Embodiment 118 includes the method of embodiments 96-117, wherein a carbon dioxide level provided by the cell engineering system decreases during step (c).

Embodiment 119 includes the method of embodiments 96-118, wherein the cell engineering system is configured to perform several rounds of feeding, washing, monitoring, and selecting of the transduced immune cell culture.

Embodiment 120 includes the method of embodiments 96-119, wherein the concentrating comprises centrifugation, supernatant removal following sedimentation, or filtration.

Embodiment 121 includes the method of embodiments 96-120, wherein the cell engineering system comprises a plurality of chambers, and wherein each of steps (a) to (e) is performed in a different chamber of the plurality of chambers of the cell engineering system.

Embodiment 122 includes the method of embodiments 96-121, further comprising removing the activation reagent from the activated immune cell culture after step (a).

Embodiment 123 includes the method of embodiments 96-122, further comprising removing the vector following the transducing in (b).

Embodiment 124 includes the method of embodiments 96-123, wherein the cell engineering system contains the cell culture of (a), the activation reagent, the vector, and cell culture medium prior to starting the method.

Embodiment 125 is a method for automated production of a genetically modified immune cell culture, the method performed by a cell engineering system, comprising, activating an immune cell culture with an activation reagent to produce an activated immune cell culture in a first chamber of the cell engineering system, transducing the activated immune cell culture, the transducing comprising, transferring the activated immune cell culture from the first chamber to an electroporation unit, electroporating the activated immune cell culture with a vector, to produce a transduced immune cell culture, transferring the transduced immune cell culture to a second chamber of the cell engineering system, expanding the transduced immune cell culture, concentrating the expanded immune cell culture; and harvesting the concentrated immune cell culture to produce a genetically modified cell culture.

Embodiment 126 includes the method of embodiment 125, wherein the transducing comprises transferring via a first sterile, closed connection, the activated immune cell culture from the first chamber to the electroporation unit, electroporating the activated immune cell culture with the vector, to produce the transduced immune cell culture, transferring via a second sterile, closed connection, the transduced immune cell culture to the second chamber of the cell engineering system.

Embodiment 127 includes the method of embodiment 126, wherein the electroporation unit is located outside of the cell engineering system.

Embodiment 128 includes the method of embodiments 125-127, wherein the method produces at least about 100 million viable genetically modified immune cells.

Embodiment 129 includes the method of embodiment 128, wherein the method produces at least about 2 billion viable genetically modified immune cells.

Embodiment 130 includes the method of embodiments 125-129, wherein the immune cell culture is a T cell culture.

Embodiment 131 includes the method of embodiment 130, wherein T cell culture is a chimeric antigen receptor T (CAR T) cell culture.

Embodiment 132 includes the method of embodiment 131, wherein the vector encodes a chimeric antigen receptor.

Embodiment 133 includes the method of embodiments 125-132, wherein the immune cell culture comprises peripheral blood mononuclear cells and/or purified T cells.

Embodiment 134 includes the method of embodiments 125-132, wherein the cell culture comprises at least one accessory cell.

Embodiment 135 includes the method of embodiment 134, wherein the accessory cell comprises a monocyte or a monocyte-derived cell.

Embodiment 136 includes the method of embodiments 134, wherein the accessory cell comprises antigens for a T cell receptor, including CD28, CD40, CD40L and/or ICOS.

Embodiment 137 includes the method of embodiments 125-136, wherein the activation reagent comprises an antibody or a dendritic cell.

Embodiment 138 includes the method of embodiments 137, wherein the antibody is immobilized on a surface.

Embodiment 139 includes the method of embodiments 138, wherein the surface is a surface of a bead.

Embodiment 140 includes the method of embodiments 137, wherein the antibody is a soluble antibody.

Embodiment 141 includes the method of embodiments 138-140, wherein the antibody comprises at least one of an anti-CD3 antibody, an anti-CD28 antibody and an anti-CD2 antibody.

Embodiment 142 includes the method of embodiments 125-141, wherein the vector is a lentiviral vector or a retrovirus.

Embodiment 143 includes the method of embodiments 125-142, wherein the expanding comprises at least one or more of feeding, washing, monitoring, and selecting of the transduced immune cell culture.

Embodiment 144 includes the method of embodiments 125-143, wherein an oxygen level of the transduced immune cell culture is optimized for the immune cell culture.

Embodiment 145 includes the method of embodiments 125-144, wherein the cell engineering system recirculates cell culture media through an oxygenation component during one or more of steps (a) to (e).

Embodiment 146 includes the method of embodiments 125-145, wherein the cell engineering system recirculates nutrients, waste, released cytokines, and/or dissolved gasses during steps (a) to (e).

Embodiment 147 includes the method of embodiments 125-146, wherein a carbon dioxide level provided by the cell engineering system decreases during step (c).

Embodiment 148 includes the method of embodiments 125-147, wherein the cell engineering system is configured to perform several rounds of feeding, washing, monitoring, and selecting of the transduced immune cell culture.

Embodiment 149 includes the method of embodiments 125-148, wherein the concentrating comprises centrifugation, supernatant removal following sedimentation, or filtration.

Embodiment 150 includes the method of embodiments 125-149, wherein the cell engineering system comprises a plurality of chambers, and wherein each of steps (a) to (e) is performed in a different chamber of the plurality of chambers of the cell engineering system.

Embodiment 151 includes the method of embodiments 125-150, further comprising removing the activation reagent from the activated immune cell culture after step (a).

Embodiment 152 includes the method of embodiments 125-151, further comprising removing the vector following the transducing in (b).

Embodiment 153 includes the method of embodiments 125-152, wherein the cell engineering system contains the cell culture of (a), the activation reagent, the vector, and cell culture medium prior to starting the method.

Embodiment 154 includes the method of embodiments 1 to 153, wherein transduction efficiency in step (c) of the method is at least 20% higher than the transduction efficiency of the method utilizing a flexible, gas permeable bag for cell culture.

Embodiment 155 includes the method of embodiments 1 to 154, wherein the method produces at least 20% more genetically modified immune cells than a method utilizing manual cell culture with a flexible, gas permeable bag.

Embodiment 156 includes the method of embodiments 1 to 155, wherein the cell engineering system comprises a plurality of chambers, and wherein each of steps (a) to (e) is performed in a different chamber of the plurality of chambers of the cell engineering system, each of (a), the activation reagent, the vector, and cell culture medium are contained in a different chamber of the plurality of the chambers prior to starting the method, and wherein at least one of the plurality of chambers is maintained at a temperature for growing cells and at least one of the plurality of chambers is maintained at a refrigerated temperature.

Embodiment 157 is a cassette for use in an automated cell engineering system, comprising a low temperature chamber, for storage of a cell culture media, a high temperature chamber for carrying out activation, transduction and expansion of an immune cell culture, wherein the high temperature chamber is separated from the low temperature chamber, by a thermal barrier, the high temperature chamber including a cell culture chamber; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber.

Embodiment 158 includes the cassette of embodiment 157, wherein the cell culture chamber is flat and non-flexible chamber, having a low chamber height.

Embodiment 159 includes the cassette of embodiments 157 or 158, wherein the cell culture chamber is oriented so as to allow the immune cell culture to spread across the bottom of the cell culture chamber.

Embodiment 160 includes the cassette of embodiments 157-159, wherein the cassette is pre-filled with cell culture, culture media, activation reagent, and a vector.

Embodiment 161 includes the cassette of embodiments 157-160, further comprising one or more of a pH sensor, a glucose sensor, an oxygen sensor, a carbon dioxide sensor, and/or an optical density sensor.

Embodiment 162 includes the cassette of embodiments 157-161, further comprising one or more sampling ports and/or injection ports.

Embodiment 163 includes the cassette of embodiments 157-162, wherein the cell culture chamber further comprises at least one of a distal port configured to allow for the removal of air bubbles from the cell culture chamber and/or as a recirculation port; a medial port configured to function as a recirculation inlet port; and a proximal port configured to function as a drain port for cell removal.

Embodiment 164 includes the cassette of embodiments 157-163, further comprising an access port for connecting the cartridge to an external device.

Embodiment 165 includes the cassette of embodiment 164, wherein the external device includes an electroporation unit or an additional media source.

Embodiment 166 is cassette for use in an automated cell engineering system, comprising a cell culture chamber for carrying out activation, transduction and/or expansion of an immune cell culture having a chamber volume that is configured to house an immune cell culture, a satellite volume for increasing the working volume of the chamber by providing additional volume for media and other working fluids without housing the immune cell culture, wherein the satellite volume is fluidly connected to the cell culture chamber via one or more fluidics pathways such that media is exchanged with the culture chamber without disturbing the immune cell culture.

Embodiment 167 includes the cassette of embodiment 166, wherein the satellite volume is a bag.

Embodiment 168 includes the cassette of embodiment 166, wherein the satellite volume is a non-yielding chamber.

Embodiment 169 includes the cassette of embodiments 166-168, wherein the satellite volume is further configured to allow media removal without loss of cells of the immune cell culture.

Embodiment 170 includes the cassette of embodiments 166-169, further comprising a crossflow reservoir.

Embodiment 171 includes the cassette of embodiments 166-170, wherein the cell culture chamber has a volume of between about 0.50 ml and about 300 ml.

Embodiment 172 includes the cassette of embodiment 171, wherein the cell culture chamber has a volume of between about 50 ml and about 200 ml.

Embodiment 173 includes the cassette of embodiment 172, wherein the cell culture chamber has a volume of about 180 ml.

Embodiment 174 includes the cassette of embodiments 166-173, wherein the satellite volume is between about 0.50 ml and about 300 ml.

Embodiment 175 includes the cassette of embodiment 174, wherein the satellite volume is between about 150 ml and about 200 ml.

Embodiment 176 includes the cassette of embodiments 166-175, wherein the crossflow reservoir has a volume of between about 0.50 ml and about 300 ml.

Embodiment 177 includes the cassette of embodiments 176, wherein the crossflow reservoir has a volume of between about 100 ml and about 150 ml.

Embodiment 178 includes the cassette of embodiments 166-177, wherein the working volume is about 180 mL to about 1 L.

Embodiment 179 includes the cassette of embodiment 178, wherein the working volume is about 180 mL to about 460 mL.

Embodiment 180 includes the cassette of embodiments 157-179, wherein one or more of the fluidic pathways comprise a silicone-based tubing component that allows oxygenation through the tubing component.

EXAMPLES

Example 1— Automated Production of CAR T Cells Using the COCOON™ System

In this Example, GFP and HER-2 lentivirus were used to transduce T cells using the following process parameters: starting inoculation of 60 million peripheral blood mononuclear cells (PBMC), CD3/CD28 activation, IL-2 and IL-7 were supplemented into T-cell growth media for culture expansion. Single-use sensors in the disposable cassette were used to monitor temperature, pH and optical density (OD) in real time. The multiple cassette chambers that are connected via fluidic channels enabled automated feeding and addition of process components. Some of the chambers are temperature controlled at 4° C. for media and reagent storage, while others included elements for warming, mixing, washing, and concentrating cells, allowing for a fully enclosed process. The in-process samples were drawn for cell counts and viability. At the end of the harvesting process, FACS analysis was performed with the following panel: CD4, CD8, NGFR, IFN-γ, TNF-α, etc. An overview of the COCOON™ System used in this Example is shown in FIG. 6. FIG. 6A shows the COCOON™ system in the closed configuration along with an external user control display, which can be used to adjust parameters or monitor the cell culture. Sterile, single-use cell culture "cassettes" can be loaded into the COCOON™ (FIG. 6C). As shown in a detailed view of the cassette (FIG. 6B), each cassette includes an upper chamber maintained at 37° C. for growing cells, and a lower chamber maintained at 4° C. for storing media, viral vector, and other temperature-sensitive reagents. The cassette is configured such that fluids can be exchanged through the interior fluidics pathways, and also pumped into or out of the cassette. Sensors installed in the cassette can monitor, e.g., the pH and optical density of the cell culture.

Results are shown in FIGS. 7-10. FIGS. 7A, 7B, and 7C show, respectively, the average harvest yields, average harvest viability, and average transduction efficiency for GFP transduction using the automated COCOON™ System, compared with manual manipulation and expansion of the cells using the G-REX (WilsonWolf) cell culture plates as control. The G-REX plates have gas-permeable bottoms, and media exchange is typically performed by the user every 4 to 5 days when using the G-REX.

Figure 8A:
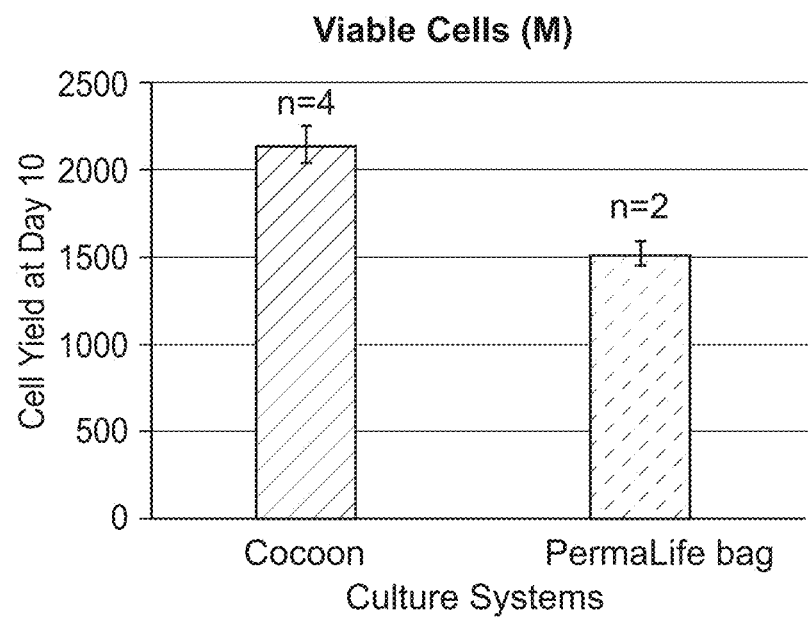
FIGS. 8A-8B show results of experiments described in Example 1, comparing HER-2 CAR T transduction in the COCOON™ system and PERMALIFE™ bag.
Figure 8B:
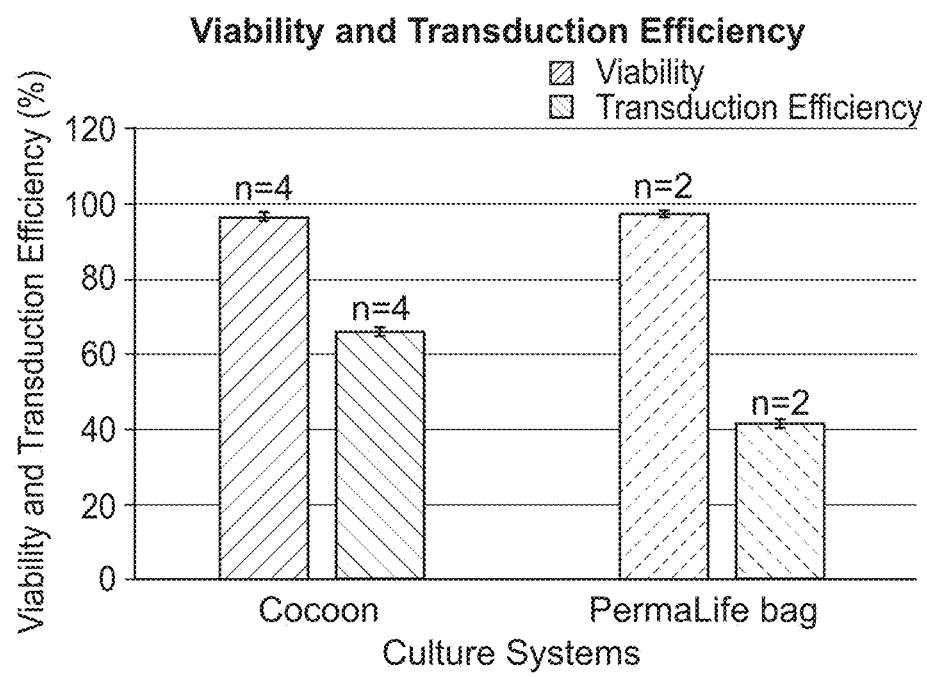

FIGS. 8A and 8B show, respectively, the viable cells and the viability and transduction efficiency for HER-2 CAR-T transduction. In 10-day cultures, the HER-2 CAR-T cells reached approximately 2.2 billion with viability of 97% and transduction of 65% (n=4) in the COCOON™ system.

Figure 9A:
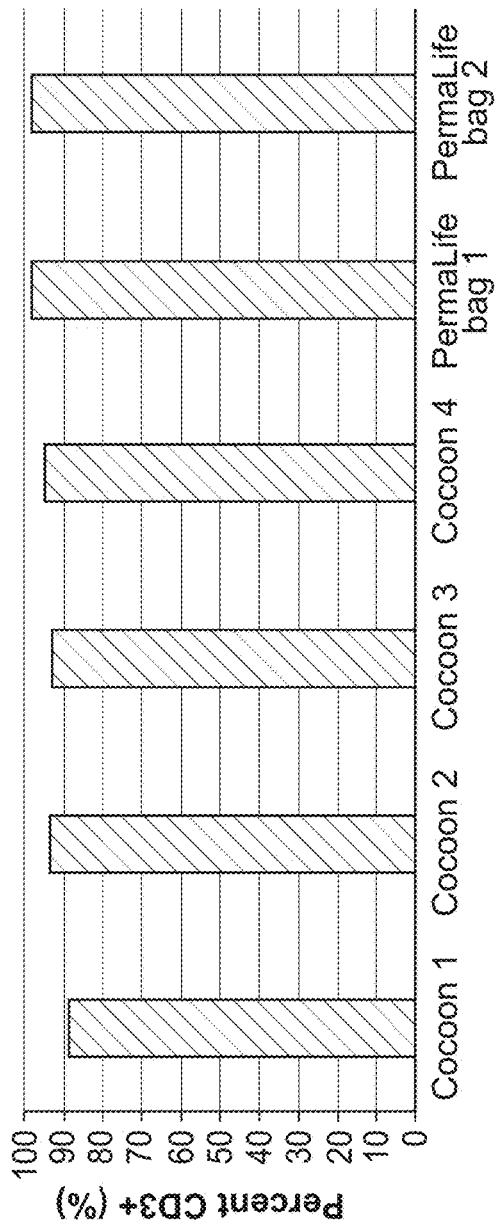
FIGS. 9A-9D show results of experiments described in Example 1, comparing the COCOON™ system and PERMALIFE™ bag.
Figure 9B:
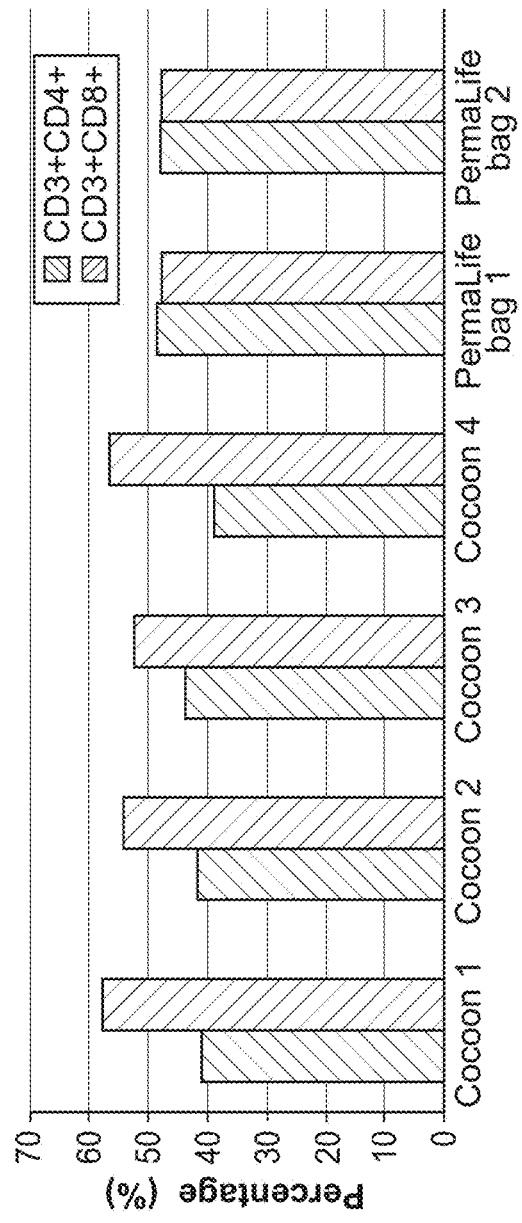
Figure 9C:
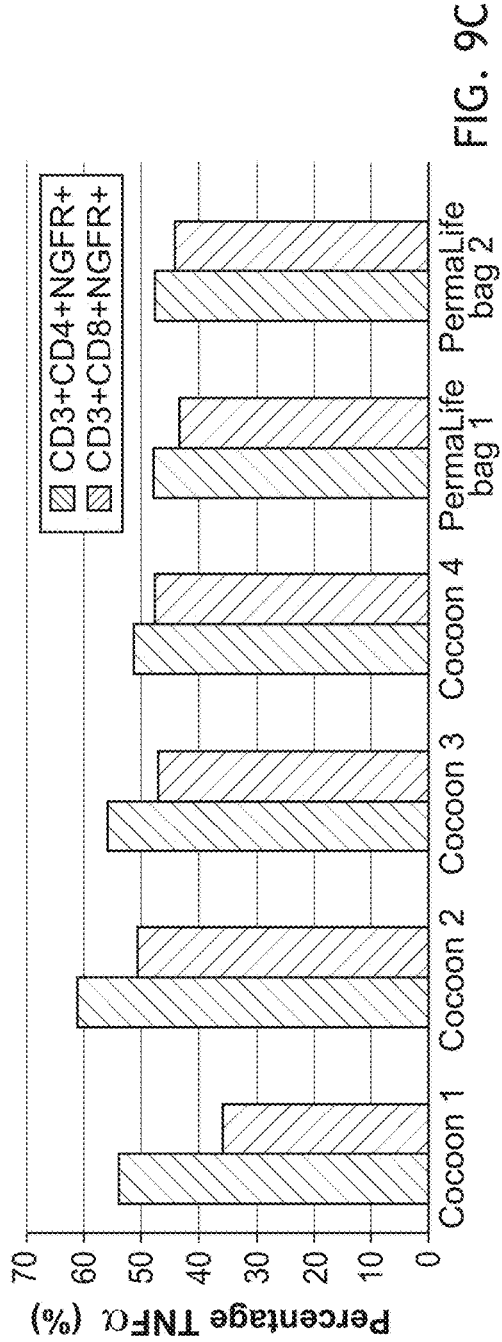
Figure 9D:
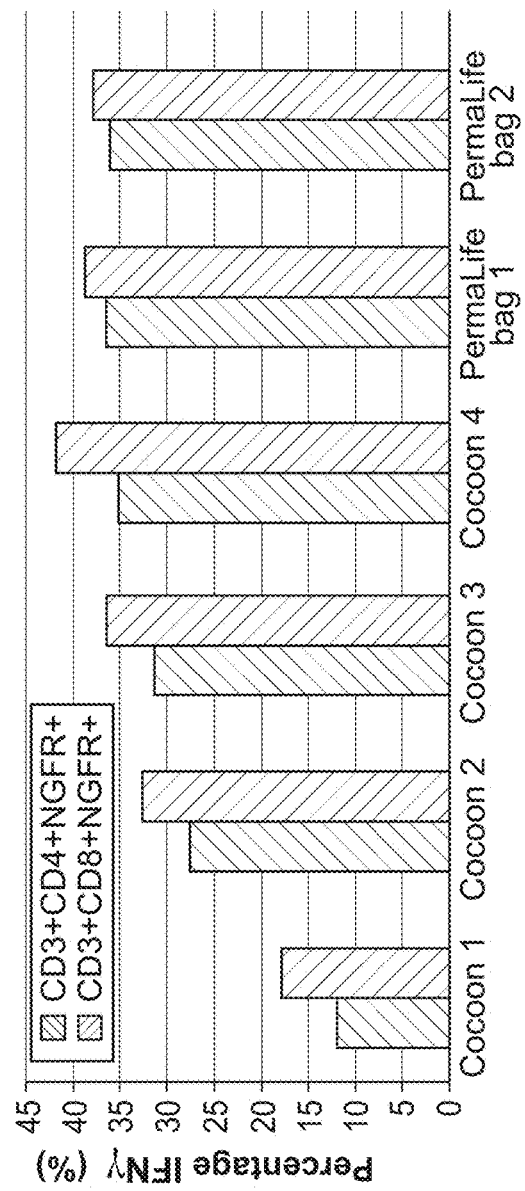

Performance of the automated COCOON™ System was also compared with manual manipulation and growth of cells using the PERMALIFE™ Cell Culture Bag (OriGen) as a control. The PERMALIFE™ Bag is a sealable and gas-permeable cell culture bag made of inert fluorinated ethylene propylene (FEP), with valves to facilitate cell feeding and harvest by the user. FIG. 9A indicates the relative T Cell purity level using the COCOON™ System compared with the PERMALIFE™ Bag, as assessed by the percentage of CD3+ cells. FIG. 9B shows a greater percentage of CD8+ cells cultured in the COCOON™ System compared with the PERMALIFE™ Bag control. FIGS. 9C and 9D show that transfected cells produce TNF-α and INF-γ, respectively.

FIGS. 10A and 10B show effective and specific killing of target tumor cells by CAR T cells cultured in the COCOON™ System and the PERMALIFE™ Bag, respectively.

In conclusion, the COCOON™ System, a fully enclosed cell engineering system, is a viable solution to translate the labor-intensive CAR T process into a fully automated and highly controlled system, thus allowing scalability, high yield, reduction of manufacturing cost, and gaining better process control to yield high quality CAR-T cells.

Example 2—Comparison of Activation Methods in the COCOON™ System

This Example compares cell culture performance using different methods of activation in the clinical scale production of CAR T cells in the COCOON™ automated manufacturing system and a PERMALIFE™ Bag.

Magnetic anti-CD3/anti-CD28 DYNABEAD(S)™ activator beads may be used to activate T cells. These beads provide the two necessary stimulatory signals to support effective T cell activation. Another method of activating naïve T cells may utilize a soluble anti-CD3 antibody (OKT3). OKT3 is a monoclonal IgG2a antibody, originally used as an immunosuppressant. The costimulatory signals can be provided by accessory cells. Initiating T cell culture from a mixed population of peripheral blood mononuclear cells (PBMC) can provide the necessary accessory cells to support T cell activation when using OKT3.

As OKT3 and DYNABEAD(S)™ utilize distinct activation mechanisms, the selection of one method over the other could influence the final product characteristics; specifically, the ratio of T cell subsets, CD4+ helper T cells and CD8+ cytotoxic T cells. The cytotoxic CD8 T cells are responsible for the anti-tumor response. CD4 cells produce cytokines and help to regulate the immune response. It has been demonstrated that CD4 cells also support cell lysis, although the killing is delayed compared to CD8 cells. CD4 cells signal to APCs, thus activating APCs and subsequently priming naïve CD8 T cells. The ideal target ratio of CD8 to CD4 cells is not well understood due to limited clinical data. Studies have shown that a combination of CD8 and CD4 cells are preferred over the delivery of CD8 cells alone (see, e.g., Church 2014; Feldmann 2012; Reusch 2015).

There are advantages and disadvantages of both methods of in vitro activation. Antibody-bound beads offer consistency and ensure stable simultaneous activation of the TCR/CD3 complex as well as the CD28 co-stimulatory pathway. A major disadvantage of the bead approach is the high cost associated with this product. The beads must also be effectively removed from culture before implantation. OKT3 offers a low-cost option for activating T cells. The major disadvantages associated with the soluble anti-CD3 approach are the dependency on accessory cells and sensitivity to the culturing environment. Patient samples may have highly variable accessory cells and negative interactions that might functionally inactivate the T cells after previous stimulation. To understand the impact of each method of activation on the growth, phenotype and functionality of the cells, T cells activated by DYNABEAD(S)™ and OKT3 were cultured in a clinical-scale automation platform.

COCOON™ provides the environmental control of gases and temperatures. This includes a 37° C. zone as well as a linked refrigerated zone. There is no fluid contact between the COCOON™ and the Cassette, minimizing the required cleaning between runs. All reagents can be loaded into the Cassette on the day of seeding and stored in the refrigerated zone of the COCOON™ until needed. Fluid is warmed to 37° C. before delivery to the cells. Due to the stability of lentivirus, this can be thawed on the day of transduction and delivered into the Cassette via sterile connectors. Gas exchange (oxygenation and $CO_2$ buffering) is achieved via recirculation of the culture fluid through gas permeable tubing. Embedded biosensors provided real-time data on dissolved oxygen and pH. As the T cells require stable contact with other cells or the activating agent, media exchanges, washing and recirculation for gas exchange can be performed via perfusion without disturbing the cells. Rocking can be used to facilitate efficient harvesting.

Methods

Cell Culture. Peripheral blood mononuclear cells (PBMC) (Lonza) were thawed with DNase (Sigma) and allowed to recover overnight at 37° C. at a density of $<2\times10^6$ cells/mL. Cell counting was performed using the NUCLEOCOUNTER® with the Blood Assay protocol, including Solution 17 (Chemometec). A third-generation lentiviral vector, encoded with a low affinity nerve growth factor receptor (NGFR) as a marker of transduction, was used to transduce the cells. This lentivirus was manufactured at Lonza's cGMP virus manufacturing facility (Houston, Texas) based on a protocol and primers originating from the Bramson Lab at McMaster University (Hamilton, Canada). A multiplicity of infection (MOI) of 1 was used in all conditions. The viral titer was determined by using HEK293TM cells and detection of NGFR using flow cytometry. Activation media consisted of X-VIVO™ 15 (Lonza) supplemented with 22 IU/mL IL-2 (Cedarlane) and 1% penicillin-streptomycin (Sigma). In conditions activated with soluble anti-CD3, OKT3 (Biolegend) was added to the activation media for a final concentration of 50 ng/mL. In conditions activated with DYNABEAD(S)™, a ratio of 1:1 beads to cells was added to the activation media. Expansion media consisted of X-VIVO™ 15 (Lonza) supplemented with 29 IU/mL IL-2 (Cedarlane), 5% human serum from male AB plasma (Sigma), 1% GLUTAMAX™ (Thermo Fisher) and 1% penicillin-streptomycin (Sigma).

Automated CAR T Cell Production. On Day 0, $60\times10^6$ PBMC were loaded into the input bag of the Cassette. In conditions activated using anti-CD3/anti-CD28 beads, $60\times10^6$ anti-CD3/anti-CD28 DYNABEAD(S)™ (ThermoFisher) were also added to the input bags for a ratio of 1:1 beads to cells. The input bag was connected to the Cassette and brought to the COCOON™ (Octane Biotech Inc.). Following operator sign-in, the Cassette was loaded into the COCOON™. On Day 1, virus (Lonza Houston) was thawed and then transferred to the cell culture chamber via the Cassette access port at a MOI of 1. Prior to delivery of the virus to the cells, activation media was used to dilute the media. The activation media was removed from the culture chamber and returned with the virus without disturbing the cells. The total working volume was increased on Day 4 with the addition of expansion media. Partial media exchanges were performed with expansion media on Day 6 and Day 8. Following the expansion steps, the COCOON™ decreased the final volume to less than 100 mL before the cells were removed. Throughout the culture, data was continuously collected by the COCOON™. This included every pump and actuator step, each time the door was opened and closed and so forth. Comprehensive sensor data was collected including thermal values, gas concentrations, fluid pH and dissolved oxygen. The operator was able to remotely monitor the status of the culture using a phone or external computer.

Manual CAR T Cell Production. Manual production of CAR T cells was performed in parallel to COCOON™ in PERMALIFE™ cell culture bags. On Day 0, $60\times10^6$ PBMC were seeded in activation media at $0.27\times10^6$ cells/mL on Day 0. These cultures utilized the same donor cells as well as the same media for activation and expansion as the automated cultures. Cultures were initiated in PERMALIFE™ bags (PL240, Origen) and were transferred to larger PERMALIFE™ bags on Day 6 (PL325, Origen) as the cells expanded. Cells were expanded into PL240 and PL325 bags on Day 8 as the volume increased. On Day 1, lentivirus was added to the bags at a MOI of 1. Cells were fed with an equivalent volume as COCOON™ cultures; however, unlike the COCOON™ conditions, no media was sent to waste. The volume used maintained the cultures at less than $2\times10^6$ cells/mL. On Day 10, culture volumes were obtained by mass and a sample of the total cells was removed from the bags for counting and analysis. The cells were centrifuged to reduce the residuals as well as the volume before use in functional assays.

Non-Transduced and Non-Activated Conditions. Non-transduced and non-activated negative controls used for fluorescence activated cell sorting (FACS) analysis were cultured at a small scale according to protocols previously described. Briefly, $1\times10^6$ cells were seeded in 96 well plates with X-VIVO™ 15 (Lonza) supplemented with 5% human AB serum (Sigma) and 22 ng/mL IL-2 (Cedarlane). Activated, but non-transduced controls were set up using a similar protocol. After the cells were seeded, an equal volume of media was added. Conditions activated with soluble anti-CD3 were supplemented with 100 ng/mL OKT3 (Biolegend) for a final concentration of 50 ng/mL. Conditions activated with anti-CD3/anti-CD28 beads had DYNABEAD(S)™ added at a ratio of 1:1. Activated cultures were expanded from 96 well plates to 24 well on Day 4 and transferred into T25 and T75 flasks based on their growth and fed every two days from Day 4.

Flow Cytometry. To phenotype starting populations, cells were stained with the following primary antibodies: Pacific blue CD3 (clone UCHT1, BD Biosciences), PE CD14 (clone 61D3, ThermoFisher), APCeFluor780 CD4 (clone OKT4, ThermoFisher), PerCP-Cy5.5 CD8a (clone RPA-T8, ThermoFisher), BV605 CD279 (PD-1, clone EH12.2H7 BioLegend) and LIVE/DEAD™ Fixable Violet Dead Cell Stain (ThermoFisher). To assess the efficiency of HER2 transduction, cells were stained as above except instead of staining for monocytes (CD14), cells were stained with BV421 CD271 (C40-1457 NGFR, BD Biosciences) and LIVE/DEAD™ Fixable Green Dead Cell Stain (ThermoFisher). Cells were then fixed and washed. Greater than 20,000 events were acquired per condition on a SA3800 Sony Spectral Analyzer. FACS analysis was performed using FlowJo 10.4.2. Non-transduced and non-activated conditions were used to set gates along with fluorescence minus one (FMO) controls.

Tumor Cell Lines. HER2 negative tumor cells, LOX-IMVI cells (National Cancer Institute), derived from metastatic amelanotic melanoma were expanded in RPMI (Sigma) with 10% FBS (Sigma) as previously described. HER2 positive tumor cells, SKOV-3 (ATCC) cells, derived from an ovarian serous cystadenocarcinoma were expanded in McCoy's 5a (modified) media (ThermoFisher) with 10% FBS as previously described. Cells were passaged before confluence using 0.25% trypsin for 5 to 10 minutes. Low passage numbers were cryopreserved and tumor lines were passaged 2 to 3 times before use in ALAMARBLUE™ or ICS assays.

Cytokine Secretion Assay. As previously described (e.g., Atkuri 2005; Avgoustiniatos 2008), 50,000 LOX IMVI or SKOV-3 tumor cells were seeded in triplicate for each culture condition into round bottom 96 well plates. The following day, T cells were seeded at 8:1 per well of the tumor lines with a protein transport inhibitor brefeldin A (Golgi Plug, BD Biosciences) for 4 hours at 37° C. Cells were stored at 4° C. overnight. Cells were then pooled for staining and analysis. As described above, cells were stained for surface phenotype CD3, CD4, CD8a, NGFR, and LIVE/DEAD™ Fixable Green Dead Cell Stain. Intracellular cytokine staining (ICS) was completed following fixation and permeabilization with BD CYTOFIX/CYTOPERM™ Fixation/Permeabilization Solution Kit (554714, BD Biosciences). Activated cytokines tested include APC IFNγ(clone B27, BD Biosciences) and PE TNFα (clone MAb11, BD Biosciences). More than 230,000 events (maximum 500,000) were collected on the Sony SA3800 for ICS analysis. The difference between production of cytokines on SKOV-3 and LOX-IMVI tumor lines was reported as the percentage of the population secreting TNFα or IFNγ. Non-transduced and non-activated conditions were used to set gates along with FMO controls.

Cytotoxicity Assay. Cytotoxicity was tested as previously described (e.g., Atkuri 2005; Avgoustiniatos 2008). Adherent tumor cell lines were plated at $2 \times 10^4$ cells/well (SKOV-3 or LOX-IMVI) overnight in 96-well flat bottom tissue culture treated plates. CAR T cells from the COCOON™ and control conditions were added to wells of tumor cells at various effector (E) T cells to tumor (T) E:T ratios (from 0.25:1 to 8:1) and co-incubated overnight at 37° C. Wells were washed three times with warmed PBS or RPMI media to remove any non-adherent cells. 100 μL of a 10% solution of ALAMARBLUE™ cell viability reagent (Life Technologies) was added and wells were incubated at 37° C. for 3 hours. ALAMARBLUE™, a metabolic indicator of viable cells that fluoresces upon mitochondrial reduction, was measured by fluorescence (excitation 530 nm, emission 595 nm) on a Tecan Infinite M200 Pro plate reader (Tecan, Maennendorf, Switzerland). Tumor cell viability was calculated as the loss of fluorescence in experimental wells compared to untreated target cells. Each condition was tested in triplicate.

Results

Figure 11F:
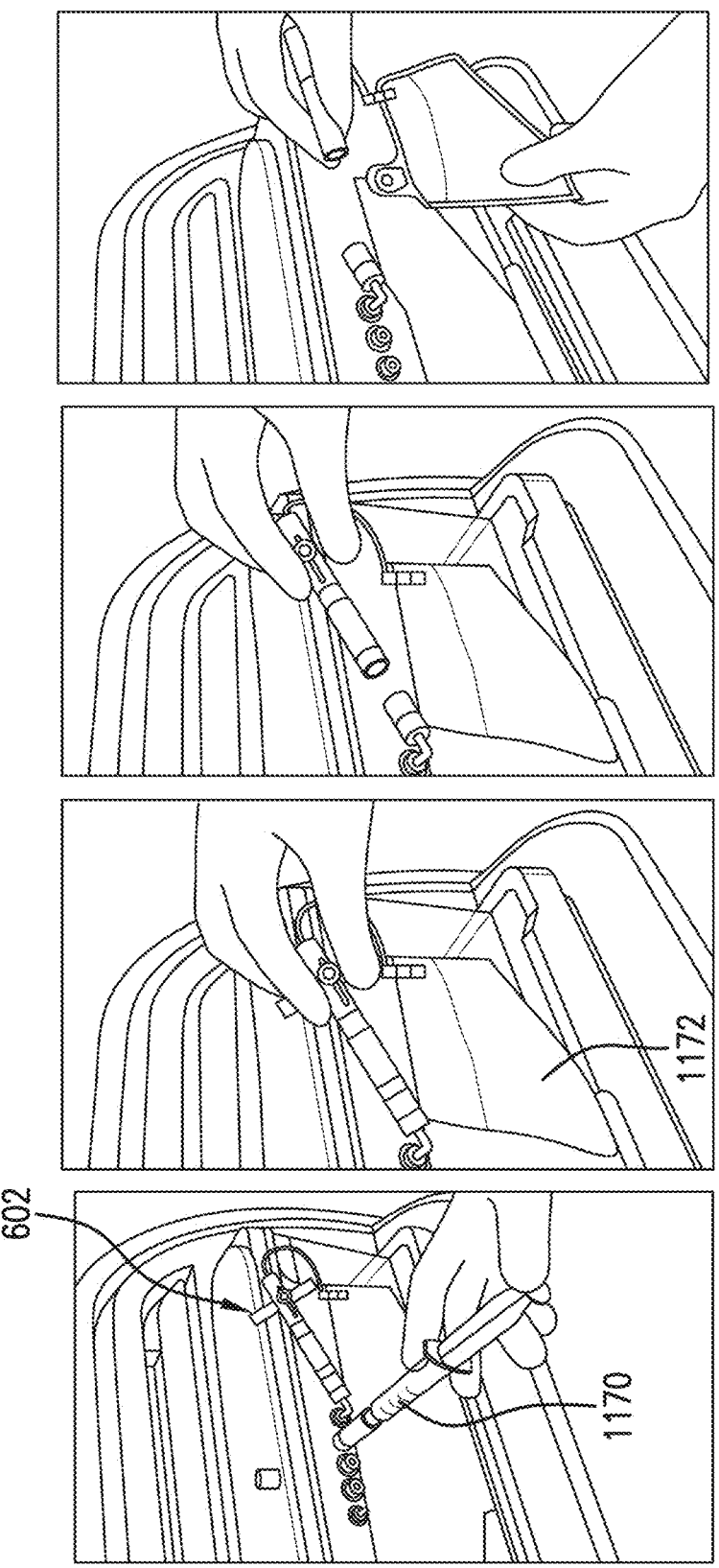
FIG. 11F shows the use of a syringe and a bag to sample from the cassette.

The automation platform, COCOON™, was utilized to demonstrate the feasibility in achieving clinical-scale production of CAR T cells using two different activation methods. The platform consists of a single-use disposable COCOON™ Cassette (FIG. 11A, 11E) and a COCOON™ control system (FIG. 11B). FIG. 11F shows how a syringe 1170 or bag 1172 can be used for cassette 602 sampling. The cassette is designed with multiple reagent bags to enable all reagents required for the process to be pre-loaded and stored in the refrigerated zone of the cassette with cell processing occurring in the culture zone. The cassette supports multiple unit operations linked as a closed system, including cell activation, transduction, expansion, real-time dissolved oxygen and pH monitoring, washing, and cell concentration. The lower portion of the Cassette contains multiple bags to hold the various reagents and waste required for the culture. COCOON™ provides the control system for cassettes. This includes control of fluid and cell transfers, as well as rocking, agitation and remote monitoring of control sensors. Actuators enable automated valve control without fluid contact. Without actuator interaction, valves remain closed enabling the cassette to be moved between rooms or to a microscope while preventing uncontrolled fluid movement. After loading the required reagents into the fluid reservoir of the Cassette, it is snapped on to the culture zone of the Cassette in which various unit operations occur. Sterile sample removal or injection of virus utilizes ICU Spiros connectors. Prior to sample removal or virus addition, the operator is promoted at a specific time, as defined in the pre-programmed protocol. Following operator sign-in and acknowledgment of the notification, the COCOON™ automatically opens to enable sample removal or virus addition. The operator acknowledges that the action has been completed before the door automatically closes and environmental control resumes. When the Cassette is loaded into the COCOON™ (FIG. 11C) and the outer shell is closed (FIG. 11D), the lower portion of the Cassette is separated from the upper portion by a thermal barrier. The lower portion is maintained at refrigerated temperatures and the upper portion is maintained at 37° C. The closed COCOON™ enables gas and thermal control. Cells are maintained at 37° C. while reagents are maintained in a cold zone to prolong stability. The opaque shell prevents light-induced toxicity related to the breakdown of media components. A pre-warming chamber is located in the 37° C. zone to warm media before it is transferred to the cells. All culture steps can be automated from the PBMC loading to the final concentration and cell collection. As shown in FIG. 11A, the Cassette has a series of access ports which can be used for loading the virus following activation. Real time dissolved oxygen and pH sensors are incorporated into the Cassette to provide feedback to the COCOON™ software. Real time data as well as historical graphs can be monitored to ensure that these factors were maintained within the target ranges.

Figure 12A:
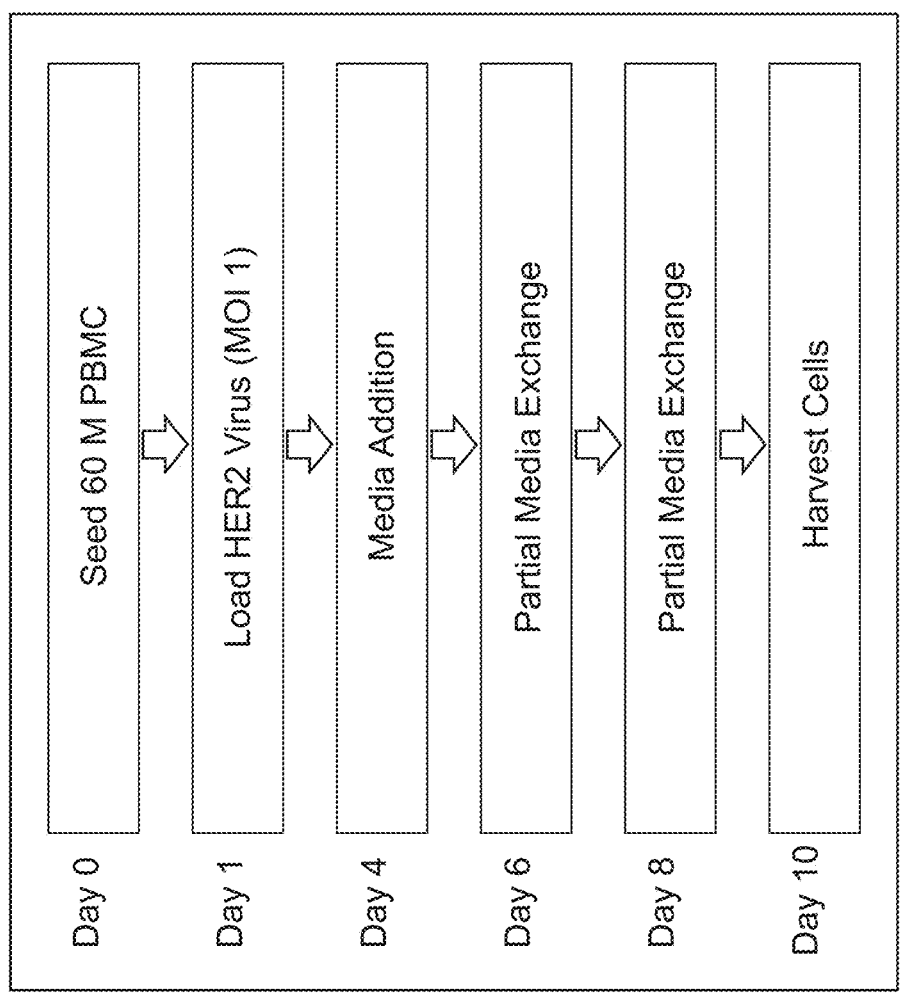
FIG. 12A shows a process overview for the CAR T cell production process.
Figure 12B:
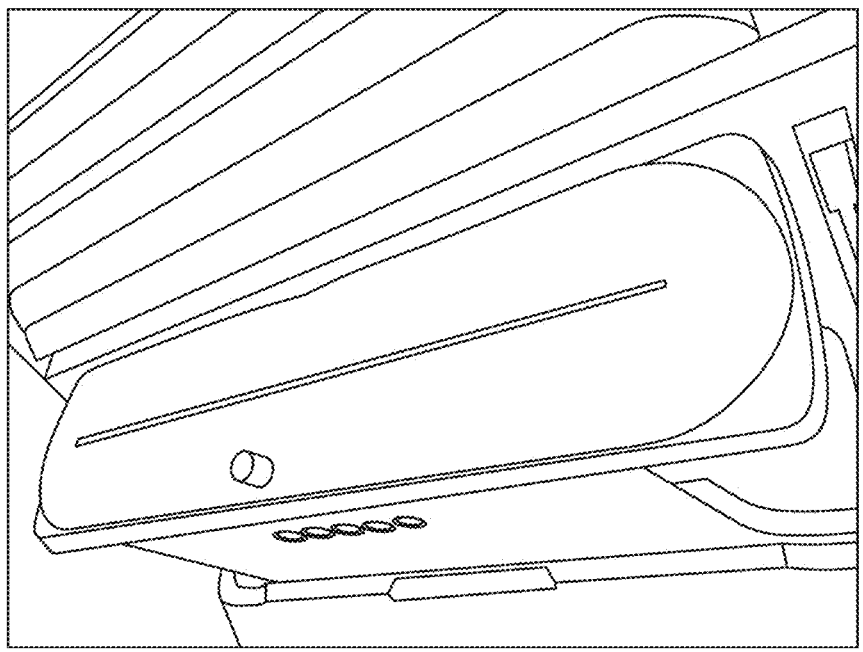
FIG. 12B shows a COCOON™ cassette cell proliferation chamber with a CAR T cell culture in progress.
Figure 12C:
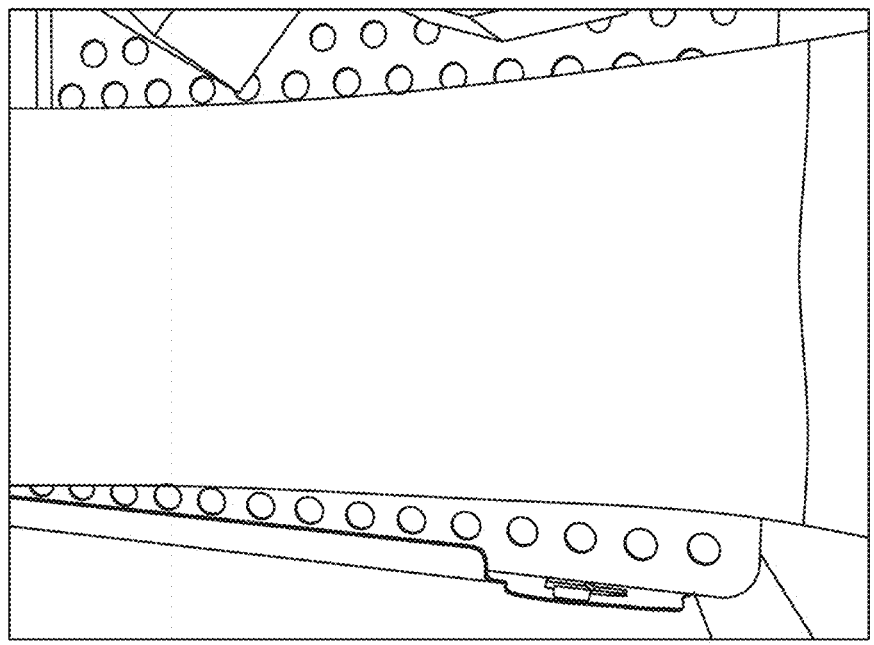
FIG. 12C shows a manually manipulated CAR T cell production process using a cell culture bag in an incubator.

An overview of the COCOON™ process steps is shown in FIG. 12A. Gas permeable PERMALIFE™ bags were used for parallel control cultures and the expansion of CART cells (e.g., Lu 2016). FIGS. 12B (COCOON™) and 12C (PERMALIFE™ bag) demonstrate the cell distribution in the two formats with the cells in the COCOON™ cultured in the top chamber of Cassette. An equivalent volume of media was used for both systems. The PERMALIFE™ cell culture bag utilized a fed batch process, with the area expanded as total volume increased, as is commonly performed. The COCOON™ Cassette utilized a fixed area, employed an initial fed batch feeding strategy and then used partial media exchanges on Day 6 and Day 8 of culture.

To assess the impact of the activation method and the performance of the automated platform, the following criteria were used: viability, cell number, phenotype, exhaustion, transduction efficiency, functional intracellular cytokine secretion, and cytotoxicity. Results are summarized in FIG. 16 and discussed herein.

The same donor cells were used for all conditions, unless otherwise indicated as Donor 2. All conditions were seeded with $60 \times 10^6$ PBMC and fed with the same media volume and composition. The starting cell population contained 66.6% CD3+ T cells and 12.0% CD14+ cells. Of the CD3+ cells, 71.2% were CD4+ and 28.1% were CD8+ cells. A second donor was used to determine the impact of donor-to-donor variability. This second population of PBMC originally contained 75.0% CD3+ T cells and 4.5% CD14+ cells. Of the CD3+ cells, 65.0% were CD4+ and 32.9% were CD8+ cells.

Figure 13A:
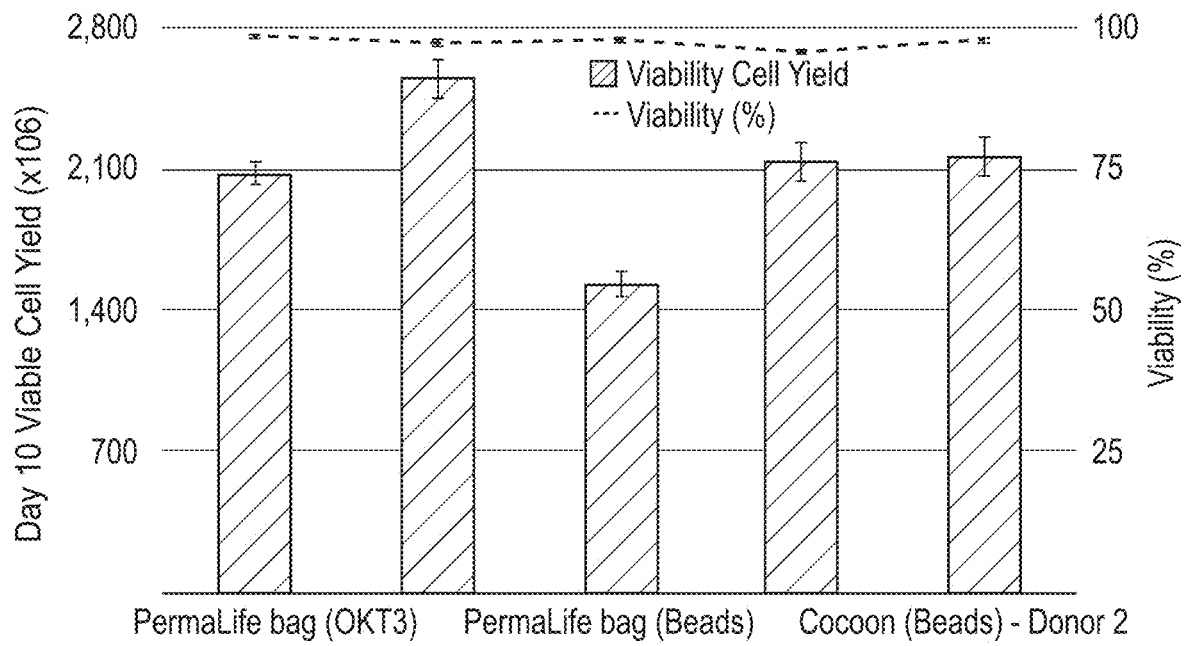
FIGS. 13A-13H show results of experiments described in Example 2, comparing the PERMALIFE™ bag and COCOON™ system, as well as T cell activation by DYNABEAD(S)™ or OKT3.
Figure 13B:
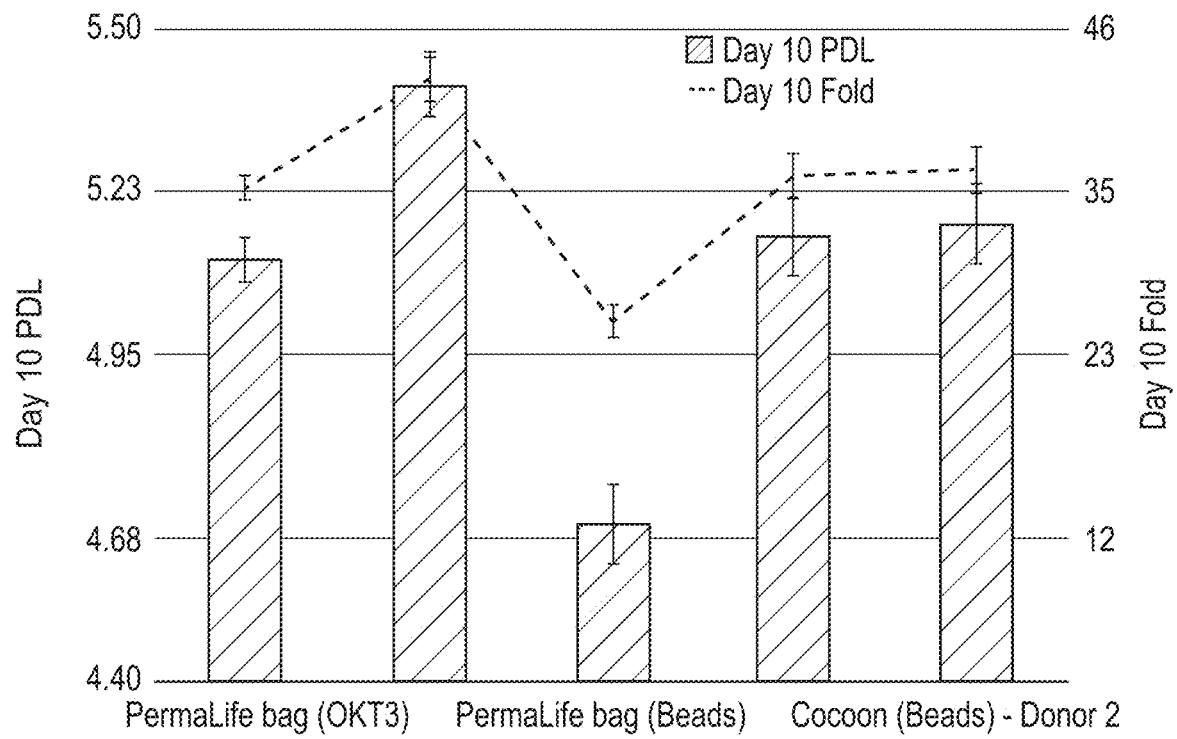

The Day 10 viable cell yield from the COCOON™ cultures activated with OKT3 and DYNABEAD(S)™ were $2.55 \times 10^9 \pm 0.1 \times 10^9$ and $2.15 \times 10^9 \pm 0.1 \times 10^9$ respectively. The viable cell yield from the PERMALIFE™ bag cultures activated with OKT3 and DYNABEAD(S)™ were $2.08 \times 10^9 \pm 0.1 \times 10^9$ and $1.53 \times 10^9 \pm 0.1 \times 10^9$ respectively (FIG. 13A). The viability in all conditions was greater than 95% (FIG. 13A). The population doubling level (PDL) was 5.2-5.4 in COCOON™ (36-43 fold) and 4.7-5.1 in the PERMALIFE™ bags (25-35 fold) (FIG. 13B).

Figure 13C:
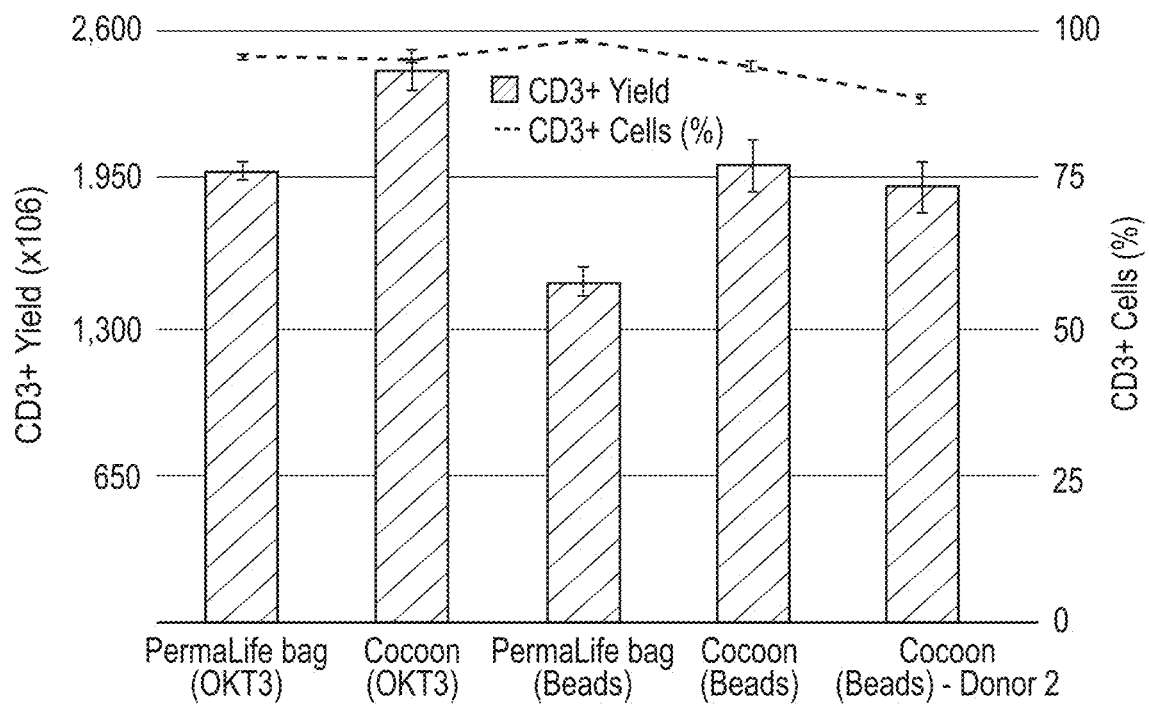
Figure 13D:
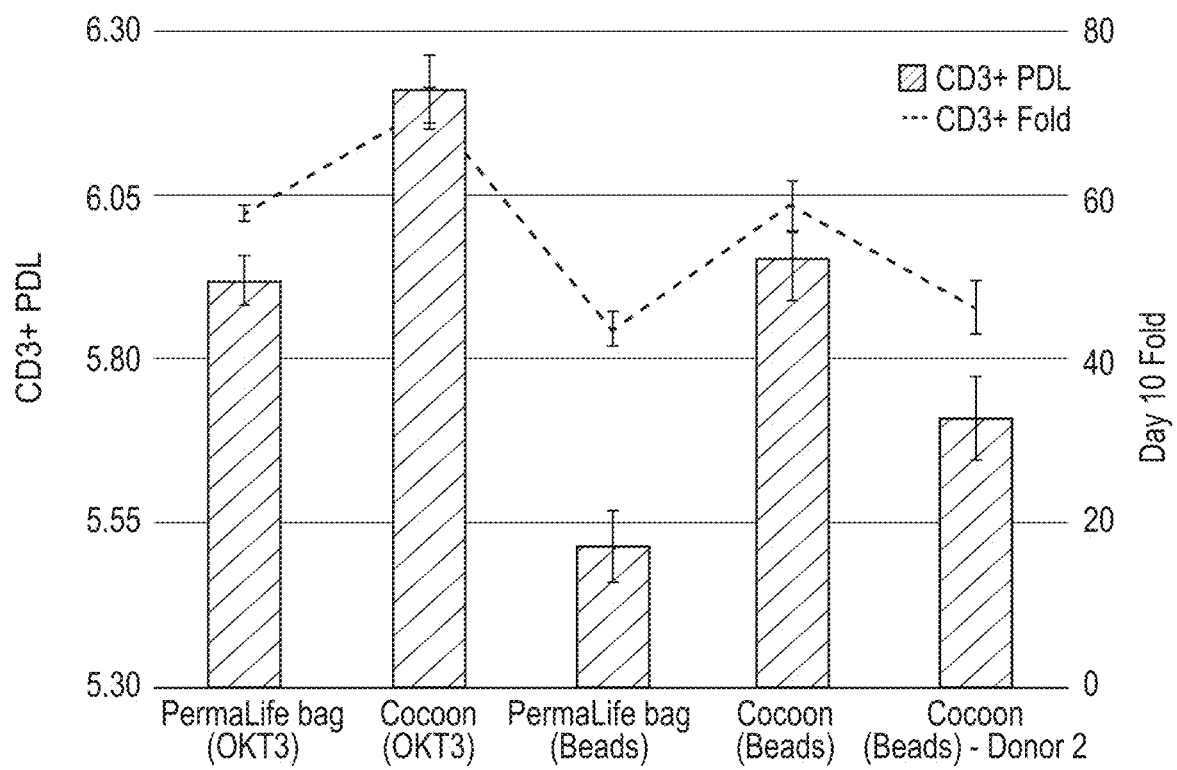

All conditions exhibited a high level of purity of T cells, with greater than 88% of the viable cells expressing CD3. The total viable T cells generated in 10 days was greater than 2 billion, with the exception of bead activated PBMCs grown in the PERMALIFE™ bags (FIG. 13C). Regardless of the activation method, the total T cell yield was greater in the COCOON™ conditions compared to the bags. The Day 10 COCOON™ Cassette T cell yield was $2.0$-$2.4 \times 10^9$. The PERMALIFE™ bags produced $1.5$-$2.0 \times 10^9$ T cells (FIG. 13C). Using the same donor cells, the PDL of CD3+ cells was 5.7 and 5.9 (51 and 60 fold) in COCOON™ activated using DYNABEAD(S)™ or OKT3 respectively (FIG. 13D). The PDL of the CD3+ cells was 5.2 and 5.6 (38 and 49 fold) in the PERMALIFE™ bags activated using DYNABEAD (S)™ and OKT3 respectively.

Figure 13E:
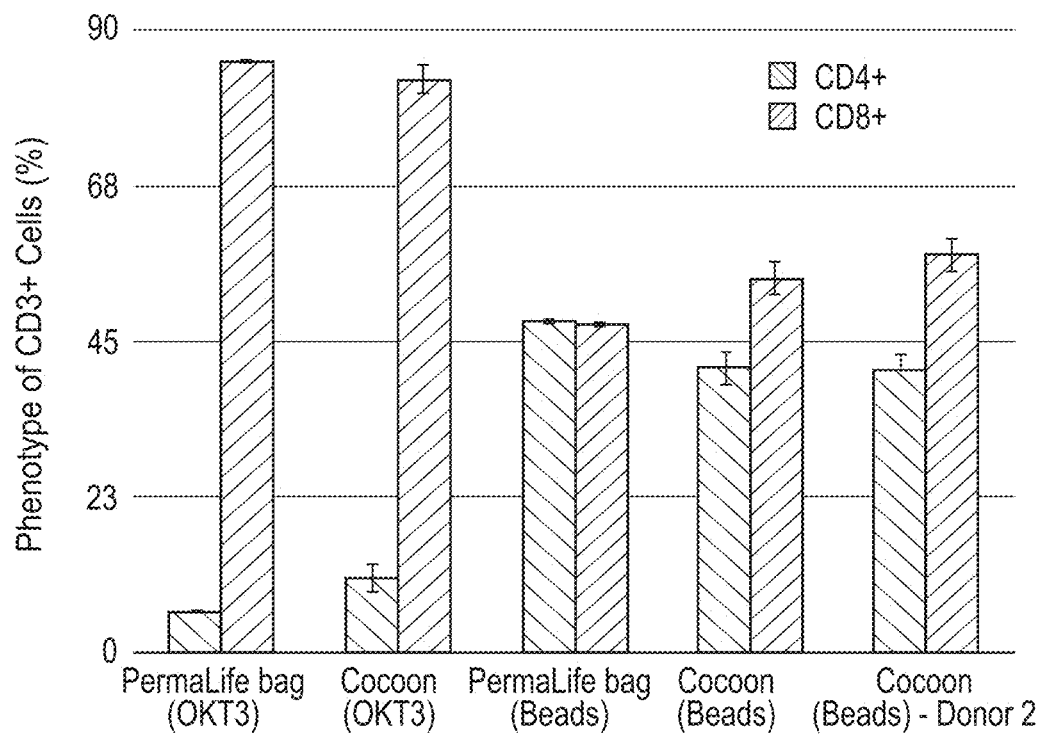
Figure 13F:
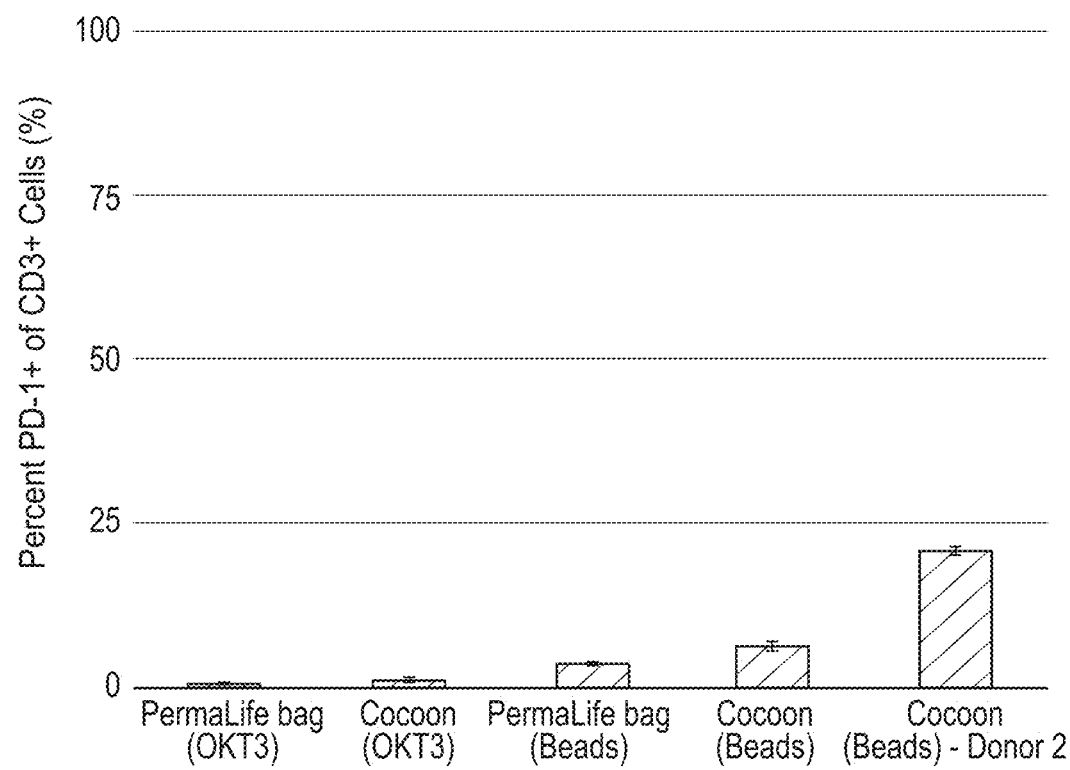
Figure 13H:
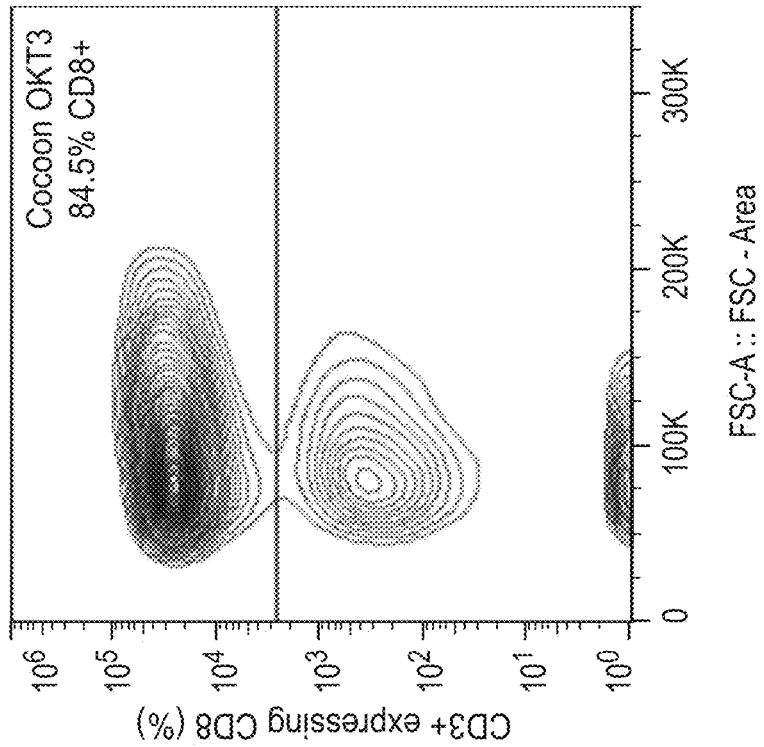
Figure 13G:
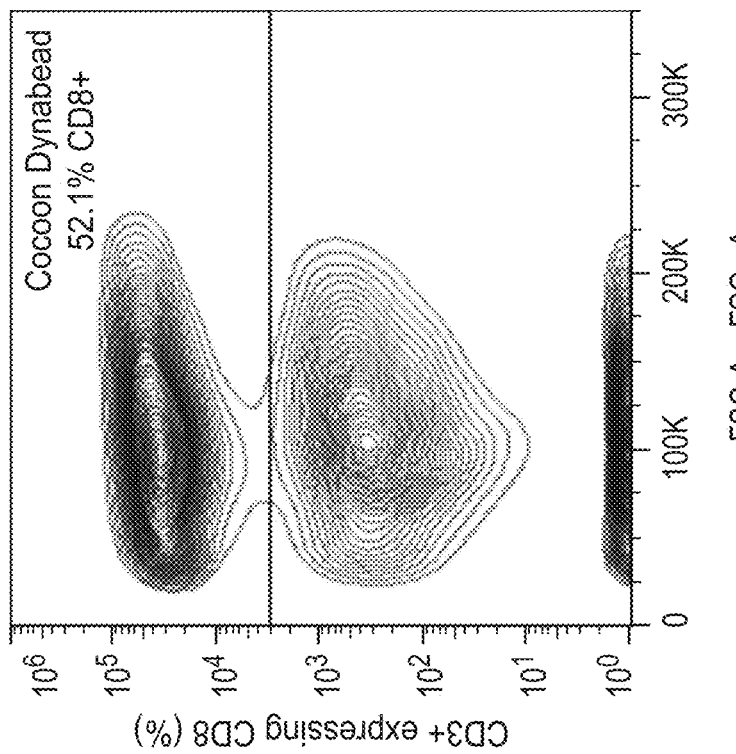

The percentage of CD3+ T cells expressing CD4 and CD8 glycoproteins, indicative of helper or cytotoxic T cells respectively, are shown in FIG. 13E. The most significant result related to the T cell subpopulations was the increased number of CD8 cells in the conditions activated with OKT3 compared to the DYNABEAD(S)™-activated cells. OKT3 activation resulted in 83-86% CD8+ and 6-11% CD4+ cells while DYNABEAD(S)™ activated conditions resulted in subpopulations of 48-56% CD8+ and 41-48% CD4+ cells. In all cultures with the same donor, the exhaustion associated marker, PD-1 was below 10%, indicating low levels of cell exhaustion (FIG. 13F). The second donor expressed PD-1 in 21% of the cells when cultured in COCOON™ with DYNABEAD(S)™. FIGS. 13G and 13H show representative contour plots highlighting the significant difference in CD8+ cells in the DYNABEAD(S)™-activated conditions compared to the OKT3-activated conditions.

Figure 14A:
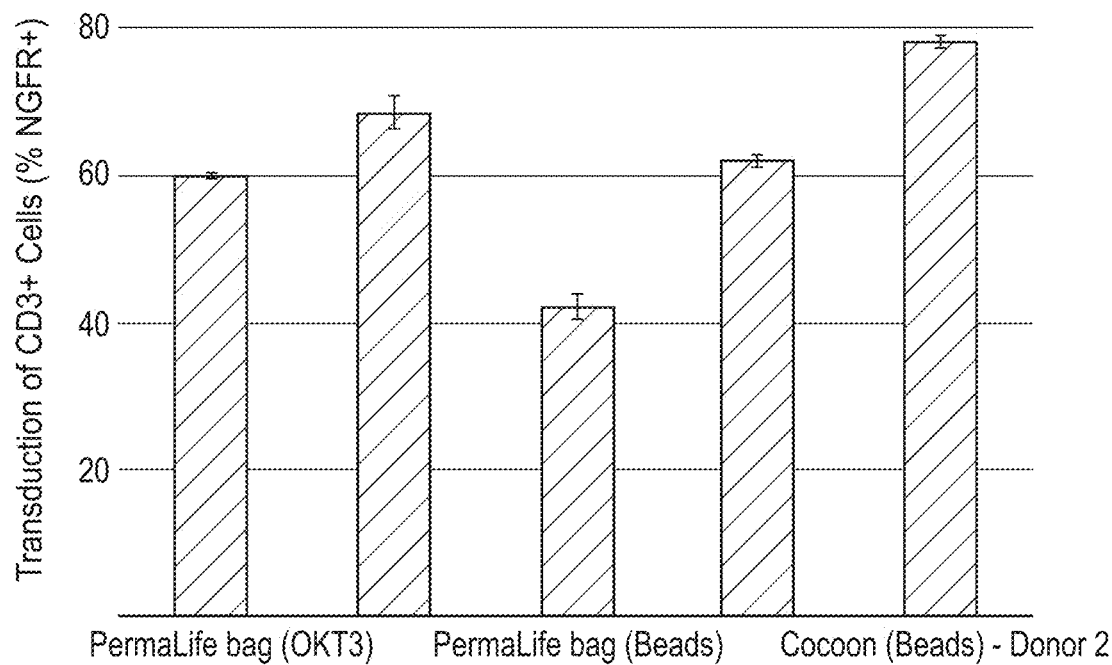
FIGS. 14A-14F show results of experiments described in Example 2, comparing the PERMALIFE™ bag and COCOON™ system.
Figure 14B:
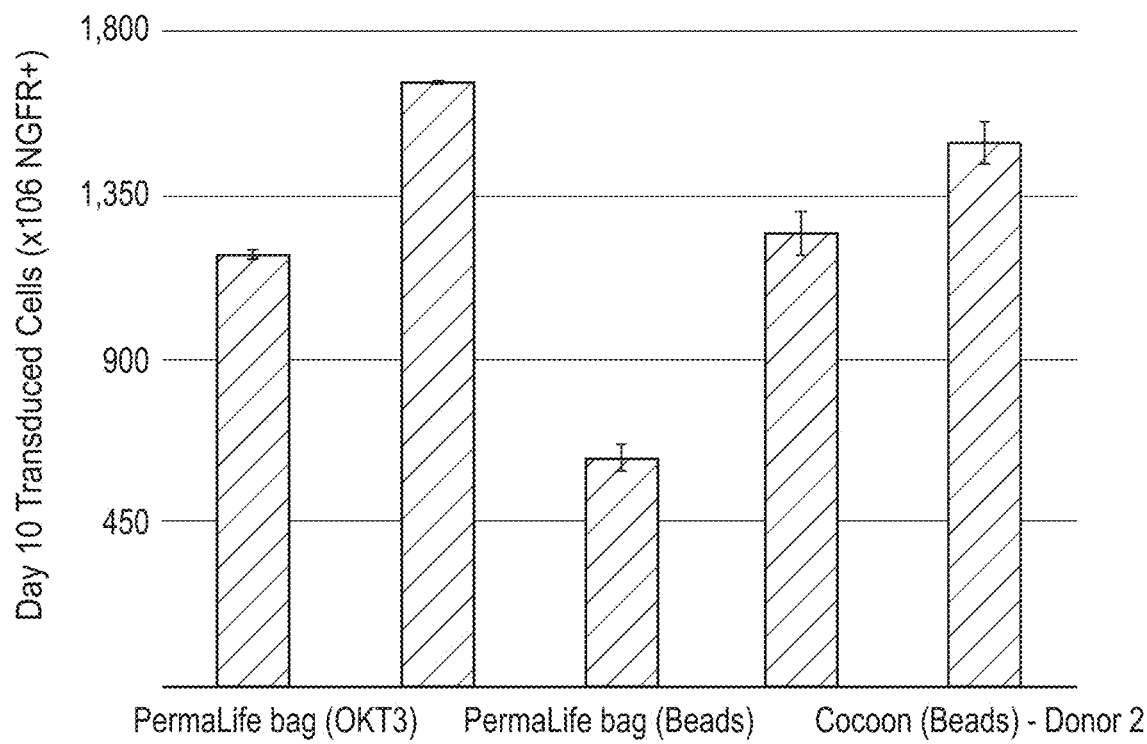
Figure 14C:
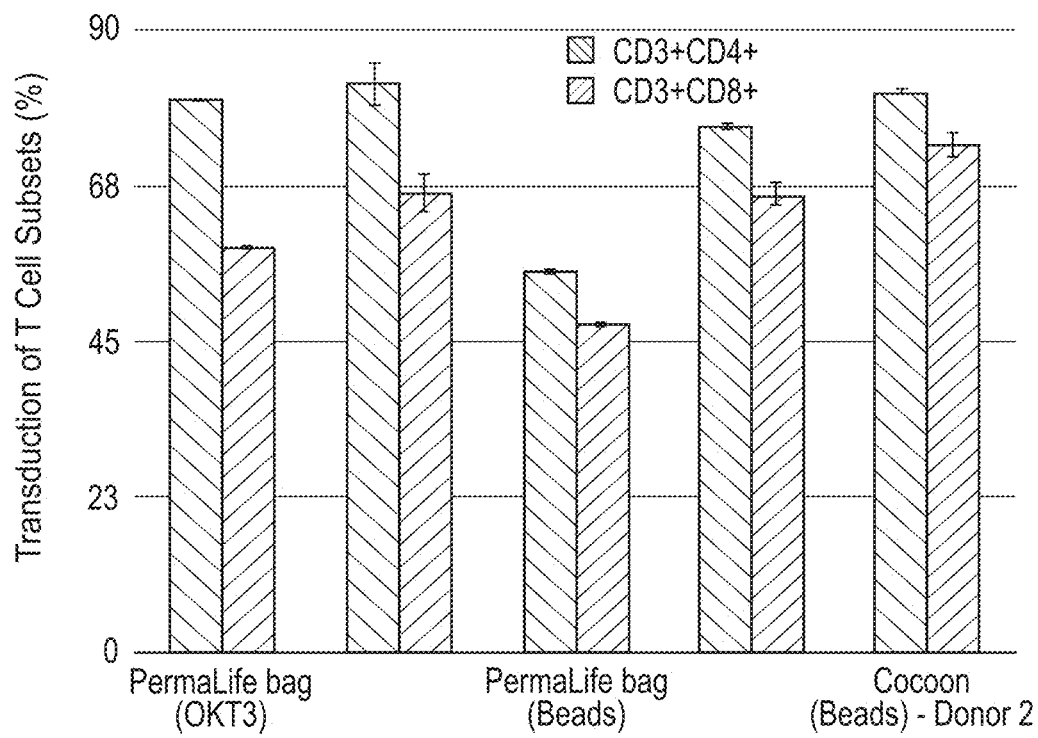
Figure 14D:
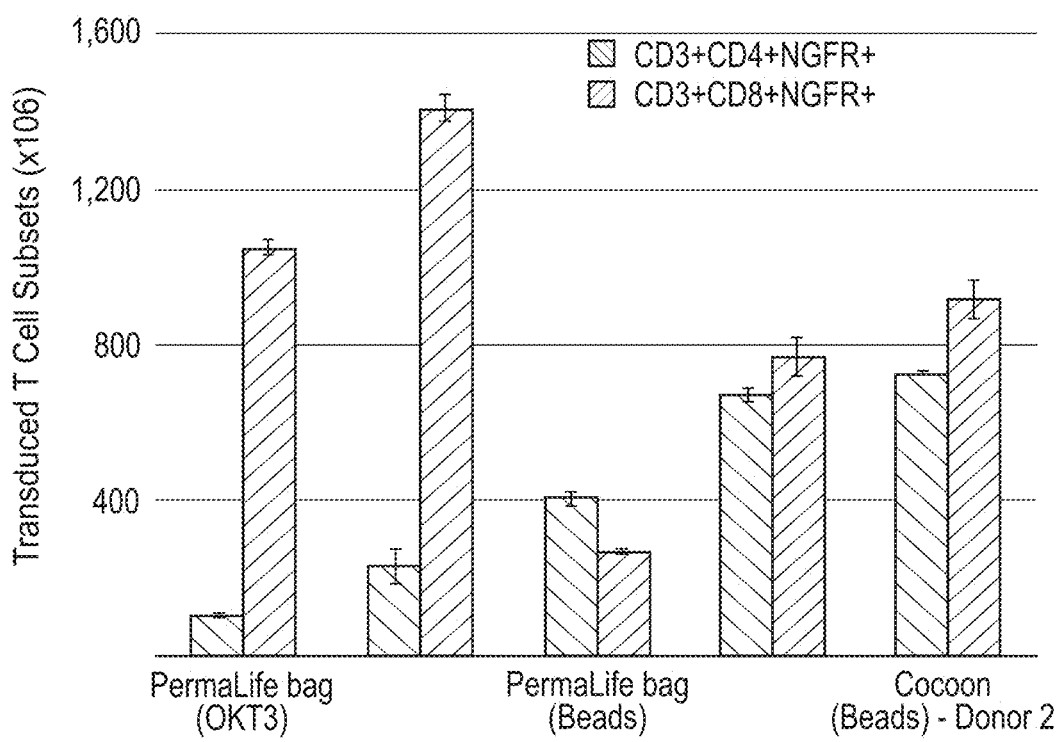
Figure 14F:
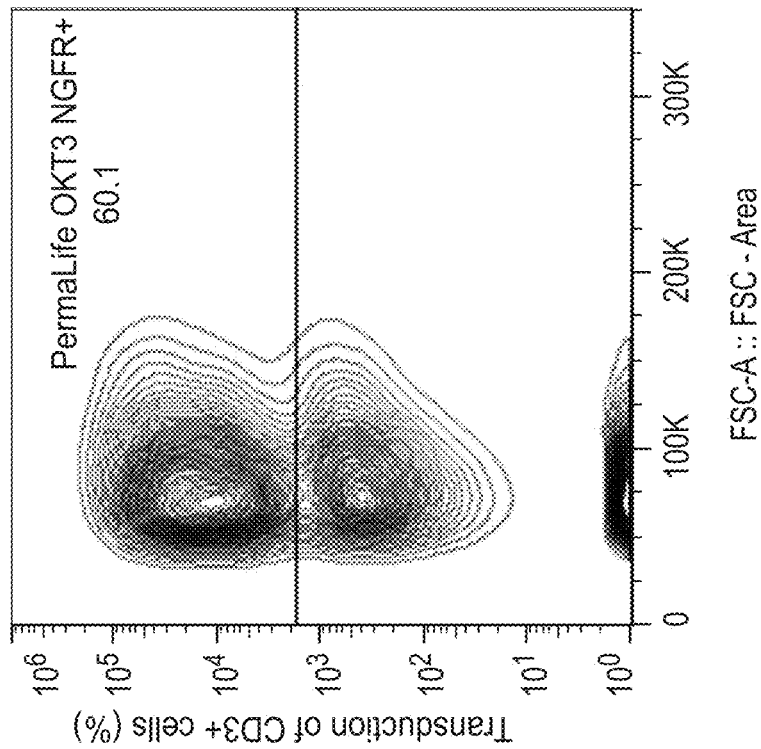
Figure 14E:
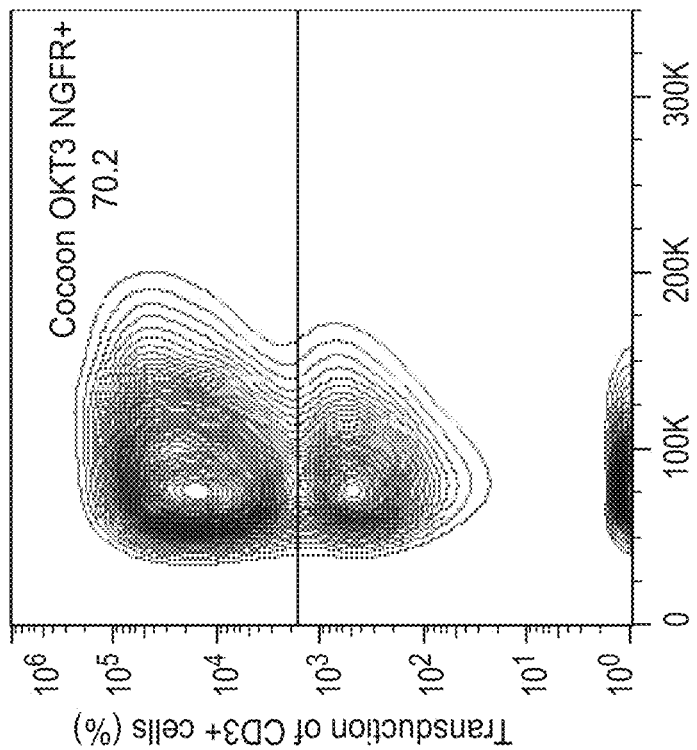
Figure 15A:
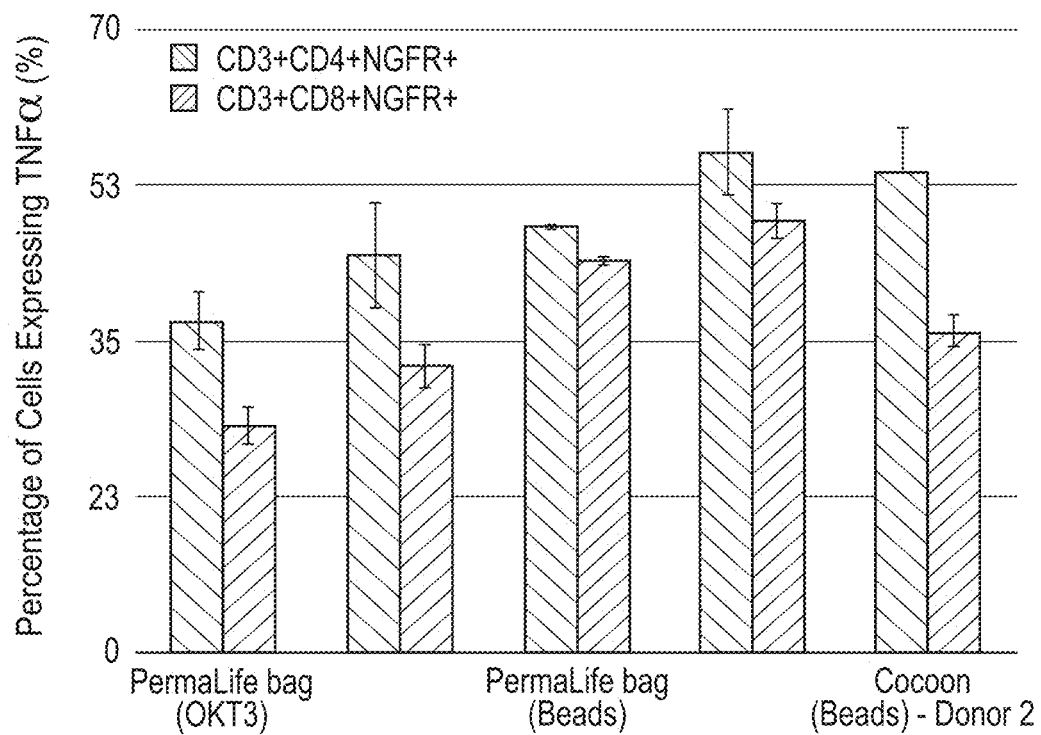
FIGS. 15A-15F show results of experiments described in Example 2, comparing the PERMALIFE™ bag and COCOON™ system.
Figure 15B:
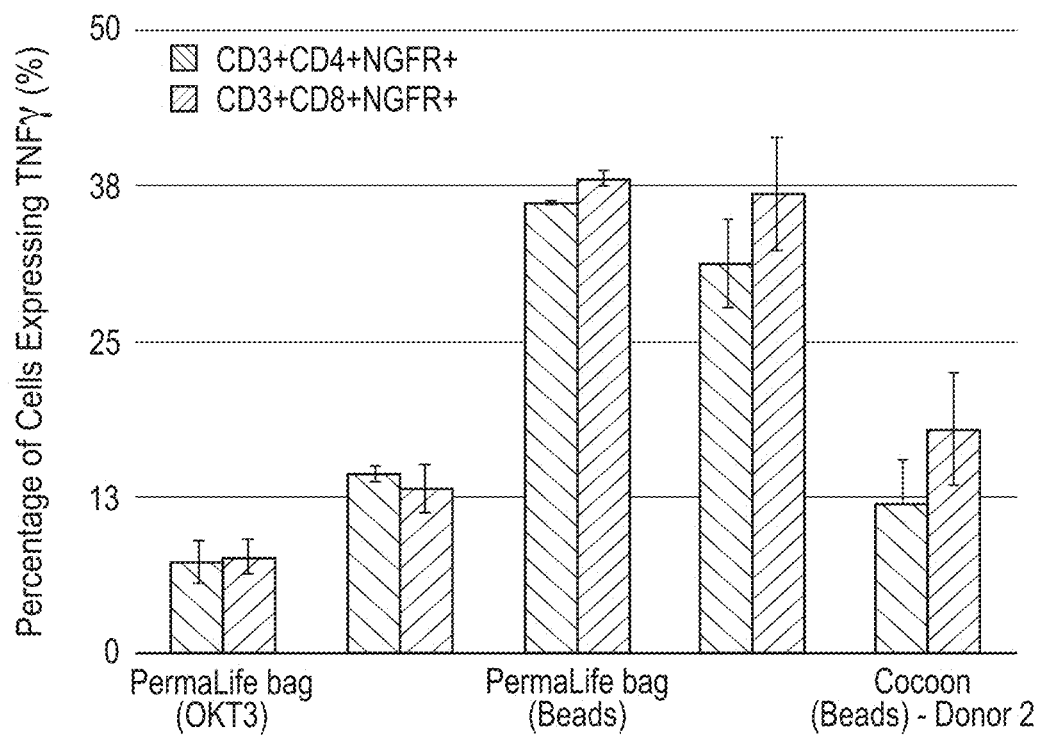
Figure 15C:
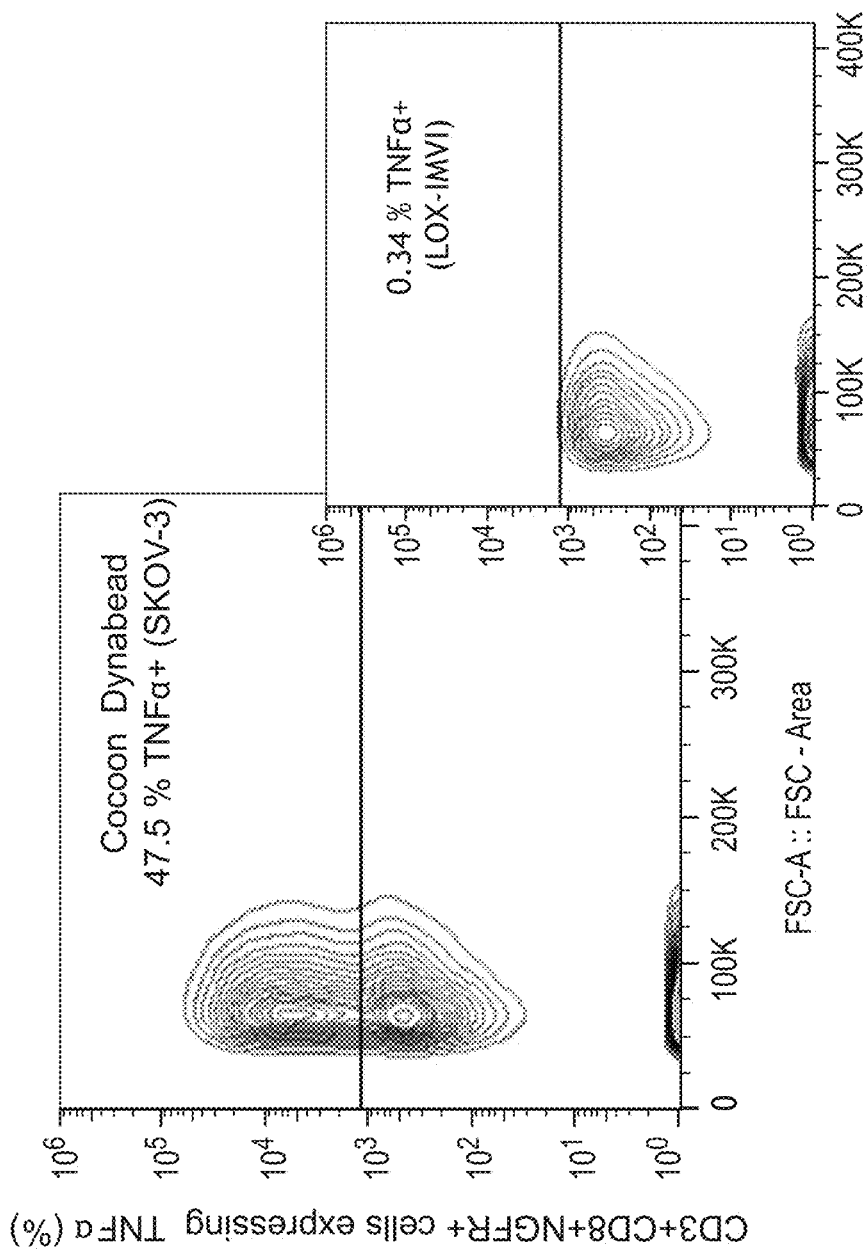
Figure 15D:
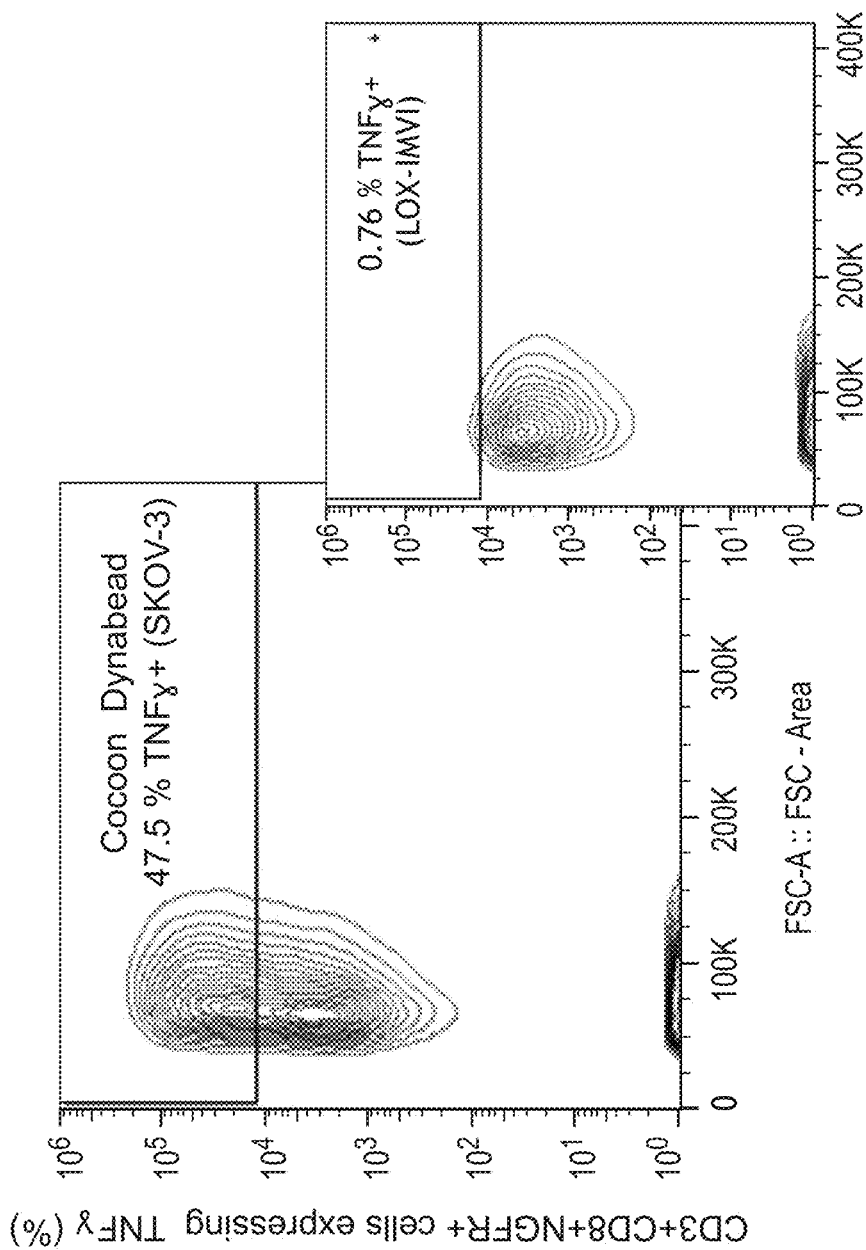
Figure 15E:
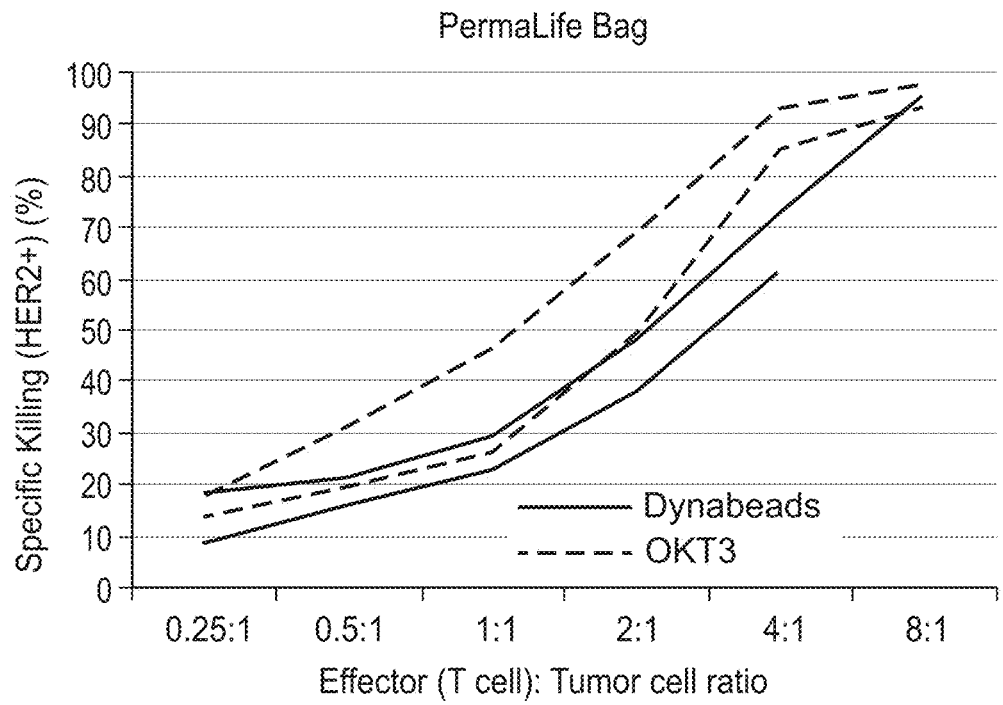
Figure 15F:
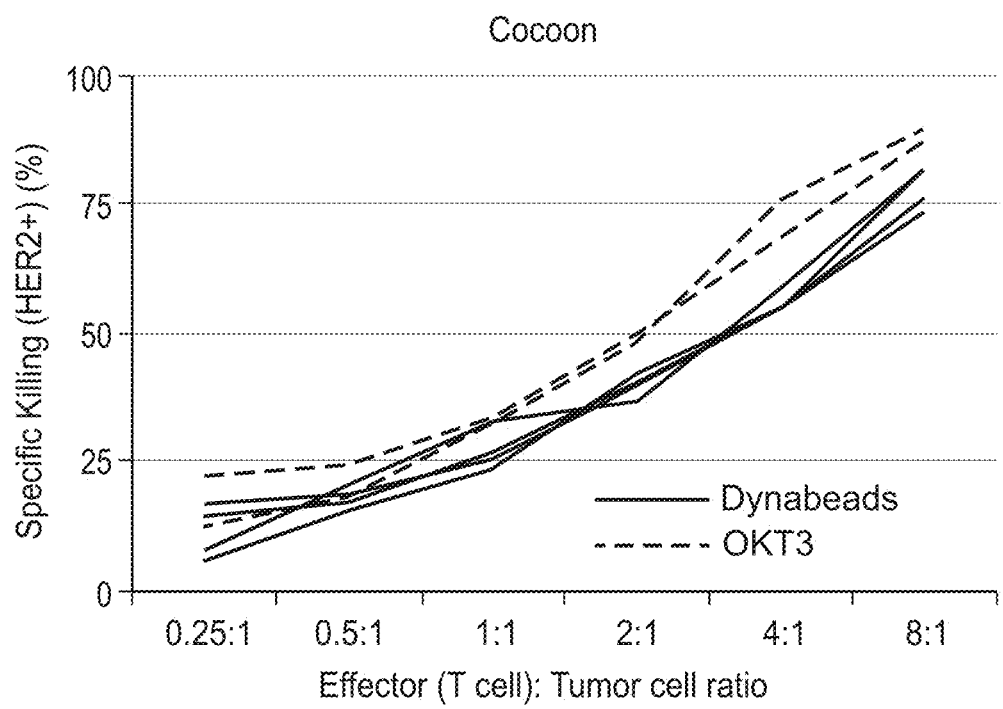

High transduction efficiency was determined by surrogate surface marker CD271 (NGFR) expression for T cell HER2 specificity with 62-78% of CD3+ cells in COCOON™ and 42-60% of CD3+ cells in PERMALIFE™ bags expressing NGFR (FIG. 14A). The transduction efficiency was greater in the COCOON™ compared to the bag cultures. With the high transduction and expansion, the total number of viable CAR T cells ranged from $1.26$-$1.66 \times 10^9$ in COCOON™ and $0.62$-$1.20 \times 10^9$ in PERMALIFE™ bags (FIG. 14B). The percentage and total number of CAR T cells in the CD4 and CD8 subpopulations are shown in FIGS. 14C and 14D respectively. The percentage of transduced CD4 cells was greater than the CD8 cells with 75.4-80.9% of CD4 cells and 64-73.2% of CD8 cells in COCOON™ expressing NGFR. In the PERMALIFE™ bags, 54.7-79.9% of the CD4 cells and 36.1-58.9% of the CD8 cells expressed NGFR. As the expansion of the CD8 cells was significantly greater than the CD4 cells, the total number of CD8+ transduced cells was significantly greater than the CD4+ transduced cells in all conditions except DYNABEAD(S)™-activated bag cultures (FIG. 14D). In the COCOON™ there were $0.25$-$0.64 \times 10^9$ transduced CD4 cells and $0.66$-$1.43 \times 10^9$ transduced CD8 cells. In the PERMALIFE™ bag conditions, there were $0.09$-$0.41 \times 10^9$ transduced CD4 cells and $0.25$-$1.06 \times 10^9$ transduced CD8 cells. Representative contour plots of the transduction efficiency in the COCOON™ conditions and PERMALIFE™ bag conditions are shown in FIGS. 14E and 14F respectively.

Functionality testing of the cells was performed using an intracellular cytokine release assay and an ALAMARBLUE™ killing assay (see Nociari 1998) (FIG. 15). In all cases, the cells demonstrated production of TNFα and IFNγ (FIGS. 15A and 15B), characteristic of type 1 T helper CD4+ cells and cytotoxic CD8+ cells (see, e.g., Romagnani 1991). Higher proportions of CD4+ cells secreted TNFα. The production of TNFα secreting cells was greater in the COCOON™ conditions compared to the bag cultures for the same donor cells. The DYNABEAD(S)™-activated conditions produced higher percentages of TNFα and IFNγ secreting transduced cells than the OKT3-activated conditions. The ALAMARBLUE™ killing assay demonstrated effective killing of ovarian carcinoma cell line SKOV-3 HER2+ tumor cells by the CART cells (FIGS. 15C and 15D). The trends of killing effectiveness followed the serial dilution of the effector T cells with strong response from both PERMALIFE™ and COCOON™ generated cells. HER2−tumor cells, LOX IMVI, were also exposed to the T cells to demonstrate HER2 specificity. No killing trends were identified in the HER2 negative cultures in response to the CAR T cells.

Discussion

Activation Method. Assessment of CAR T cell production included activation using soluble anti-CD3 (OKT3) as well as the bead-bound anti-CD3/anti-CD28 DYNABEAD(S)™. The cultures activated with OKT3 demonstrated improved growth of 19-36% over DYNABEAD(S)™-activated cultures (FIG. 13A). The method of activation also generated a significant difference in the final phenotype (FIG. 13E). The DYNABEAD(S)™-activated conditions had an average of 52.7% CD3+CD8+ cells compared to OKT3-activated conditions, which had 84.5% CD3+CD8+. This represents a CD8+ to CD4+ ratio of approximately 1.2:1 for DYNABEAD(S)™-activated conditions compared to 9.8:1 when activated with OKT3. The increased number of CD8+ cells were found regardless of whether the cells were cultured in bags or COCOON™ conditions.

The improved yield with OKT3 activation was an unexpected result. DYNABEAD(S)™ activate T cells by binding to the TCR/CD3 complex as well as the CD28 co-stimulatory receptor. Unlike DYNABEAD(S)™, which have an anti-CD28 antibody for co-stimulation, activation with soluble anti-CD3 relies on monocytes to present B7 receptors, CD80 and CD86, which are ligands to CD28 (see, e.g., Fleischer 1996). However, the B7 receptors can also bind to CTLA-4 and stimulate this inhibitory pathway, thus inhibiting T cell growth. The improved total cell yield based on activation method was found regardless of whether the cells were cultured in bags or COCOON™ conditions. Bead-bound anti-CD3/anti-CD28 antibodies may promote the expansion of helper T cells (CD4+ cells) while OKT3 may promote the expansion of cytotoxic T cells (CD8+ cells) (see, e.g., Fleischer 1996; Laux 2000; Li 2010; Zhu 2007).

The higher cell yield, and specifically, the CD8+ cell predominance may be attributed to the stimulation of additional receptors when activated using OKT3 and monocytes. It has previously been reported that 95% of CD4+ T cells express CD28 while only 50% of CD8 cells express CD28 (see Ledbetter 1990). Consequently, DYNABEAD(S)™ may only activate a maximum of 50% of the CD8+ cells. The cultures activated with OKT3 may benefit from other co-stimulatory ligands that are present on the monocytes and not on the beads.

For example, monocytes express CD58 (LFA-3) and CD40 receptors, which are ligands for CD2 and CD40L. Stimulation of these receptors is known to promote T cell growth. These accessory cells may also express CD137L, which interacts with CD137 and may stimulate CD8+ cell expansion. The interaction with these other receptors may representative a more physiologic antigen presentation compared to DYNABEAD(S)™ activation.

As OKT3 activation is dependent on other cells, the impact of donor variability may be more significant than activation with DYNABEAD(S)™. The starting cell population in this study was comprised of 12.0% CD14+ cells and 66.6% CD3+ cells on Day 0. A dose study could be performed to determine the impact of monocyte-sensitivity on the final yield and phenotype.

Automation. The COCOON™ generated a greater yield of viable CAR T cells compared to the manual conditions when activated with either OKT3 or DYNABEAD(S)™. When activated with DYNABEAD(S)™, the COCOON™ cultures yielded 40% more growth than bag cultures. With OKT3 cultures, the COCOON™ yielded 23% more cells than bag cultures. The COCOON™ conditions also demonstrated greater transduction efficiency and consequently a greater total yield of CAR T cells (FIG. 14). With DYNABEAD(S)™-activated conditions, the total CAR T cell yield in the COCOON™ was more than double that of the bags. With OKT3-activated conditions, the yield of CAR T cells was approximately 40% more in COCOON™ than the bags.

The improved yield in COCOON™ over the PERMALIFE™ bags may be increased activation. This may be due to the distribution across culture area. The COCOON™ utilizes a solid non-yielding chamber whereas the bags are flexible. Following cell settling, it was observed that the curvature of the bag caused an uneven distribution of cells. This may have caused an uneven distribution of activation agent and/or cells. Another possible cause may be related to the amount of agitation during the activation phase. As the cells were transduced the day after activation, activation may still have been in progress or the activation agent may not have been internalized by the cells. During the transduction step, the bag cultures are moved from the incubator to the biosafety cabinet to deliver the cells using sterile technique. The movement of the bags facilitates virus distribution in the bags; however, the cells are also disturbed during the transfer of the bags to and from the incubator. As stable contact may be important for cell activation, this movement may have negatively impacted the cells. The cells in the COCOON™ cultures are not disturbed between the activation or transduction step. In the COCOON™, the media used for activation is removed from the culture prior to transduction. A small volume of media is left in the chamber that enables the cells to remain at the bottom of the chamber, undisturbed during the volume transfers. The media removed from the chamber is used to dilute and mix the virus and is then transferred back to the cell population. During this process, the cells remain undisturbed.

Efficient activation may correlate to more efficient transduction. That is, if the cells are activated and are actively dividing, the lentivirus could integrate more effectively. To assess this, samples could be taken prior to transduction to determine the activation efficiency. The improved transduction efficiency may also be related to the homogeneous distribution of the virus to the cells. In COCOON™ cultures, the virus is mixed with the media and uniformly distributed to the cells. Using a flat, non-flexible, vessel helps to improve homogeneous distribution and consequently homogeneously exposure of the virus amongst the cell population.

Another reason for the improved performance may be related to gas exchange. Increased oxygen levels may support increased proliferation. High oxygen levels were maintained in the automated platform by using recirculation of the culture supernatant through a silicone gas exchange line. Gas exchange is achieved in the bag conditions by diffusion through the bag material, fluorinated ethylene propylene (FEP). The permeability coefficient of silicone is significantly greater than the permeability of the FEP (see, e.g., Avgoustiniatos 2008). The COCOON™ protocol was created to ensure sufficient oxygen concentration. This was confirmed by biosensor data generated throughout the culture period.

The gas exchange via the silicone tubing also supports pH level. That is, at the beginning of the culture, the media maintains the target pH by gas exchange with a $CO_2$ enriched environment. As the cell number in the culture increases, the cells produce lactic acid and $CO_2$, to remove the need for a $CO_2$ environment. The $CO_2$ in the COCOON™ environment decreased over the culture duration to help to maintain pH. The PERMALIFE™ bags followed a conventional protocol of being stored in a 5% $CO_2$ environment throughout the culture process.

An additional advantage of the continuous recirculation, without disturbing the cells, is a more homogeneous distribution of positive and negative factors. This includes nutrients, waste, released cytokines and dissolved gases. Continuous recirculation may help to reduce localized effects and improve the media efficiency by evenly distributing factors.

Automation Translation. In this Example, a closed and automated production system, COCOON™, was used to generate CAR T cells activated by either bead-bound antibodies or soluble OKT3. The results demonstrate that a clinically-relevant yield can be generated from COCOON™ with a high transduction efficiency using a low concentration of virus. Furthermore, the phenotype of the cells can be driven by the activation method.

The results were primarily generated from a single donor to compare the impact of activation method. The variability between conditions was very low. When the test was repeated with a different donor, the results were similar between donors when using the same method of activation. This study demonstrates an efficient method of effectively automating the production of CAR T cells in a clinically-relevant, scalable, and easy to use method.

Example 3— Transduction Via Electroporation with a Cell Engineering System

BACKGROUND

The Octane COCOON™ system is an automated, closed, end-to-end bioreactor system for the manufacture of cell therapy products. Octane's Automated Cell & Tissue Engineering System (ACTES) is comprised of three main components: the base instrument, software, and customizable disposable cassette. The COCOON™ system is capable of automated isolation, expansion, concentration, and buffer exchange for both upstream and downstream cell culture processes.

An electroporation unit enables transfection of cells traditionally known to have low transfection efficiency via electroporation and other non-viral methods, including primary cells, stem cells, neurons, and resting or non-proliferating cells. The system includes an electroporation unit, electroporation solutions, electroporation Cartridges and optimized electroporation protocols. The electroporation unit is comprised of a Core Unit and 1-3 additional functional add-on units addressing different needs. For example, the electroporation unit can be used to transfect varying cell numbers in 204-1004 and $1\times10^7$ to $1\times10^9$ in 1 mL-20 mL volume.

Described herein is an automated, completely closed, sterile and robust Transfection and cell expansion procedure using an electroporation Unit and Octane COCOON™ systems. In the proof-of-concept (PoC) evaluations, the respective electroporation Software and Octane Cocoon™ ACTES software will operate independently of one another. In other embodiments, the software is fully integrated between the systems.

Methods

Evaluation of Peripheral Blood Monocyte Cell (PBMC) transfection and expansion using the electroporation unit and Cocoon™ systems was divided into three main focus areas:

Cell concentration in the Cocoon™ cassette, cell transfer between the Octane Cocoon™ and the electroporation Unit, expansion of transfected cells transferred between the Cocoon™ and electroporation Unit and cell concentration in the Cocoon™ cassette.

The Cocoon™ ACTES cassette recirculates about 450 mL of culture media in its culture chamber. The cell proliferation chamber typically holds a constant volume of up to 180 mL of media within its 260 cm² area. Additional media volume beyond the 180 mL capacity of the 260 cm² proliferation chamber is provided from various satellite reservoirs and chambers of the Cocoon™ cassette. The additional media from these satellite reservoirs can be recirculated within the culture portion of the disposable Cocoon™ to provide fresh nutrients and remove waste products from cells in the 260 cm² proliferation chamber.

An exemplary volume that the electroporation Unit can transfect is 20 mL. The 20 mL volume should suitably be comprised of at least 90% of the appropriate electroporation Solution. Thus, for PoC studies, the original culture volume was reduced to 10 mL, then diluted in an additional 90 mL of supplemented P3 Primary Cell electroporation Solution, and concentrated to a final volume of 10 mL-18 mL.

The Proof of Concept studies described utilized the following:

A 20 gauge, 0.024" I.D./0.036" O.D., flow restrictor from Nordson EFD, which was added to the end of the permeate line.

$1\times10^8$ PBMCs were stimulated with $1\times10^8$ CD3+:CD28+ DYNABEAD(S)™ (Invitrogen) and expanded in Complete T-cell Media comprised of X-VIVO™ 15 media (Lonza) supplemented with 5% Human Serum A/B (Sigma) and 10 ng/mL IL-2 (Peprotech) using multiple GREX 100 (Wilson Wolf) culture vessels for up to 10 days. Test concentrations of cells were transferred to 250 mL conical vials and allowed to settle in 37° C. incubators with 5% $CO_2$ in air humidified for 2-4 hours. The supernatant of the settled cell suspension was reduced to 10 mL and excess supernatant discarded. 90 mL of supplemented P3 Primary Cell electroporation Solution (Lonza) was added to the concentrated cell suspension for a final volume of 100 mL. The 100 mL cell suspension was then concentrated to a volume of 10 mL. A control sample of cells were incubated at 37° C.

Counts were performed in duplicate using the NUCLEO-COUNTER® NC-200 (Chemometec) on the pre-diluted cell culture, the diluted culture and the final concentrated cell suspension. Volumes were measured using a serological pipette and KrosFlo scales. Residual testing samples were obtained from the initial culture pre-dilution, supernatant, and final concentrated cell suspension. A Human Serum ELISA Kit (Bethyl Laboratories) was used to determine the percentage of serum remaining post dilution and concentration. FACS analysis was performed on control cells and concentrated cell suspensions for CD4+ and CD8+ expression.

Successful demonstration of volume reduction for Cocoon™ transfection protocols was defined as follows: ≥85% recovery of cells, ≤10%, decrease in cell viability and 10%, residual human serum of the initial concentration.

Cell Transfer between the Octane Cocoon™ and the electroporation Unit

The transfer of cells between the Cocoon™ and electroporation Unit requires several disposable consumables: the Cocoon™ cassette, the electroporation Cartridge, two modified electroporation Reservoirs, and two Connection Tubing Sets (See FIG. 17).

The modified electroporation Reservoirs include inlet and outlet weldable tubing with a luer lock connection endings, a cell inlet port within the Reservoir housing connected to the external inlet Reservoir tubing for sterile cell transfer into the Reservoir, a luer lock substrate addition port on the inlet tubing of the LV Reservoir, and a vent filter on the cap for air escape during volume transfer. The Cocoon™ cassette is designed with a port capable of automating transfer of fluids and cell suspensions outside of the Cocoon™ in a controlled manner, without compromising the sterility or cellular health of the culture.

Successful demonstration of aseptic transfer of cells between the Cocoon™ and electroporation Unit demonstrated: supernatant of transferred, transfected cells passed sterility testing, no mycoplasma detected in pre- and post transfected culture samples ≥90% recovery of pre-transfected cell/volume in the Cocoon™ cassette post transfection and delivery to the Cocoon™ cassette proliferation chamber, 5% change in viability of non-transfected cells between Cocoon™ and electroporation Unit cell transfer movements and ≤20% change in CD3+, CD4+, and CD8+ cells when comparing cells transfected with and without automated transfers between the Cocoon™ and electroporation unit.

The Cocoon™ ACTES Cassette has two sampling ports with BD Q-Syte female luer lock endings, as well as inlet and outlet ports with cannulas that allow for automated transfer of cell suspensions out of the Cocoon™ cassette and through Connection Tubing Sets aseptically connected to these locations. During PoC studies, connections between the Cocoon™ cassette, electroporation Reservoirs, electroporation Cartridge, and Connection Tubing Sets were aseptically connected to produce a sterile loop between the Cocoon™ and electroporation systems as follows.

Connection Tubing Sets with ICU Medical Spiros® male luer lock ending connectors were connected to the two BD Q-Syte female luer lock sampling ports of the Cocoon™. To make a sterile pathway from the Cocoon™ cassette to the electroporation Reservoir, the other Spiros® male luer lock connection (ICU Medical) of the Connection Tubing Set was connected to the female luer lock inlet tubing of the electroporation Reservoir. To connect the modified electroporation Reservoir to the electroporation Cartridge, the female luer lock ending of the modified electroporation Reservoir drain line was attached to the Spiros® male luer lock connection (ICU Medical) of the electroporation Cartridge inlet. For collection of the transfected cells, the Spiros® male luer lock output connection of the electroporation Cartridge was connected to the female luer lock connector inlet of a second electroporation Reservoir. The female luer lock ending of the second electroporation Reservoir drain line was connected to the Spiros® male luer lock connector of the Connection Tubing Set on the second automated sampling port of the Cocoon™ cassette.

In embodiments, the Cocoon™ pump transfers the transfected cells to the Cocoon™ proliferation chamber, the second electroporation Reservoir or other collection vessel capable of aseptic transfer of cells is utilized to collect the newly transfected cells before delivery to the proliferation chamber of the Cocoon™ cassette. Sterile welding techniques can be used in place of aseptic luer lock connections between the inlet and outlet PVC tubing lines of the modified electroporation Reservoirs and Connection Tubing Sets with PVC tubing is feasible.

The cell engineering systems (COCOON™) described herein also allows for sterile, closed connections between the Cocoon™ cassette and an electroporation Unit, via tubing guided from the internal Cocoon™ environment through a hollow shaft of the Cocoon™ instrument. This hollow shaft, referred to as the "Trumpet Arm", provides access to the internal environment of the Cocoon™ culture chamber from the external environment without loss of control over key process parameters. Cell movement between the Cocoon™ and electroporation Unit used the peristaltic pumps and software of the two separate control systems, but can also utilize software of a combined system to control the separate pumping systems.

Prior to transfection, cells/fluid were either manually transferred to a sterile electroporation Reservoir to mimic pre-expansion (Day 0) transfection procedures or transferred from the Cocoon™ cassette proliferation chamber to mimic post-expansion transfection procedures to the sterile electroporation Reservoir using the Cocoon™ pump, software, and Connection Tubing Sets (previously described). The Cocoon™ pump and software then automated the transfer of cells/fluid from the Cocoon™ cassette to the inlet of the electroporation Reservoir. The electroporation system executed pre-programmed pump movements of up to 20 mL from the electroporation Reservoir, through the electroporation Cartridge, and to the second electroporation Reservoir. The Cocoon™ pump then transferred the collected transfected cells/buffer from the second electroporation Reservoir to the proliferation chamber of the Cocoon™ cassette.

A second electroporation Reservoir was incorporated to collect the transfected cells and hold them until ready to be transferred by the Cocoon™ pump to the Cocoon™ proliferation chamber. To use only the electroporation Unit pump to move the transfected cells from the electroporation Unit to the Cocoon™ proliferation chamber, a "Connection Tubing Set Clearing" program can be utilized. In addition, the Connection Tubing Sets should be consistent in length.

Using the Cocoon™ cassette, Connection Tubing Sets, and modified electroporation Reservoir connections previously described (FIG. 17), 11 mL of Phosphate Buffer Solution (Lonza) was transferred from the Cocoon™ cassette to the modified electroporation Reservoir using the Cocoon™ pump. An electroporation program was used to perform a mock transfection of the PBS solution and move the 11 mL volume to the second modified electroporation Reservoir. The Cocoon™ pump and software was then used to transfer the 11 mL volume from the second modified electroporation Reservoir to the output bag of the Cocoon™ cassette. Volume transferred to the satellite bag from the Cocoon™ reservoir was estimated at 11 mL per run. Actual volume was measured using serological pipette after transfer to the first modified electroporation Reservoir, second modified electroporation Reservoir, and Cocoon™ output bag. Passing criteria was established at ≥90%, fluid recovery from the first modified electroporation Reservoir to the Cocoon™ output bag.

Cell Suspension Testing $1\times10^8$ and $5\times10^8$ total viable PBMCs will be expanded in 450 mL of Complete T-cell Media, comprised of X-VIVO™ 15 media (Lonza) supplemented with 5% Human Serum A/B (Sigma) and 10 ng/mL IL-2 (Peprotech), in the sterile Cocoon™ ACTES cassettes. On day 3, 440 mL of the culture supernatant will be removed and held for sterility and mycoplasma testing. The cells will be diluted in 90 mL of supplemented P3 electroporation Solution (Lonza). The cells will then be concentrated in the Cocoon™ cassette to approximately 10 mL of cell suspension and transferred to the Cocoon™ satellite bag. An option to wash the proliferation chamber with an additional 10 mL of supplemented P3 electroporation Solution and added to the cell suspension in the Cocoon™ satellite bag will be evaluated. A sample will be removed from the concentrated cells in the satellite bag for duplicate cell counts using the NUCLEOCOUNTER® NC-200 (Chemometec), mycoplasma, and sterility retains. The cells will then be transferred to a modified electroporation Reservoir via the Cocoon™ pump and Connection Tubing Sets, as previously described. The electroporation Unit pump and EO-210 program will be used to transfect the T-cells with pmax GFP Vector (Lonza) and transfer the transfected cells to a second modified electroporation Reservoir. The Cocoon™ pump will then transfer the cells from the modified electroporation Reservoir to the proliferation chamber of the Cocoon™ ACTES cassette. A sample of the cells will be removed from the ACTES cassette proliferation chamber for duplicate cell count, mycoplasma, and sterility testing. This procedure will be repeated with a control culture in which cells will not be transfected, but instead passed through the electroporation Unit using the mock electroporation Program CA-100. This procedure will be evaluated using three different donors; both freshly isolated and from cryopreserved PBMC lots.

Change in cell viability will be measured in the non-transfected cell cultures. Cell recovery, sterility, and mycoplasma load will be assessed in all cultures. Flow cytometry will be used to evaluate GFP, CD3+, CD4+, CD8+, and additional marker expression.

Aseptic Transfer of Cell Suspensions between Cocoon™ and electroporation Unit provide sterile and mycoplasma-free supernatant pre- and post-movements, 90% recovery of pre-transfected cells in the Cocoon™ cassette post transfection and delivery to the Cocoon™ cassette proliferation chamber, ≤5% change in viability of non-transfected cells, ≤20% change in CD3+, CD4+, and CD8+ cell ratios post transfection.

Expansion of Transfected Cells Transferred Between the Cocoon™ and Electroporation Unit $1\times10^8$ and $5\times10^8$ total viable PBMCs will be expanded and concentrated in the Cocoon™ cassette, transfected via sterile connection the electroporation LV Unit, and sterilely transferred to the Cocoon™ as previous described in the methods section for "Cell Transfer between the Octane Cocoon™ and the electroporation LV Unit, Cell Suspension Testing". Transfected cells will be cultured for up to 15 days in the Cocoon™ cassette proliferation chamber using the most relevant and optimized automated Cocoon™ protocol. A control will be expanded in a T-225 flask (Corning) or GREX 100 (Wilson Wolf) culture vessel for 3 day. On Day 3, the control culture will be aseptically and manually concentrated, transfected via the electroporation LV Unit EO-210 program, and transferred back to the original vessel for continued expansion of up to 15 days. This procedure will be evaluated using three different donors, from either freshly isolated or cryopreserved PBMC lots.

Expansion of transfected cells transferred between the Cocoon™ and electroporation Unit provided ±10% variability in transfection efficiency when compared to the control culture 24 hours post transfection and on day of harvest, a final cell concentration ≥80% of the control culture, ±5% variability in Final Cell Viability when compared to the control culture, ±10% variability when compared to the control culture in GFP+, CD3+, CD4+, and CD8+ expression, as determined via FACS, supernatant of transferred transfected cells passed sterility testing and no mycoplasma detected in pre- and post transfected culture samples.

Results

Cell Concentration in the Cocoon™ Cassette

The cells from two donors were concentrated by settling to a 10 mL volume with $4.4\times10^8$ and $4.2\times10^8$ total viable cells. These two cell suspensions were then diluted with 90 mL of supplemented electroporation Solution (NFS) and concentrated. Cell recovery post concentration was 92% and 87%. Cell viability prior to transfection were 92% and 74% and decreased by less than 5%. In both runs, 6% and 8% of the initial culture supernatant was detected in the final concentrated cell suspension.

TABLE 3

Percent of detectable human serum A/B in the original culture supernatant, post diluted and concentrated permeate, and final cell suspension supernatant.

| Sample ID | Human Serum Concentration of Initial Culture (ng/mL) | Human Serum Concentration Pre (ng/mL) | Human Serum Concentration Pre (% of initial) | Human Serum Concentration Post (ng/mL) | Human Serum Concentration Post (% of initial) |
|---|---|---|---|---|---|
| Donor 1 | 4.98E+06 | 2.19E+05 | 4% | 2.84E+05 | 6.00% |
| Donor 2 | 4.28E+06 | 3.48E+05 | 9% | 3.30E+05 | 8.20% |

There was no difference in CD4+:CD8+ profiles post concentration compared to the control culture that was not concentrated.

Results demonstrated recovery of fluids from the Cocoon™ satellite bag to the Cocoon™ output bag. Expansion of transfected cells were transferred between the Cocoon™ and electroporation Unit. Successful electroporation is carried out in the electroporation Unit, resulting in the transduced cells.

Automated, completely closed transfection using a closed loop between the electroporation Unit and Cocoon™ systems, is provided herein. Methods can be used for concentration of cells in the Cocoon™ system.

Example 4— Hematopoietic Stem Cell Expansion

CD34+ focused on the expansion of cord blood. The specific application of this was the expansion of CD34+ from cord blood samples that contain a low CD34+ number in order for single well-matched cords to be used for adult treatments. Therefore, the starting cell number and concentration was very low compared to some other protocols. It is expected that with larger starting numbers and concentration, the cell expansion would be lower.

CD34+ cells selected and expanded

Total nucleated cell (TNC) tracked over time

Starting cell concentrations were lower than many other protocols (0.1 M cells/ml)

Figure 19:
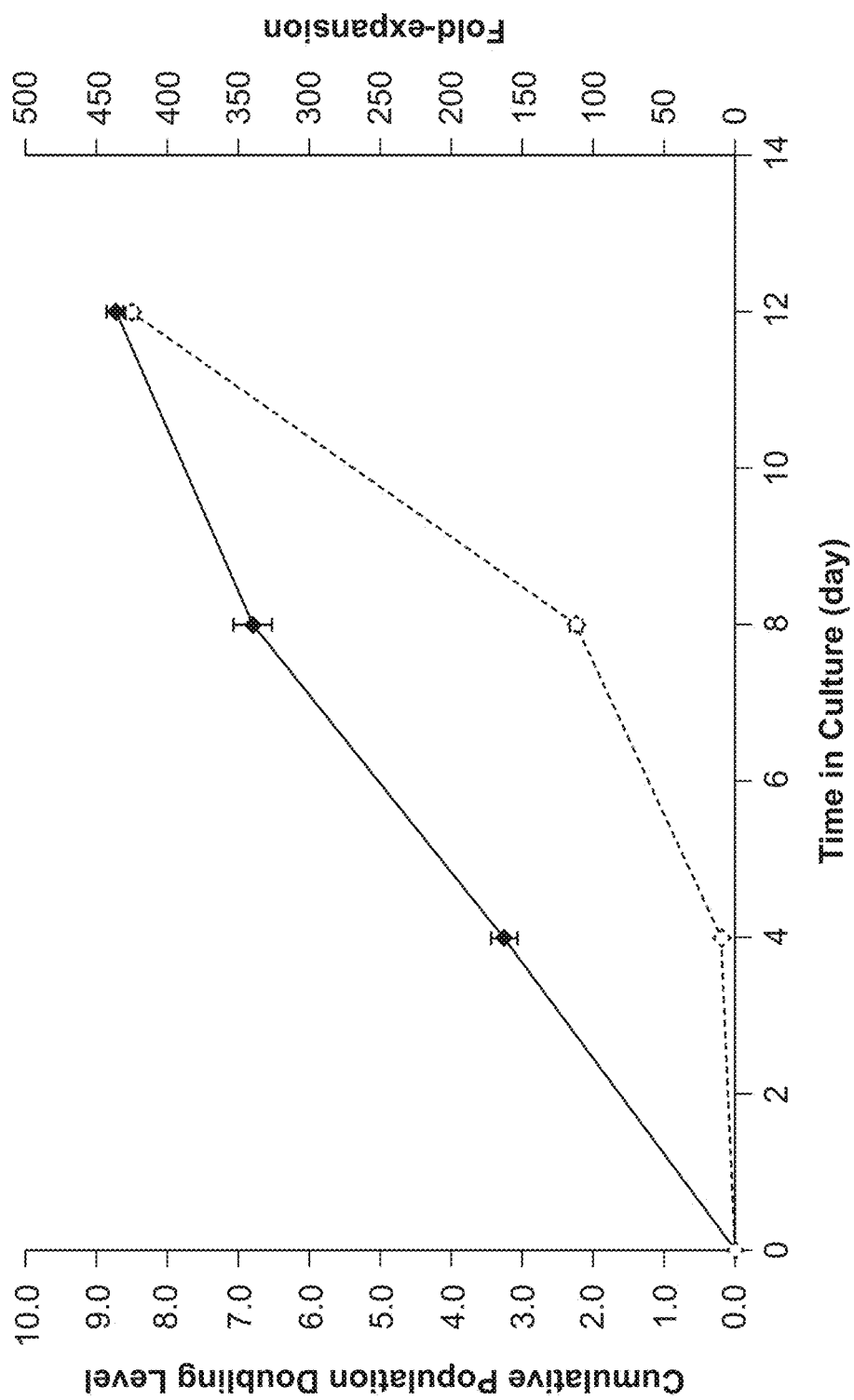
FIG. 19 shows the results of cell expansion experiments.

Cell expansion was found to vary based on collection protocol (FIG. 19).

Figure 20:
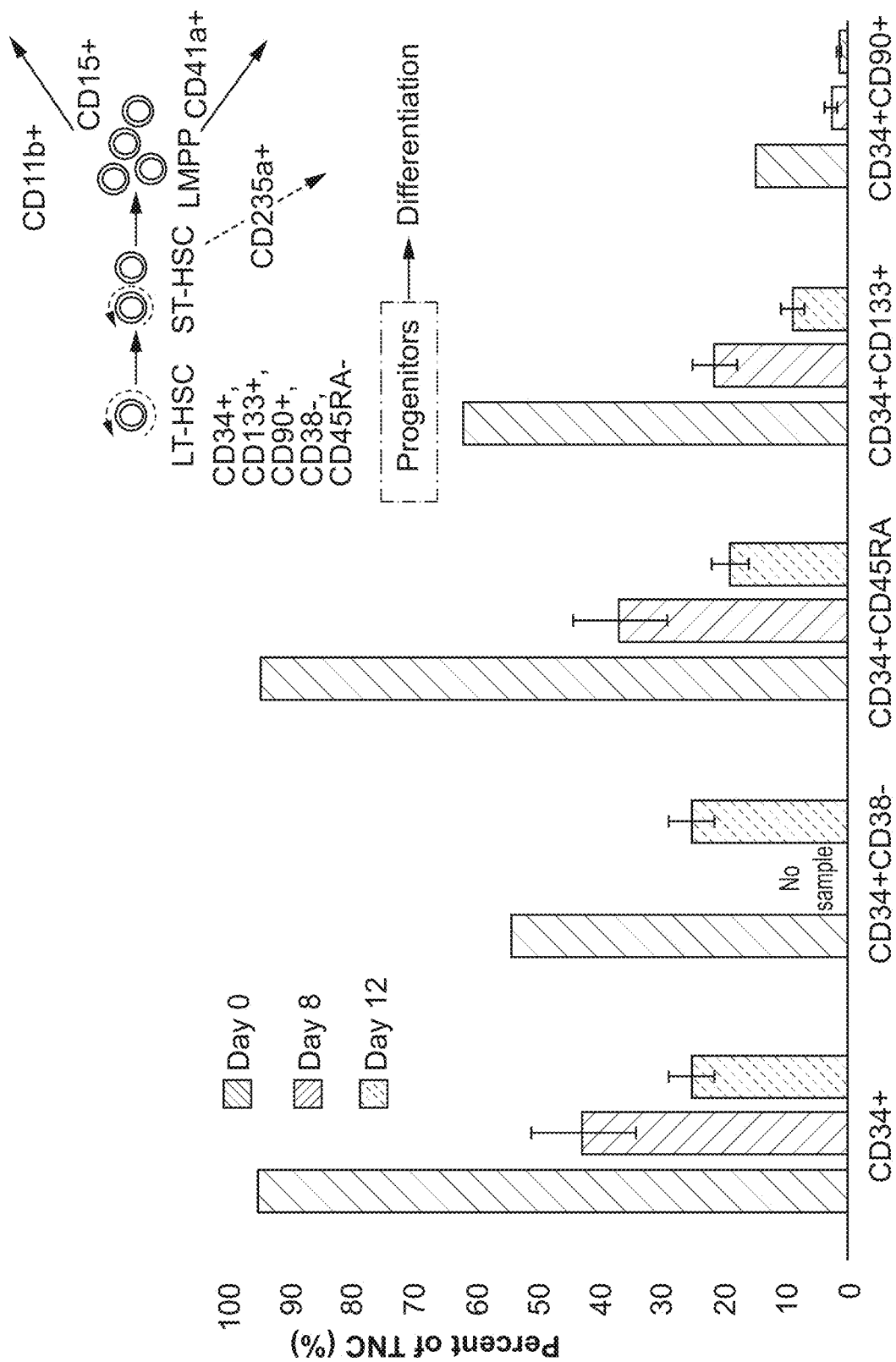
FIG. 20 shows the results of cell expansion following 12 days of expansion.

Changes in cell phenotype are tracked during the culture period 25.3% of the TNC are CD34+ following 12 days of expansion (FIG. 20)

Figure 21:
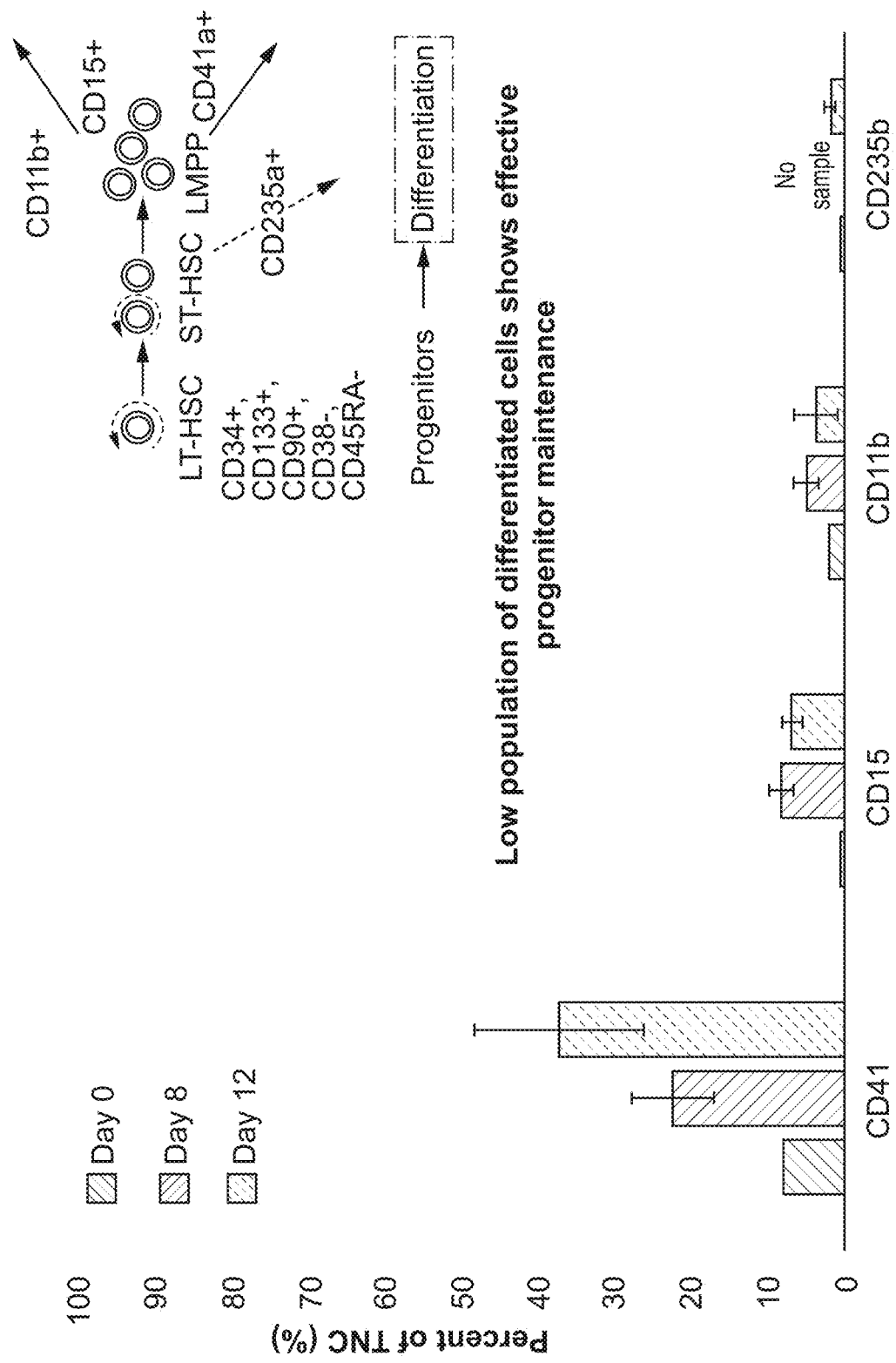
FIG. 21 shows differentiation of cell phenotype.

Differentiated cell phenotype is shown in FIG. 21. FIG. 22 demonstrates that single colonies are capable of forming multi-lineage differentiation.

REFERENCES CITED

FDA, Regenerative Medicine Advanced Therapy Designation. (2017). Available at: fda.gov/BiologicsBloodVaccines/CellularGeneTherapyProducts/ucm537670.htm. (Accessed: 8 Aug. 2017)

Wang, X. & Rivière, I. Clinical manufacturing of CAR T cells: foundation of a promising therapy. Mol. Ther. —Oncolytics 3, 16015 (2016).

Jones, S. D., McKee, S. & Levine, H. L. Emerging challenges in cell therapy manufacturing. BioProcess Int 10, S4-S7 (2012).

Trainor, N., Pietak, A. & Smith, T. Rethinking clinical delivery of adult stem cell therapies. Nat Biotech 32, 729-735 (2014).

Nilsson, C. et al. Optimal Blood Mononuclear Cell Isolation Procedures for Gamma Interferon Enzyme-Linked Immunospot Testing of Healthy Swedish and Tanzanian Subjects. Clin. Vaccine Immunol. 15, 585-589 (2008).

Bohnenkamp, H., Hilbert, U. & Noll, T. Bioprocess development for the cultivation of human T-lymphocytes in a clinical scale. Cytotechnology 38, 135-145 (2002).

Lu, F. et al. Automated dynamic fed-batch process and media optimization for high productivity cell culture process development. Biotechnol. Bioeng. 110, 191-205 (2013).

Hollyman, D. et al. Manufacturing validation of biologically functional T cells targeted to CD19 antigen for autologous adoptive cell therapy. J. Immunother. 32, 169-180 (2009).

FDA, Sepax Cell Separation System and single use kits. (2011). Available at: fda.gov/downloads/BiologicsBlood-Vaccines/BloodBloodProducts/ApprovedProducts/ SubstantiallyEquivalent510kDeviceInformation/ UCM278385.pdf. (Accessed: 8 Nov. 2017)

Wegener, C. Cell Washing with the LOVO Cell Processing System. BioProcess Int Industry Y, p 78 (2014).

Trickett, A. & Kwan, Y. L. T cell stimulation and expansion using anti-CD3/CD28 beads. J. Immunol. Methods 275, 251-255 (2003).

Hasegawa, K. et al. In vitro stimulation of CD8 and CD4 T cells by dendritic cells loaded with a complex of cholesterol-bearing hydrophobized pullulan and NY-ESO-1 protein: Identification of a new HLA-DR15-binding CD4 T-cell epitope. Clin. Cancer Res. 12, 1921-1927 (2006).

Odeleye, A. O. O., Marsh, D. T. J., Osborne, M. D., Lye, G. J. & Micheletti, M. On the fluid dynamics of a laboratory scale single-use stirred bioreactor. Chem. Eng. Sci. 111, 299-312 (2014).

Grishagin, I. V. Automatic cell counting with ImageJ. Anal. Biochem. 473, 63-65 (2015).

Levine, B. L., Miskin, J., Wonnacott, K. & Keir, C. Global Manufacturing of CAR T Cell Therapy. Mol. Ther. Methods Clin. Dev. 4, 92-101 (2017).

Locke, F. L. et al. Abstract CT019: Primary results from ZUMA-1: a pivotal trial of axicabtagene ciloleucel (axicel; KTE-C19) in patients with refractory aggressive non-Hodgkin lymphoma (NHL). Cancer Res. 77, CT019 LP-CT019 (2017).

Lu Y C, Parker L L, Lu T, Zheng Z, Toomey M A, White D E, Yao X, Li Y F, Robbins P F, Feldman S A, van der Bruggen P, Klebanoff C A, Goff S L, Sherry M S, Kammula U S, Yang J C, Rosenberg S A. Treatment of patients with metastatic cancer using a major histocompatibility complex class II-restricted T-cell receptor targeting the cancer germline antigen MAGE-A3. Journal of Clinical Oncology (2017) 35: 29, 3322-3329.

FDA, Available online at: fda.gov/downloads/Advisory-Committees/CommitteesMeetingMaterials/Drugs/On cologicDrugsAdvisoryCommittee/UCM566166.pdf Berdeja J G, Lin Y, Raje N S, Siegel D S D, Munshi N C, Liedtke M, Jagannath S, Maus M V, Turka A, Lam L P, Hege K, Morgan R, Quigley M T, Kochenderfer J. First-in-human multicenter study of bb2121 anti-BCMA CAR T-cell therapy for relapsed/refractory multiple myeloma: Updated results. Journal of Clinical Oncology 2017 35:15_suppl, 3010-3010

Kebriaei P, Singh H, Huls M H, Figiola M J, Bassett R, Olivares S, Jena B, Dawson M J, Kumaresan P R, Su S, Maiti S, Dai J, Moriarity B, Forget M A, Senyukov V, Orozco A, Liu T, McCarty J, Jackson R N, Moyes J S, Rondon G, Qazilbash M, Ciurea S, Alousi A, Nieto Y, Rezvani K, Marin D, Popat U, Hosing C, Shpall E J, Kantarjian H, Keating M, Wierda W, Do K A, Largaespada D A, Lee D A, Hackett P B, Champlin R E, Cooper L J N. Phase I trials using Sleeping Beauty to generate CD19-specific CAR T cells. J Clin Invest. 2016 Sep. 1; 126(9): 3363-3376.

Morrissey J B, Shi Y, Trainor N. End-to-end cell therapy automation: an immunotherapy case study. BioProcess International (2017) 10-18.

Lafferty K J, Cunningham A J A. New analysis of allogeneic interactions. J. Immunol. (1975) 112: 436-437.

Harding F, McArthur J, Gross J, Raulet D, Allison J. CD28-mediated signalling co-stimulates murine T cells and prevents induction of anergy in T-cell clones (1992) Nature 356: 607-609.

Clavreul A, Fisson S, D'hellencourt CL, Couez D. Interelationship between CD3 and CD28 pathways in a murine T cell thymoma. Mol Immunol. (2000) 37(10): 571-7.

Charron L, Doctrinal A, Choileain S N, Astier A L. Monocyte:T cell interaction regulates human T cell activation through a CD28/CD46 crosstalk. Immunol Cell Biol. (2015) 93(9): 796-803.

Fathman CG1, Lineberry N B. Molecular mechanisms of CD4+ T-cell anergy. Nat Rev Immunol. (2007) 7(8): 599-609.

Greenwald R J, Freeman G J, Sharpe A H. The B7 family revisited. Annual Review of Immunology (2005) 23(1): 515-548.

Kochenderfer J N, Dudley M E, Kassim S H, et al. Chemotherapy-refractory diffuse large B-cell lymphoma and indolent B-cell malignancies can be effectively treated with autologous T cells expressing an anti-CD19 chimeric antigen receptor. Journal of Clinical Oncology (2015); 33(6): 540-549.

Kalos M, Levine B L, Porter D L, et al. T Cells with Chimeric Antigen Receptors Have Potent Antitumor Effects and Can Establish Memory in Patients with Advanced Leukemia. Science Translational Medicine (2011) 3(95): 95ra73.

Riddell S R, Greenberg P D. The use of anti-CD3 and anti-CD28 monoclonal antibodies to clone and expand human antigen-specific T cells. J Immunol Methods (1990) Apr. 17; 128(2): 189-201.

Trickett A, Kwan Y L. T cell stimulation and expansion using anti-CD3/CD28 beads. Journal of Immunological Methods. 275 (2003) 251-255.

Dudley M E, Wunderlich J R, Shelton T E, Even J, Rosenberg S A. Generation of Tumor-Infiltrating Lymphocyte Cultures for Use in Adoptive Transfer Therapy for Melanoma Patients. Journal of immunotherapy (2003) 26(4): 332-342.

Dudley M E, Wunderlich J R, Shelton T E, Even J, Rosenberg S A. Generation of tumor-infiltrating lymphocyte cultures for use in adoptive transfer therapy for melanoma patients. J Immunother. (2003) 26(4): 332-342.

Manger B, Weiss A, Weyand C, Goronzy J, Stobo J D. T cell activation: differences in the signals required for IL 2 production by nonactivated and activated T cells. J Immunother. (1985) 135 (6) 3669-3673.

Ceuppens J, Bloemmen F J, Van Wauwe J P. T cell unresponsiveness to the mitogenic activity of OKT3 antibody results from a deficiency of monocyte Fc gamma receptors for murine IgG2a and inability to cross-link the T3-Ti complex. J Immunol (1985) 135 (6) 3882-3886.

Van Wauwe J P, De Mey J R, Goossens J G. OKT3: a monoclonal anti-human T lymphocyte antibody with potent mitogenic properties. J Immunol. (1980) 124(6): 2708-13.

Carpenter P A, Pavlovic S, Tso J Y, Press O W, Gooley T, Yu X Z, Anasetti C. Non-Fc receptor-binding humanized anti-CD3 antibodies induce apoptosis of activated human T cells. J Immunol (2000) 165 (11) 6205-6213.

Andris F, Denanglaire S, de Mattia F, Urbain J, Leo O. Naive T cells are resistant to anergy induction by anti-CD3 antibodies. J of Immunology (2004) 173 (5) 3201-3208.

Wolf H, Müller Y, Salmen S, Wilmanns W, Jung G. Induction of anergy in resting human T lymphocytes by immobilized anti-CD3 antibodies. Eur J Immunol. (1994) 24(6): 1410-1417.

Chai J G, Lechler R I. Immobilized anti-CD3 mAb induces anergy in murine naive and memory CD4+ T cells in vitro. Int Immunol. (1997) 9(7): 935-944.

Verwilghen J, Baroja M L, Van Vaeck F, Van Damme J, Ceuppens J L. Differences in the stimulating capacity of immobilized anti-CD3 monoclonal antibodies: variable dependence on interleukin-1 as a helper signal for T-cell activation. Immunology (1991) 72(2): 269-276.

Schwartz R H. A cell-culture model for lymphocyte-T clonal anergy. Science (1990) 248: 1349-1356.

Ju S W, Ju S G, Wang F M, Gu Z J, Qiu Y H, Yu G H, Ma H B, Zhang X G. A functional anti-human 4-1BB ligand monoclonal antibody that enhances proliferation of monocytes by reverse signaling of 4-1 BBL. Hybridoma and Hybridomics. (2003) 22: 333-338.

Baroja M L, Lorre K, Van Vaeck F, Ceuppens J L. The anti-T cell monoclonal antibody 9.3 (anti-CD28) provides a helper signal and bypasses the need for accessory cells in T cell activation with immobilized anti-CD3 and mitogens. Cell Immunol. (1989) 120(1): 205-217.

Austyn J M, Smith K G, Morris P J. T cell activation by anti-CD3 antibodies: function of Fc receptors on B cell blasts, but not resting B cells, and CD18 on the responding T cells. Eur J Immunol. 1987 17(9): 1329-35.

Tax W J M, Willems H W, Reekers P P M, Capel P J A, Koene R A P. Polymorphism in mitogenic effect of IgG1 monoclonal antibodies against T3 antigen on human T cells. Nature (1983) 304: 445-447.

Fleischer J, Soeth E, Reiling N, Grage-Griebenow E, Flad H D, Ernst M. Differential expression and function of CD80 (B7-1) and CD86 (B7-2) on human peripheral blood monocytes. Immunology (1996) 89(4): 592-598.

Schwartz R H. T cell anergy. Annual Review Immunology (2003) 21: 305-34.

Feldmann A, Arndt C, Töpfer K, Stamova S, Krone F, Cartellieri M, Koristka S, Michalk I, Lindemann D, Schmitz M, Temme A, Bornhäuser M, Ehninger G, Bachmann M. Novel humanized and highly efficient bispecific antibodies mediate killing of prostate stem cell antigen-expressing tumor cells by CD8+ and CD4+ T cells. J Immunol. (2012) 189(6): 3249-3259.

Reusch U, Duell J, Ellwanger K, Herbrecht C, Knackmuss S H, Fucek I, Eser M, McAleese F, Molkenthin V, Gall F L, et al. A tetravalent bispecific TandAb (CD19/CD3), AFM11, efficiently recruits T cells for the potent lysis of CD19(+) tumor cells. MAbs. (2015) 7: 584-604.

Church S E, Jensen S M, Antony P A, Restifo N P, Fox B A. Tumor-specific CD4+ T cells maintain effector and memory tumor-specific CD8+ T cells. Eur J Immunol. (2014) 44(1): 69-79.

Feldmann A, Arndt C, Töpfer K, Stamova S, Krone F, Cartellieri M, Koristka S, Michalk I, Lindemann D, Schmitz M, Temme A, Bornhäuser M, Ehninger G, Bachmann M. Novel humanized and highly efficient bispecific antibodies mediate killing of prostate stem cell antigen-expressing tumor cells by CD8+ and CD4+ T cells. J Immunol. (2012) 189: 3249-3259.

Reusch U, Duell J, Ellwanger K, Herbrecht C, Knackmuss S H, Fucek I, Eser M, McAleese F, Molkenthin V, Gall F L, Topp M, Little M, Zhukovsky E A. A tetravalent bispecific TandAb (CD19/CD3), AFM11, efficiently recruits T cells for the potent lysis of CD19(+) tumor cells. (2015) 7:584-604.

Riddell S R, Sommermeyer D, Berger C, et al. Adoptive therapy with chimeric antigen receptor-modified T cells of defined subset composition. Cancer J. (2014) 20(2): 141-144.

Turtle C J, Hanafi L-A, Berger C, et al. CD19 CAR-T cells of defined CD4+:CD8+ composition in adult B cell ALL patients. The Journal of Clinical Investigation. (2016) 126(6): 2123-2138.

Locke F L, Neelapu S S, Bartlett N L, Siddiqi T, Siddiqi T, Chavez J C, Hosing C M, Ghobadi A, Budde L E, Bot A, Rossi J M, Jiang Y, Xue A X, Elias M, Aycock J, Wiezorek J, Go W Y. Phase 1 Results of ZUMA-1: A multicenter study of KTE-C19 anti-CD19 CAR T cell therapy in refractory aggressive lymphoma. Molecular Therapy (2017) 25(1): 285-295.

Trainor N, Pietak A, Smith T. Rethinking clinical delivery of adult stem cell therapies. Nature Biotech (2014) 729-735.

Mandavi B, Gottschalk U, Trainor N, Smith T. The hype, hope and reality of personalization. The Medicine Maker (2015) 38-41.

Yan M, Schwaederle M, Arguello D, Millis S Z, Gatalica Z, Kurzrock R. HER2 expression status in diverse cancers: review of results from 37,992 patients. Cancer Metastasis Review (2015) 34(1): 157-164.

Tuefferd M, Couturier J, Penault-Llorca F, Vincent-Salomon A, Broët P, Guastalla J P, Allouache D, Combe M, Weber B, Pujade-Lauraine E, Camilleri-BroëtS. HER2 Status in Ovarian Carcinomas: A Multicenter GINECO Study of 320 Patients (2007) 2(11):e1138.

Lu T L, Pugach M, Somerville R, Rosenberg S A, Kochendefer J N, Better M, Feldman S A. A rapid cell expansion process for production of engineered autologous CAR-T cell therapies. Human Gene Therapy (2016) 27: 209-218.

Nociari M M, Shalev A, Benias P, Russo C. A novel one-step, highly sensitive fluorometric assay to evaluate cell-mediated cytotoxicity. J Immunol Methods (1998) 213(2): 157-167.

Romagnani S. Type 1 T helper and type 2 T helper cells: functions, regulation and role in protection and disease. Int J Clin Lab Res (1991) 21(2): 152-158.

Fleischer J, Soeth E, Reiling N, Grage-Griebenow E, Flad H D, Ernst M. Differential expression and function of CD80 (B7-1) and CD86 (B7-2) on human peripheral blood monocytes. Immunology (1996) 89(4): 592-598.

Laux I, Khoshnan A, Tindell C, Bae D, Zhu X M, June C H, Effros R B, Nel A. Response differences between human CD4+ and CD8+ T-cells during CD28 costimulation: Implications for immune cell-based therapies and studies related to the expansion of double-positive T-cells during aging. Clin Immunol. (2000) 96: 187-197.

Li Y, Kurlander R J. Comparison of anti-CD3 and anti-CD28-coated beads with soluble anti-CD3 for expanding human T cells: Differing impact on CD8 T cell phenotype and responsiveness to restimulation. J Transl Med. (2010) 8: 104.

Zhu Y W, Zhu G F, Luo L Q, Flies A S, Chen L P. CD137 stimulation delivers an antigen-independent growth signal for T lymphocytes with memory phenotype. Blood (2007) $10^9$: 4882-4889.

Ledbetter J A, Imboden J B, Schieven G L, Grosmaire L S, Rabinovitch P S, Lindsten T, Thompson C B, June C H. CD28 Ligation in T-cell Activation: Evidence for Two Signal Transduction Pathways. Blood (1990) 75(7): 1531-1539.

Atkuri K R, Herzenberg L A, Herzenberg L A. Culturing at atmospheric oxygen levels impacts lymphocyte function. Proceedings of the National Academy of Sciences of the United States of America (2005) 102(10): 3756-3759.

Avgoustiniatos E S, Hering B J, Rozak P R, et al. Commercially Available Gas-Permeable Cell Culture Bags May Not Prevent Anoxia in Cultured or Shipped Islets. Transplantation proceedings. 2008; 40(2):395-400.

Hammill J A, VanSeggelen H, Helsen C W, Denisova G F, Evelegh C, Tantalo D G M, Bassett J D, Bramson J L. Designed ankyrin repeat proteins are effective targeting elements for chimeric antigen receptors. Journal for ImmunoTherapy of Cancer (2015) 3:55.

VanSeggelen H, Tantalo D G M, Afsahi A, Hammill J A, Bramson J L. Chimeric antigen receptor-engineered T cells as oncolytic virus carriers. Molecular Therapy—Oncolytics (2015) 2, 150014.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

The invention claimed is:

1. A method for automated production of a genetically modified T cell culture, the method comprising:
   (a) activating a T cell culture with an activation reagent selected from an antibody and a dendritic cell to produce an activated T cell culture in a first chamber of a fully enclosed cell engineering system;
   (b) transducing within the first chamber the activated T cell culture with a viral vector encoding an ectodomain, a transmembrane domain, and an endodomain, to introduce the viral vector into the activated T cell culture and produce a transduced T cell culture;
   (c) expanding within the first chamber of the cell engineering system, the transduced T cell culture;
   (d) concentrating the expanded T cell culture of (c); and
   (e) harvesting the concentrated T cell culture of (d) to produce a genetically modified T cell culture,
   wherein (a) through (e) are performed within the fully enclosed cell engineering system,
   wherein the fully enclosed cell engineering system is pre-filled with the cell culture, a culture media, the activation reagent, and/or the viral vector, prior to starting the method, and
   wherein expansion of the transduced T cell culture in (c) produces at least 20% more genetically modified T cells than expansion utilizing manual cell culture with a flexible, gas permeable bag and transduction efficiency of the method is at least 20% higher than transduction efficiency utilizing manual cell culture with the flexible, gas permeable bag.

2. The method of claim 1, wherein the cell engineering system is configured to store the culture media, the activation reagent, and/or the viral vector in a low-temperature chamber.

3. The method of claim 2, wherein the method further includes warming the media before introducing the warmed media to the cell culture.

4. The method of claim 1, wherein the first chamber is a chamber for growing cells, and wherein the cell engineering system further includes additional chambers for storing the cell culture, the culture media, the activation reagent, and/or the viral vector.

5. The method of claim 1, wherein the cell engineering system includes multiple reagent bags to enable all reagents required for the process to be pre-loaded and stored.

6. The method of claim 1, wherein the method process is a self-adjusting process and includes:
   (a) monitoring with one or more of a temperature sensor, a pH sensor, a glucose sensor, an oxygen sensor, a carbon dioxide sensor, and an optical density sensor; and
   (b) adjusting one or more of a temperature, a pH level, a glucose level, an oxygen level, a carbon dioxide level, and an optical density of the transduced T cell culture, based on the monitoring.

7. The method of claim 1, wherein the method produces at least about 100 million viable genetically modified T cells.

8. The method of claim 1, wherein T cell culture is a chimeric antigen receptor T (CAR T) cell culture.

9. The method of claim 1, wherein the vector encodes a chimeric antigen receptor.

10. The method of claim 1, wherein the expanding comprises feeding, washing, monitoring, and selecting of the transduced T cell culture.

11. The method of claim 1, wherein the cell engineering system is capable of performing several rounds of feeding, washing, monitoring, and selecting of the transduced T cell culture.

12. The method of claim 1, wherein the concentrating comprises centrifugation, supernatant removal following sedimentation, or filtration.

13. The method of claim 1, further comprising removing the activation reagent from the activated T cell culture after step (a).

14. The method of claim 1, further comprising removing the viral vector following the transducing in (b).

15. The method of claim 1, wherein the cell culture comprises at least one accessory cell.

16. The method of claim 15, wherein the accessory cell is a monocyte, an antigen-presenting cell or a dendritic cell.

17. The method of claim 15, wherein the accessory cell comprises antigens for a T cell receptor, selected from CD28, CD40, CD2, CD40L, ICOS and combinations thereof.

* * * * *